US012029644B2

(12) United States Patent
Gurovich et al.

(10) Patent No.: US 12,029,644 B2
(45) Date of Patent: Jul. 9, 2024

(54) FRAME FOR PROSTHETIC HEART VALVE

(71) Applicant: Edwards Lifesciences Corporation, Irvine, CA (US)

(72) Inventors: Nikolai Gurovich, Hadera (IL); Alexey Tsypenyuk, Draper, UT (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 0 days.

(21) Appl. No.: 16/937,964

(22) Filed: Jul. 24, 2020

(65) Prior Publication Data
US 2020/0352709 A1 Nov. 12, 2020

Related U.S. Application Data

(63) Continuation of application No. PCT/US2020/013725, filed on Jan. 15, 2020.
(Continued)

(51) Int. Cl.
*A61F 2/24* (2006.01)

(52) U.S. Cl.
CPC .......... *A61F 2/2418* (2013.01); *A61F 2/2409* (2013.01); *A61F 2/2433* (2013.01);
(Continued)

(58) Field of Classification Search
CPC .... A61F 2/2418; A61F 2/2409; A61F 2/2433; A61F 2/24; A61F 2230/001; A61F 2250/0039
See application file for complete search history.

(56) References Cited

U.S. PATENT DOCUMENTS 3,409,013 A 11/1968 Berry
3,548,417 A 12/1970 Kisher
(Continued)

FOREIGN PATENT DOCUMENTS

DE 0144167 C 9/1903
DE 2246526 A1 3/1973
(Continued)

OTHER PUBLICATIONS

H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.
(Continued)

*Primary Examiner* — Jacqueline Woznicki
(74) *Attorney, Agent, or Firm* — Carsten C. Grellmann; KLARQUIST SPARKMAN, LLP

(57) ABSTRACT

A prosthetic heart valve includes a frame having an inflow end, an outflow end, and a central portion. The frame is radially expandable from a collapsed configuration to an expanded configuration. The inflow end includes a plurality of first strut members having a first strut width and forming a first angle between adjacent first strut members, and the central portion includes a plurality of second strut members having a second strut width and forming a second angle between adjacent second strut members. A plurality of leaflets are positioned within the frame. At least one of the first angle and the second angle, or the first strut width and the second strut width, are different such that when the prosthetic heart valve is crimped onto a cylindrical balloon and expanded using the cylindrical balloon, a diameter of the outflow end is different from a diameter of the central portion.

12 Claims, 31 Drawing Sheets

Related U.S. Application Data

(60) Provisional application No. 62/858,249, filed on Jun. 6, 2019, provisional application No. 62/793,692, filed on Jan. 17, 2019.

(52) U.S. Cl.
CPC ... *A61F 2230/001* (2013.01); *A61F 2230/006* (2013.01); *A61F 2250/0039* (2013.01)

(56) References Cited

U.S. PATENT DOCUMENTS

| | | | |
|---|---|---|---|
| 3,587,115 A | 6/1971 | Shiley | |
| 3,657,744 A | 4/1972 | Ersek | |
| 3,671,979 A | 6/1972 | Moulopoulos | |
| 3,714,671 A | 2/1973 | Edwards et al. | |
| 3,755,823 A | 9/1973 | Hancock | |
| 4,035,849 A | 7/1977 | Angell et al. | |
| 4,056,854 A | 11/1977 | Boretos et al. | |
| 4,106,129 A | 8/1978 | Carpentier et al. | |
| 4,222,126 A | 9/1980 | Boretos et al. | |
| 4,265,694 A | 5/1981 | Boretos et al. | |
| 4,297,749 A | 11/1981 | Davis et al. | |
| RE30,912 E | 4/1982 | Hancock | |
| 4,339,831 A | 7/1982 | Johnson | |
| 4,343,048 A | 8/1982 | Ross et al. | |
| 4,345,340 A | 8/1982 | Rosen | |
| 4,373,216 A | 2/1983 | Klawitter | |
| 4,406,022 A | 9/1983 | Roy | |
| 4,441,216 A | 4/1984 | Ionescu et al. | |
| 4,470,157 A | 9/1984 | Love | |
| 4,535,483 A | 8/1985 | Klawitter et al. | |
| 4,574,803 A | 3/1986 | Storz | |
| 4,592,340 A | 6/1986 | Boyles | |
| 4,605,407 A | 8/1986 | Black et al. | |
| 4,612,011 A | 9/1986 | Kautzky | |
| 4,643,732 A | 2/1987 | Pietsch et al. | |
| 4,655,771 A | 4/1987 | Wallsten | |
| 4,692,164 A | 9/1987 | Dzemeshkevich et al. | |
| 4,733,665 A | 3/1988 | Palmaz | |
| 4,759,758 A | 7/1988 | Gabbay | |
| 4,762,128 A | 8/1988 | Rosenbluth | |
| 4,777,951 A | 10/1988 | Cribier et al. | |
| 4,787,899 A | 11/1988 | Lazarus | |
| 4,787,901 A | 11/1988 | Baykut | |
| 4,796,629 A | 1/1989 | Grayzel | |
| 4,820,299 A | 4/1989 | Philippe et al. | |
| 4,829,990 A | 5/1989 | Thuroff et al. | |
| 4,851,001 A | 7/1989 | Taheri | |
| 4,856,516 A | 8/1989 | Hillstead | |
| 4,878,495 A | 11/1989 | Grayzel | |
| 4,878,906 A | 11/1989 | Lindemann et al. | |
| 4,883,458 A | 11/1989 | Shiber | |
| 4,922,905 A | 5/1990 | Strecker | |
| 4,966,604 A | 10/1990 | Reiss | |
| 4,979,939 A | 12/1990 | Shiber | |
| 4,986,830 A | 1/1991 | Owens et al. | |
| 4,994,077 A | 2/1991 | Dobben | |
| 5,007,896 A | 4/1991 | Shiber | |
| 5,026,366 A | 6/1991 | Leckrone | |
| 5,032,128 A | 7/1991 | Alonso | |
| 5,037,434 A | 8/1991 | Lane | |
| 5,047,041 A | 9/1991 | Samuels | |
| 5,059,177 A | 10/1991 | Towne et al. | |
| 5,080,668 A | 1/1992 | Bolz et al. | |
| 5,085,635 A | 2/1992 | Cragg | |
| 5,089,015 A | 2/1992 | Ross | |
| 5,152,771 A | 10/1992 | Sabbaghian et al. | |
| 5,163,953 A | 11/1992 | Vince | |
| 5,167,628 A | 12/1992 | Boyles | |
| 5,192,297 A | 3/1993 | Hull | |
| 5,266,073 A | 11/1993 | Wall | |
| 5,282,847 A | 2/1994 | Trescony et al. | |
| 5,295,958 A | 3/1994 | Shturman | |
| 5,332,402 A | 7/1994 | Teitelbaum | |
| 5,360,444 A | 11/1994 | Kusuhara | |
| 5,370,685 A | 12/1994 | Stevens | |
| 5,397,351 A | 3/1995 | Pavcnik et al. | |
| 5,411,055 A | 5/1995 | Kane | |
| 5,411,552 A | 5/1995 | Andersen et al. | |
| 5,443,446 A | 8/1995 | Shturman | |
| 5,480,424 A | 1/1996 | Cox | |
| 5,500,014 A | 3/1996 | Quijano et al. | |
| 5,545,209 A | 8/1996 | Roberts et al. | |
| 5,545,214 A | 8/1996 | Stevens | |
| 5,549,665 A | 8/1996 | Vesely et al. | |
| 5,554,185 A | 9/1996 | Block et al. | |
| 5,558,644 A | 9/1996 | Boyd et al. | |
| 5,571,175 A | 11/1996 | Vanney et al. | |
| 5,584,803 A | 12/1996 | Stevens et al. | |
| 5,591,185 A | 1/1997 | Kilmer et al. | |
| 5,591,195 A | 1/1997 | Taheri et al. | |
| 5,607,464 A | 3/1997 | Trescony et al. | |
| 5,609,626 A | 3/1997 | Quijano et al. | |
| 5,628,792 A | 5/1997 | Lentell | |
| 5,639,274 A | 6/1997 | Fischell et al. | |
| 5,665,115 A | 9/1997 | Cragg | |
| 5,716,417 A | 2/1998 | Girard et al. | |
| 5,728,068 A | 3/1998 | Leone et al. | |
| 5,749,890 A | 5/1998 | Shaknovich | |
| 5,756,476 A | 5/1998 | Epstein et al. | |
| 5,769,812 A | 6/1998 | Stevens et al. | |
| 5,800,508 A | 9/1998 | Goicoechea et al. | |
| 5,840,081 A | 11/1998 | Andersen et al. | |
| 5,855,597 A | 1/1999 | Jayaraman | |
| 5,855,601 A | 1/1999 | Bessler et al. | |
| 5,855,602 A | 1/1999 | Angell | |
| 5,922,021 A * | 7/1999 | Jang ............... A61F 2/91 623/1.15 |
| 5,925,063 A | 7/1999 | Khosravi | |
| 5,957,949 A | 9/1999 | Leonhardt et al. | |
| 6,027,525 A | 2/2000 | Suh et al. | |
| 6,132,473 A | 10/2000 | Williams et al. | |
| 6,168,614 B1 | 1/2001 | Andersen et al. | |
| 6,171,335 B1 | 1/2001 | Wheatley et al. | |
| 6,174,327 B1 | 1/2001 | Mertens et al. | |
| 6,210,408 B1 | 4/2001 | Chandrasekaran et al. | |
| 6,217,585 B1 | 4/2001 | Houser et al. | |
| 6,221,091 B1 | 4/2001 | Khosravi | |
| 6,231,602 B1 | 5/2001 | Carpentier et al. | |
| 6,245,102 B1 | 6/2001 | Jayaraman | |
| 6,299,637 B1 | 10/2001 | Shaolian et al. | |
| 6,302,906 B1 | 10/2001 | Goicoechea et al. | |
| 6,338,740 B1 | 1/2002 | Carpentier | |
| 6,350,277 B1 | 2/2002 | Kocur | |
| 6,352,547 B1 | 3/2002 | Brown et al. | |
| 6,425,916 B1 | 7/2002 | Garrison et al. | |
| 6,440,764 B1 | 8/2002 | Focht et al. | |
| 6,454,799 B1 | 9/2002 | Schreck | |
| 6,458,153 B1 | 10/2002 | Bailey et al. | |
| 6,461,382 B1 | 10/2002 | Cao | |
| 6,468,660 B2 | 10/2002 | Ogle et al. | |
| 6,482,228 B1 | 11/2002 | Norred | |
| 6,488,704 B1 | 12/2002 | Connelly et al. | |
| 6,527,979 B2 | 3/2003 | Constantz et al. | |
| 6,569,196 B1 | 5/2003 | Vesely | |
| 6,582,462 B1 | 6/2003 | Andersen et al. | |
| 6,605,112 B1 | 8/2003 | Moll et al. | |
| 6,652,578 B2 | 11/2003 | Bailey et al. | |
| 6,689,123 B2 | 2/2004 | Pinchasik | |
| 6,716,244 B2 | 4/2004 | Klaco | |
| 6,730,118 B2 | 5/2004 | Spenser et al. | |
| 6,733,525 B2 | 5/2004 | Yang et al. | |
| 6,767,362 B2 | 7/2004 | Schreck | |
| 6,769,161 B2 | 8/2004 | Brown et al. | |
| 6,783,542 B2 | 8/2004 | Eidenschink | |
| 6,830,584 B1 | 12/2004 | Seguin | |
| 6,878,162 B2 | 4/2005 | Bales et al. | |
| 6,893,460 B2 | 5/2005 | Spenser et al. | |
| 6,908,481 B2 | 6/2005 | Cribier | |
| 6,936,067 B2 | 8/2005 | Buchanan | |
| 7,018,406 B2 | 3/2006 | Seguin et al. | |
| 7,018,408 B2 | 3/2006 | Bailey et al. | |
| 7,096,554 B2 | 8/2006 | Austin et al. | |

(56) References Cited

U.S. PATENT DOCUMENTS

| | | |
|---|---|---|
| 7,225,518 B2 | 6/2007 | Eidenschink et al. |
| 7,276,078 B2 | 10/2007 | Spenser et al. |
| 7,276,084 B2 | 10/2007 | Yang et al. |
| 7,316,710 B1 | 1/2008 | Cheng et al. |
| 7,318,278 B2 | 1/2008 | Zhang et al. |
| 7,374,571 B2 | 5/2008 | Pease et al. |
| 7,393,360 B2 | 7/2008 | Spenser et al. |
| 7,462,191 B2 | 12/2008 | Spenser et al. |
| 7,510,575 B2 | 3/2009 | Spenser et al. |
| 7,563,280 B2 | 7/2009 | Anderson et al. |
| 7,585,321 B2 | 9/2009 | Cribier |
| 7,618,446 B2 | 11/2009 | Andersen et al. |
| 7,618,447 B2 | 11/2009 | Case et al. |
| 7,655,034 B2 | 2/2010 | Mitchell et al. |
| 7,785,366 B2 | 8/2010 | Maurer et al. |
| 7,959,665 B2 | 6/2011 | Pienknagura |
| 7,959,672 B2 | 6/2011 | Salahieh et al. |
| 7,993,394 B2 | 8/2011 | Hariton et al. |
| 8,029,556 B2 | 10/2011 | Rowe |
| 8,075,611 B2 | 12/2011 | Millwee et al. |
| 8,128,686 B2 | 3/2012 | Paul, Jr. et al. |
| 8,167,932 B2 | 5/2012 | Bourang et al. |
| 8,291,570 B2 | 10/2012 | Eidenschink et al. |
| 8,308,798 B2 * | 11/2012 | Pintor ............... A61F 2/2433 623/2.18 |
| 8,348,998 B2 | 1/2013 | Pintor et al. |
| 8,449,606 B2 | 5/2013 | Eliasen et al. |
| 8,454,685 B2 | 6/2013 | Hariton et al. |
| 8,652,202 B2 * | 2/2014 | Alon ............... A61F 2/2418 623/2.11 |
| 8,652,203 B2 | 2/2014 | Quadri et al. |
| 8,747,463 B2 | 6/2014 | Fogarty et al. |
| 9,078,781 B2 | 7/2015 | Ryan et al. |
| 2001/0021872 A1 | 9/2001 | Bailey et al. |
| 2002/0026094 A1 | 2/2002 | Roth |
| 2002/0032481 A1 | 3/2002 | Gabbay |
| 2002/0116049 A1 * | 8/2002 | Girton ............... A61F 2/915 623/1.15 |
| 2002/0138135 A1 | 9/2002 | Duerig et al. |
| 2002/0143390 A1 | 10/2002 | Ishii |
| 2002/0173842 A1 | 11/2002 | Buchanan |
| 2003/0014105 A1 | 1/2003 | Cao |
| 2003/0050694 A1 | 3/2003 | Yang et al. |
| 2003/0100939 A1 | 5/2003 | Yodfat et al. |
| 2003/0158597 A1 | 8/2003 | Quiachon et al. |
| 2003/0212454 A1 | 11/2003 | Scott et al. |
| 2004/0024452 A1 | 2/2004 | Kruse et al. |
| 2004/0039436 A1 | 2/2004 | Spenser et al. |
| 2004/0078074 A1 | 4/2004 | Anderson et al. |
| 2004/0186558 A1 | 9/2004 | Pavcnik et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0010285 A1 | 1/2005 | Lambrecht et al. |
| 2005/0075725 A1 | 4/2005 | Rowe |
| 2005/0075728 A1 | 4/2005 | Nguyen et al. |
| 2005/0096736 A1 | 5/2005 | Osse et al. |
| 2005/0096738 A1 | 5/2005 | Cali et al. |
| 2005/0188525 A1 | 9/2005 | Weber et al. |
| 2005/0203614 A1 | 9/2005 | Forster et al. |
| 2005/0203617 A1 | 9/2005 | Forster et al. |
| 2005/0234546 A1 | 10/2005 | Nugent et al. |
| 2006/0004469 A1 | 1/2006 | Sokel |
| 2006/0025857 A1 | 2/2006 | Bergheim et al. |
| 2006/0058872 A1 | 3/2006 | Salahieh et al. |
| 2006/0074484 A1 | 4/2006 | Huber |
| 2006/0108090 A1 | 5/2006 | Ederer et al. |
| 2006/0149350 A1 | 7/2006 | Patel et al. |
| 2006/0183383 A1 | 8/2006 | Asmus et al. |
| 2006/0229719 A1 | 10/2006 | Marquez et al. |
| 2006/0259136 A1 | 11/2006 | Nguyen et al. |
| 2006/0259137 A1 | 11/2006 | Artof et al. |
| 2006/0287717 A1 | 12/2006 | Rowe et al. |
| 2007/0005131 A1 | 1/2007 | Taylor |
| 2007/0010876 A1 | 1/2007 | Salahieh et al. |
| 2007/0010877 A1 | 1/2007 | Salahieh et al. |
| 2007/0112422 A1 | 5/2007 | Dehdashtian |
| 2007/0162102 A1 | 7/2007 | Ryan et al. |
| 2007/0203503 A1 | 8/2007 | Salahieh et al. |
| 2007/0203575 A1 | 8/2007 | Forster et al. |
| 2007/0203576 A1 | 8/2007 | Lee et al. |
| 2007/0208550 A1 | 9/2007 | Cao et al. |
| 2007/0213813 A1 | 9/2007 | Von Segesser et al. |
| 2007/0233228 A1 | 10/2007 | Eberhardt et al. |
| 2007/0260305 A1 | 11/2007 | Drews et al. |
| 2007/0265700 A1 | 11/2007 | Eliasen et al. |
| 2008/0021546 A1 | 1/2008 | Patz et al. |
| 2008/0114442 A1 | 5/2008 | Mitchell et al. |
| 2008/0125853 A1 | 5/2008 | Bailey et al. |
| 2008/0140189 A1 * | 6/2008 | Nguyen ............... A61F 2/2418 623/2.11 |
| 2008/0154355 A1 | 6/2008 | Benichou et al. |
| 2008/0183271 A1 | 7/2008 | Frawley et al. |
| 2008/0208327 A1 | 8/2008 | Rowe |
| 2008/0243245 A1 | 10/2008 | Thambar et al. |
| 2008/0255660 A1 | 10/2008 | Guyenot et al. |
| 2008/0275537 A1 | 11/2008 | Limon |
| 2008/0294248 A1 | 11/2008 | Yang et al. |
| 2009/0118826 A1 | 5/2009 | Khaghani |
| 2009/0125118 A1 | 5/2009 | Gong |
| 2009/0157175 A1 | 6/2009 | Benichou |
| 2009/0276040 A1 | 11/2009 | Rowe et al. |
| 2009/0281619 A1 | 11/2009 | Le et al. |
| 2009/0287296 A1 | 11/2009 | Manasse |
| 2009/0287299 A1 | 11/2009 | Tabor et al. |
| 2009/0299452 A1 | 12/2009 | Eidenschink et al. |
| 2009/0319037 A1 | 12/2009 | Rowe et al. |
| 2010/0004735 A1 | 1/2010 | Yang et al. |
| 2010/0049313 A1 | 2/2010 | Alon et al. |
| 2010/0082094 A1 | 4/2010 | Quadri et al. |
| 2010/0094411 A1 * | 4/2010 | Tuval ............... A61F 2/2418 623/2.11 |
| 2010/0100176 A1 * | 4/2010 | Elizondo ............... A61F 2/2418 623/2.38 |
| 2010/0168844 A1 | 7/2010 | Toomes et al. |
| 2010/0185277 A1 | 7/2010 | Braido et al. |
| 2010/0198347 A1 | 8/2010 | Zakay et al. |
| 2010/0204781 A1 | 8/2010 | Alkhatib |
| 2011/0015729 A1 | 1/2011 | Jimenez et al. |
| 2011/0022157 A1 | 1/2011 | Essinger et al. |
| 2011/0066224 A1 | 3/2011 | White |
| 2011/0137397 A1 | 6/2011 | Chau et al. |
| 2011/0208293 A1 * | 8/2011 | Tabor ............... A61B 5/1076 623/1.26 |
| 2011/0218619 A1 | 9/2011 | Benichou et al. |
| 2011/0319991 A1 | 12/2011 | Hariton et al. |
| 2012/0078347 A1 * | 3/2012 | Braido ............... A61F 2/915 623/1.26 |
| 2012/0089223 A1 | 4/2012 | Nguyen et al. |
| 2012/0101571 A1 | 4/2012 | Thambar et al. |
| 2012/0116496 A1 * | 5/2012 | Chuter ............... A61F 2/2418 623/1.15 |
| 2012/0123529 A1 * | 5/2012 | Levi ............... A61F 2/2433 623/2.11 |
| 2012/0259409 A1 | 10/2012 | Nguyen et al. |
| 2013/0023985 A1 | 1/2013 | Khairkhahan et al. |
| 2013/0046373 A1 | 2/2013 | Cartledge et al. |
| 2013/0150956 A1 | 6/2013 | Yohanan et al. |
| 2013/0166017 A1 | 6/2013 | Cartledge et al. |
| 2013/0190857 A1 | 7/2013 | Mitra et al. |
| 2013/0274873 A1 | 10/2013 | Delaloye et al. |
| 2013/0310926 A1 | 11/2013 | Hariton |
| 2013/0317598 A1 | 11/2013 | Rowe et al. |
| 2013/0331929 A1 | 12/2013 | Mitra et al. |
| 2014/0194981 A1 | 7/2014 | Menk et al. |
| 2014/0200661 A1 | 7/2014 | Pintor et al. |
| 2014/0209238 A1 | 7/2014 | Bonyuet et al. |
| 2014/0222136 A1 | 8/2014 | Geist et al. |
| 2014/0277417 A1 | 9/2014 | Schraut et al. |
| 2014/0277419 A1 | 9/2014 | Garde et al. |
| 2014/0277424 A1 | 9/2014 | Oslund |
| 2014/0277563 A1 | 9/2014 | White |
| 2014/0296962 A1 | 10/2014 | Cartledge et al. |
| 2014/0330372 A1 | 11/2014 | Weston et al. |

(56) References Cited

U.S. PATENT DOCUMENTS

| | | | |
|---|---|---|---|
| 2014/0343670 A1 | 11/2014 | Bakis et al. | |
| 2014/0343671 A1 | 11/2014 | Yohanan et al. | |
| 2014/0350667 A1 | 11/2014 | Braido et al. | |
| 2015/0073545 A1 | 3/2015 | Braido | |
| 2015/0073546 A1 | 3/2015 | Braido | |
| 2015/0135506 A1 | 5/2015 | White | |
| 2015/0157455 A1 | 6/2015 | Hoang et al. | |
| 2015/0173898 A1* | 6/2015 | Drasler | A61F 2/2418 623/2.18 |
| 2015/0230923 A1* | 8/2015 | Levi | A61F 2/2418 623/2.36 |
| 2016/0000559 A1* | 1/2016 | Chen | A61F 2/2412 623/2.15 |
| 2016/0158004 A1* | 6/2016 | Kumar | A61F 2/2418 623/2.17 |
| 2016/0374802 A1 | 12/2016 | Levi et al. | |
| 2017/0014229 A1 | 1/2017 | Nguyen-Thien-Nhon et al. | |
| 2017/0049566 A1* | 2/2017 | Zeng | A61F 2/2412 |
| 2017/0065409 A1* | 3/2017 | Scorsin | A61F 2/2418 |
| 2017/0156839 A1* | 6/2017 | Cooper | A61F 2/2436 |
| 2018/0028310 A1 | 2/2018 | Gurovich et al. | |
| 2018/0125651 A1* | 5/2018 | Nasr | A61F 2/2412 |
| 2018/0153689 A1 | 6/2018 | Maimon et al. | |
| 2018/0325665 A1 | 11/2018 | Gurovich et al. | |
| 2018/0344456 A1 | 12/2018 | Barash et al. | |
| 2019/0046316 A1* | 2/2019 | Chen | A61F 2/2418 |
| 2019/0159894 A1 | 5/2019 | Levi et al. | |
| 2019/0192288 A1 | 6/2019 | Levi et al. | |
| 2019/0192289 A1 | 6/2019 | Levi et al. | |
| 2020/0000579 A1* | 1/2020 | Manash | A61F 2/2409 |
| 2020/0179146 A1* | 6/2020 | Christianson | A61F 2/91 |
| 2020/0188099 A1* | 6/2020 | Dvorsky | A61F 2/95 |
| 2020/0352709 A1* | 11/2020 | Gurovich | A61F 2/2418 |
| 2020/0390547 A1* | 12/2020 | Dvorsky | A61F 2/2418 |

FOREIGN PATENT DOCUMENTS

| | | |
|---|---|---|
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 A1 | 3/1984 |
| EP | 0850607 A1 | 7/1998 |
| EP | 1057460 A1 | 12/2000 |
| EP | 1088529 A2 | 4/2001 |
| EP | 1570809 A1 | 9/2005 |
| FR | 2788217 A1 | 7/2000 |
| FR | 2815844 A1 | 5/2002 |
| GB | 2056023 A | 3/1981 |
| JP | 2012101061 A | 5/2012 |
| SU | 1271508 A1 | 11/1986 |
| WO | 9117720 A1 | 11/1991 |
| WO | 9217118 A1 | 10/1992 |
| WO | 9301768 A1 | 2/1993 |
| WO | 9724080 A1 | 7/1997 |
| WO | 9829057 A1 | 7/1998 |
| WO | 9930646 A1 | 6/1999 |
| WO | 9933414 A1 | 7/1999 |
| WO | 9940964 A1 | 8/1999 |
| WO | 9947075 A1 | 9/1999 |
| WO | 0018333 A1 | 4/2000 |
| WO | 0041652 A1 | 7/2000 |
| WO | 0047139 A1 | 8/2000 |
| WO | 0135878 A2 | 5/2001 |
| WO | 0149213 A2 | 7/2001 |
| WO | 0154624 A1 | 8/2001 |
| WO | 0154625 A1 | 8/2001 |
| WO | 0162189 A1 | 8/2001 |
| WO | 0164137 A1 | 9/2001 |
| WO | 0176510 A2 | 10/2001 |
| WO | 0222054 A1 | 3/2002 |
| WO | 0236048 A1 | 5/2002 |
| WO | 0241789 A2 | 5/2002 |
| WO | 0243620 A1 | 6/2002 |
| WO | 0247575 A2 | 6/2002 |
| WO | 0249540 A2 | 6/2002 |
| WO | 03047468 A1 | 6/2003 |
| WO | 2004096100 A1 | 11/2004 |
| WO | 2005034812 A1 | 4/2005 |
| WO | 2005055883 A1 | 6/2005 |
| WO | 2005084595 A1 | 9/2005 |
| WO | 2006014233 A2 | 2/2006 |
| WO | 2006032051 A2 | 3/2006 |
| WO | 2006034008 A2 | 3/2006 |
| WO | 2006111391 A1 | 10/2006 |
| WO | 2006127089 A1 | 11/2006 |
| WO | 2006138173 A2 | 12/2006 |
| WO | 2005102015 A3 | 4/2007 |
| WO | 2007047488 A2 | 4/2007 |
| WO | 2007067942 A1 | 6/2007 |
| WO | 2007097983 A2 | 8/2007 |
| WO | 2007130537 A1 | 11/2007 |
| WO | 2008005405 A2 | 1/2008 |
| WO | 2008015257 A2 | 2/2008 |
| WO | 2008035337 A2 | 3/2008 |
| WO | 2008091515 A2 | 7/2008 |
| WO | 2008147964 A1 | 12/2008 |
| WO | 2008150529 A1 | 12/2008 |
| WO | 2009033469 A1 | 3/2009 |
| WO | 2009042196 A2 | 4/2009 |
| WO | 2009053497 A1 | 4/2009 |
| WO | 2009061389 A2 | 5/2009 |
| WO | 2009094188 A2 | 7/2009 |
| WO | 2009116041 A2 | 9/2009 |
| WO | 2009149462 A2 | 12/2009 |
| WO | 2010011699 A2 | 1/2010 |
| WO | 2010121076 A2 | 10/2010 |
| WO | 2012048035 A2 | 4/2012 |
| WO | 2013106585 A1 | 7/2013 |
| WO | 2015085218 A1 | 6/2015 |

OTHER PUBLICATIONS

H.R. Andersen "History of Percutaneous Aortic Valve Prosthesis," Herz No. 34. pp. 343-346. 2009.

Pavcnik, et al. "Development and initial Experimental Evaluation of a Prosthetic Aortic Valve for Transcatheter Placement," Cardiovascular Radiology, vol. 183, No. 1. pp. 151-154. 1992.

Bailey, S. "Percutaneous Expandable Prosthetic Valves," Textbook of Interventional Cardiology vol. 2, 2nd Ed. pp. 1268-1276. 1994.

Al-Khaja, et al. "Eleven Years' Experience with Carpentier-Edwards Biological Valves in Relation to Survival and Complications," European Journal of Cardiothoracic Surgery, vol. 3. pp. 305-311. 1989.

Ross, "Aortic Valve Surgery," At a meeting of the Council on Aug. 4, 1966. pp. 192-197.

Sabbah, et al. "Mechanical Factors in the Degeneration of Porcine Bioprosthetic Valves: An Overview," Journal of Cardiac Surgery, vol. 4, No. 4. pp. 302-309. 1989.

Wheatley, "Valve Prostheses," Operative Surgery, 4th ed. pp. 415-424. 1986.

Uchida, "Modifications of Gianturco Expandable Wire Stents," American Journal of Roentgenology, vol. 150. pp. 1185-1187. 1986.

Walther T, Dehdashtian MM, Khanna R, Young E, Goldbrunner PJ, Lee W. Trans-catheter valve-in-valve implantation: In vitro hydrodynamic performance of the SAPIEN+cloth trans-catheter heart valve in the Carpentier-Edwards Perimount valves. Eur J Cardiothorac Surg. 2011;40(5):1120-6. Epub Apr. 7, 2011.

Fontaine, M.D., Arthur B., et al., "Vascular Stent Prototype; Results of Preclinical Evaluation", p. 29-34; Technical Developments and Instrumentation; Jan.-Feb. 1996, vol. 7, No. 1.

(56) References Cited

OTHER PUBLICATIONS

Fontaine, M.D., Arthur B., et al., "Prototype Stent: Invivo Swine Studies in the Biliary System1", p. 101-105, Journal of Vascular and Interventional Radiology; Jan.-Feb. 1997; vol. 8, No. 1.

* cited by examiner

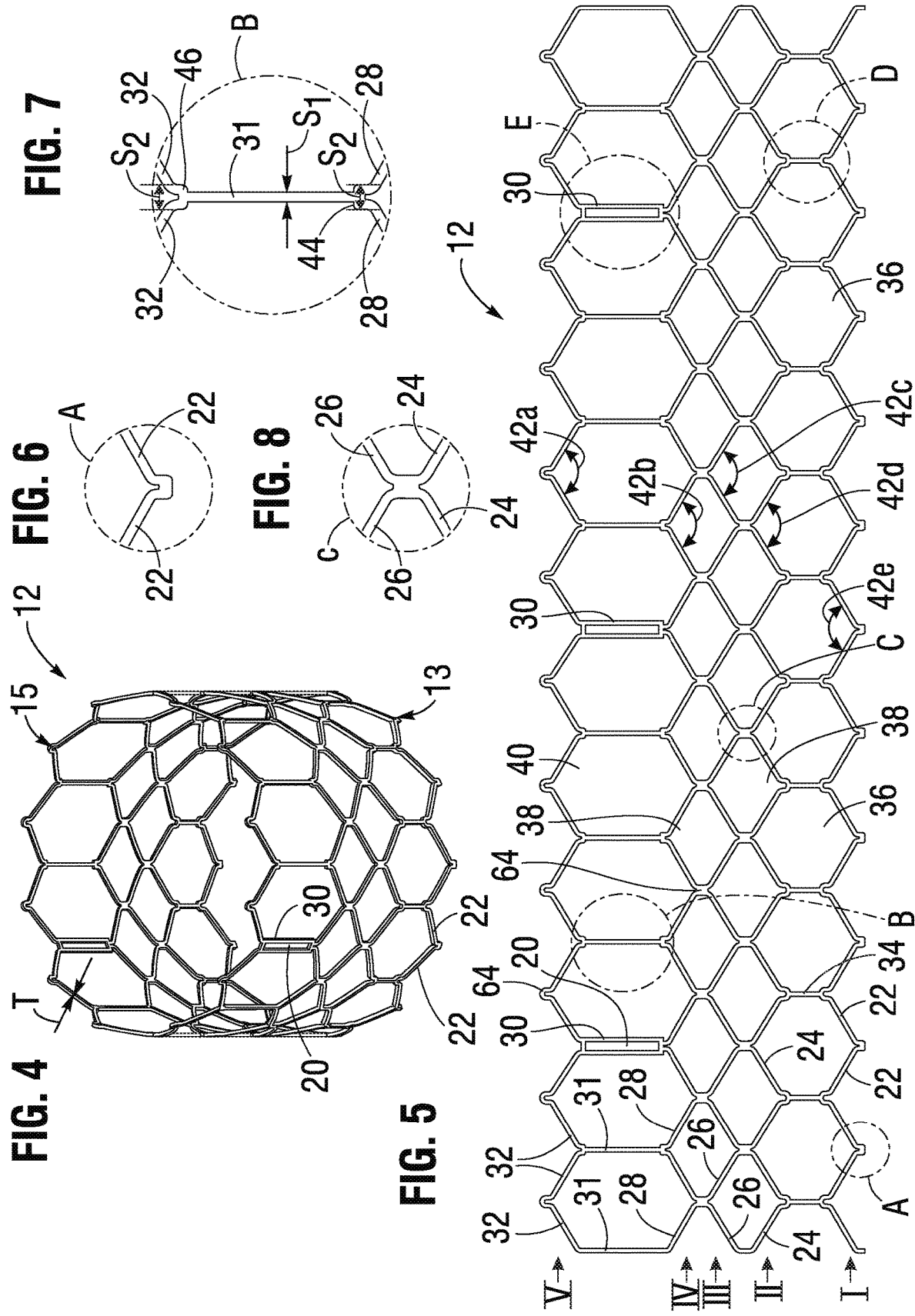

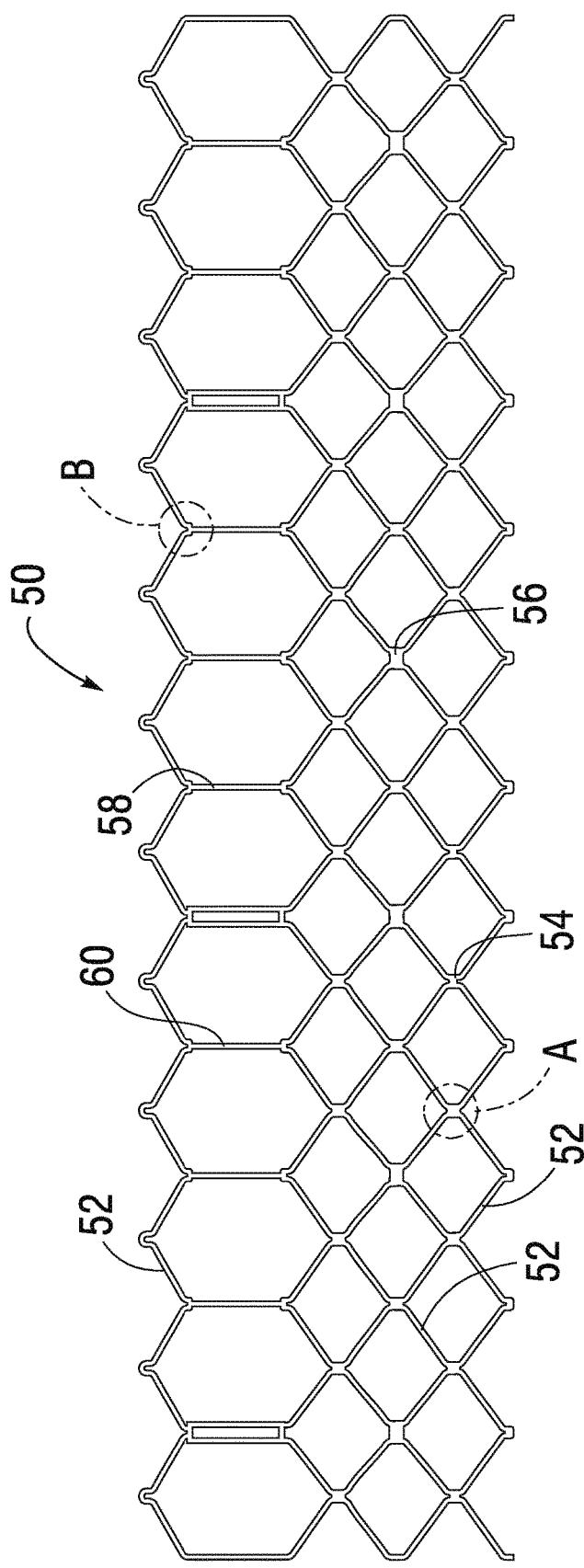
FIG. 12
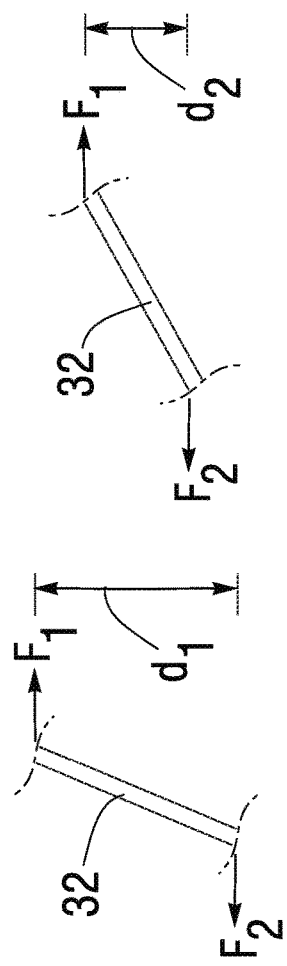
FIG. 15A
FIG. 15B
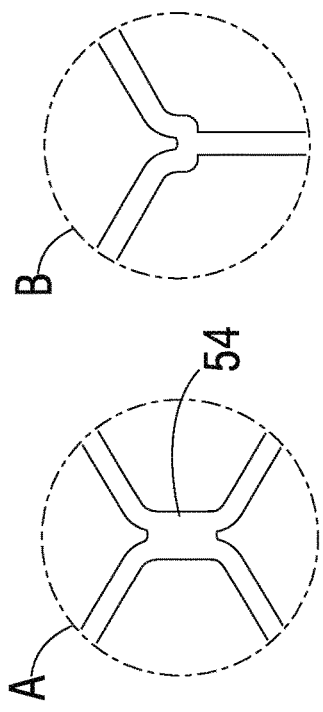
FIG. 13
FIG. 14

| | Deployment Range | |
|---|---|---|
| Inflow Portion 834: 20.5mm  21.5mm | | 23.5mm 24mm |
| Outflow Portion 836: 22.5mm  23.5mm | | 23.5mm 24mm |
| | Y - Shape | Parallel-Shape |

FRAME FOR PROSTHETIC HEART VALVE

CROSS REFERENCE TO RELATED APPLICATIONS

The present application is a continuation of PCT Application No. PCT/US2020/013725, filed Jan. 15, 2020, which claims the benefit of U.S. Provisional Application No. 62/793,692, filed Jan. 17, 2019, and U.S. Provisional Application No. 62/858,249, filed Jun. 6, 2019. The entire disclosures of PCT Application No. PCT/US2020/013725, U.S. Provisional Application No. 62/793,692 and U.S. Provisional Application No. 62/858,249 are incorporated herein by reference.

FIELD

The present application relates to prosthetic heart valves including frames that are configured to be manufactured in a cylindrical shape, crimped onto a delivery apparatus, and expanded to any of a variety of non-cylindrical shapes without the use of shaped expansion devices.

BACKGROUND

The human heart can suffer from various valvular diseases. These valvular diseases can result in significant malfunctioning of the heart and ultimately require replacement of the native valve with an artificial valve. There are a number of known artificial valves and a number of known methods of implanting these artificial valves in humans.

Various surgical techniques may be used to replace or repair a diseased or damaged valve. Due to stenosis and other heart valve diseases, thousands of patients undergo surgery each year wherein the defective native heart valve is replaced by a prosthetic valve. Another less drastic method for treating defective valves is through repair or reconstruction, which is typically used on minimally calcified valves. The problem with surgical therapy is the significant risk it imposes on these chronically ill patients with high morbidity and mortality rates associated with surgical repair.

When the native valve is replaced, surgical implantation of the prosthetic valve typically requires an open-chest surgery during which the heart is stopped and patient placed on cardiopulmonary bypass (a so-called "heart-lung machine"). In one common surgical procedure, the diseased native valve leaflets are excised and a prosthetic valve is sutured to the surrounding tissue at the valve annulus. Because of the trauma associated with the procedure and the attendant duration of extracorporeal blood circulation, some patients do not survive the surgical procedure or die shortly thereafter. It is well known that the risk to the patient increases with the amount of time required on extracorporeal circulation. Due to these risks, a substantial number of patients with defective native valves are deemed inoperable because their condition is too frail to withstand the procedure. By some estimates, more than 50% of the subjects suffering from valve stenosis who are older than 80 years cannot be operated on for valve replacement.

Because of the drawbacks associated with conventional open-heart surgery, percutaneous and minimally-invasive surgical approaches are garnering intense attention. In one technique, a prosthetic valve is configured to be implanted in a much less invasive procedure by way of catheterization. For instance, U.S. Pat. Nos. 5,411,522 and 6,730,118, which are incorporated herein by reference, describe collapsible transcatheter heart valves that can be percutaneously introduced in a compressed state on a catheter and expanded in the desired position by balloon inflation or by utilization of a self-expanding frame or stent.

An important design parameter of a transcatheter heart valve is the shape or profile of the expanded prosthetic valve. The deployed shape of the prosthetic valve is important because it can affect how the prosthetic valve anchors or interfaces with the native valve annulus, the proportions of the prosthetic valve that are located in one chamber versus the other chamber across the native valve, and/or the location(s) where the prosthetic valve engages the native tissue. The shape of the expanded prosthetic valve can also affect various hemodynamic parameters of the prosthetic valve, such as the pressure drop across the prosthetic valve, the orifice area at the inflow and outflow, and the degree to which the leaflets open and close during valve operation.

SUMMARY

Certain embodiments of the disclosure are directed to frames for prosthetic heart valves that are configured to be manufactured in a cylindrical shape, radially collapsed onto a cylindrical balloon or other expansion device, and expanded to a non-cylindrical shape using the cylindrical balloon. In one representative embodiment, a prosthetic heart valve comprises a frame including an inflow end, an outflow end, and a central portion between the inflow end and the outflow end. The frame is radially collapsible and expandable from a collapsed configuration to an expanded configuration. The inflow end comprises a plurality of circumferentially extending first strut members having a first strut width and forming a first angle between adjacent first strut members, and the central portion comprises a plurality of circumferentially extending second strut members having a second strut width and forming a second angle between adjacent second strut members. The prosthetic heart valve further comprises a plurality of leaflets positioned at least partially within the frame and configured to regulate a flow of blood through the prosthetic heart valve. At least one of the first angle and the second angle, or the first strut width and the second strut width, are different such that when the prosthetic heart valve is crimped onto a cylindrical balloon and expanded to the expanded configuration using the cylindrical balloon, a diameter of the outflow end of the frame is different from a diameter of the central portion of the frame.

In some embodiments, the first angle is greater than the second angle and the first strut width is equal to the second strut width such that the diameter of the outflow end is greater than the diameter of the central portion when the prosthetic heart valve is expanded to the expanded configuration.

In some embodiments, a diameter of the inflow end is substantially equal to the diameter of the central portion such that the frame has a Y-shaped profile when expanded to the expanded configuration.

In some embodiments, the outflow end of the frame comprises a plurality of circumferentially extending third strut members, the third strut members having a third strut width and forming a third angle between adjacent third strut members. The third strut width is equal to the first and second strut widths, and the third angle is less than the first angle and less than the second angle such that the frame has a Y-shaped profile when expanded to the expanded configuration.

In some embodiments, the diameter of the inflow end and the diameter of the outflow end are greater than the diameter of the central portion of the frame when the frame is between the collapsed configuration and the expanded configuration such that the frame has an hourglass-shaped profile.

In some embodiments, the prosthetic heart valve comprises five rows of strut members.

In some embodiments, the central portion comprises three rows of strut members between the inflow end and the outflow end, the three rows of strut members including the plurality of second strut members.

In some embodiments, the strut members of each of the three rows of strut members of the central portion comprise the second strut width and the second angle between adjacent strut members.

In some embodiments, the first angle is 110° to 170°.

In some embodiments, the second angle is 80° to 130°.

In some embodiments, the third angle is 60° to 120°.

In some embodiments, the first strut width, the second strut width, and the third strut width are from 0.1 mm to 0.8 mm.

In some embodiments, the first strut width, the second strut width, and the third strut width are from 0.2 mm to 0.6 mm.

In some embodiments, the diameter of the outflow end is less than the diameter of the central portion of the frame when the frame is expanded to the expanded configuration.

In some embodiments, the first angle is greater than the second angle, and the first strut width is substantially equal to the second strut width such that the diameter of the central portion of the frame is greater than a diameter of the inflow end and greater than the diameter of the outflow end such that the frame has a barrel-shaped profile when expanded to the expanded configuration.

In some embodiments, the diameter of the inflow end and the diameter of the outflow end are greater than the diameter of the central portion when the frame is between the collapsed configuration and the expanded configuration such that the frame has an hourglass-shaped profile.

In some embodiments, an exterior surface of the frame comprises a convex profile.

In some embodiments, the convex profile of the frame defines an apex at the central portion of the frame.

In some embodiments, the prosthetic heart valve comprises five rows of strut members, and the apex is located along a row of strut members that is third from the inflow end.

In some embodiments, the outflow end comprises a plurality of circumferentially-extending third strut members, the third strut members having a third strut width and forming a third angle between adjacent third strut members, and the third strut width is substantially equal to the first strut width.

In some embodiments, the third angle is substantially equal to the first angle.

In some embodiments, the first angle is 100° to 150°.

In some embodiments, the second angle is 60° to 100°.

In some embodiments, the first strut width and the second strut width are from 0.1 mm to 0.8 mm.

In some embodiments, the first strut width and the second strut width are from 0.2 mm to 0.6 mm.

In some embodiments, the frame is configured such that when the frame is between the collapsed configuration and the expanded configuration, the diameter of the inflow end is greater than the diameter of the central portion, and the diameter of the central portion is greater than the diameter of the outflow end.

In some embodiments, the outflow end of the frame comprises a plurality of circumferentially extending third strut members, the third strut members having a third strut width and forming a third angle between adjacent third strut members. The first angle and the third angle are substantially equal, and the third strut width is greater than the first strut width such that the frame has a barrel-shaped profile when expanded to the expanded configuration.

In some embodiments, the first angle is greater than the second angle.

In some embodiments, the prosthetic heart valve comprises five rows of strut members.

In some embodiments, the central portion comprises three rows of strut members between the inflow end and the outflow end, the three rows of strut members including the plurality of second strut members.

In some embodiments, the strut members of each of the three rows of strut members of the central portion comprise the second strut width and the second angle between adjacent strut members, and the second strut width is substantially equal to the first strut width.

In some embodiments, the first angle and the third angle are substantially equal and the third strut width is greater than the first strut width such that when the frame is between the collapsed configuration and the expanded configuration, the diameter of the inflow end is greater than the diameter of the central portion, and the diameter of the central portion is greater than the diameter of the outflow end such that the frame has frustoconical profile.

In some embodiments, the third strut width is 5% to 30% larger than the first strut width.

In some embodiments, the frame comprises a plastically-expandable material.

In some embodiments, the frame comprises stainless steel, a cobalt-chromium alloy, a nickel-cobalt-chromium alloy, or any combination thereof.

In some embodiments, the diameter of the inflow end and the diameter of the outflow end are greater than the diameter of the central portion of the frame when the frame is between the collapsed configuration and the expanded configuration such that the frame has an hourglass-shaped profile.

In some embodiments, the first angle and the second angle are equal.

In some embodiments, the first strut width is greater than the second strut width.

In some embodiments, the second strut width is greater than the first strut width.

In some embodiments, the frame is configured such that when the frame is between the collapsed configuration and the expanded configuration, a diameter of the inflow end is greater than the diameter of the central portion, and the diameter of the central portion is greater than the diameter of the outflow end.

In some embodiments, the first angle is greater than the second angle, and the first strut width is equal to the second strut width.

In some embodiments, the frame is configured such that when the prosthetic heart valve is expanded to the expanded configuration, the diameter of the outflow end of the frame is greater than the diameter of the central portion of the frame, and the diameter of the central portion of the frame is greater than a diameter of the inflow end of the frame.

In some embodiments, when the frame is between the expanded configuration and the collapsed configuration, the frame comprises an hourglass-shaped profile.

In some embodiments, the second angle is greater than the first angle.

In some embodiments, the frame is configured such that when the prosthetic heart valve is expanded to the expanded configuration, the diameter of the outflow end of the frame is less than the diameter of the central portion of the frame, and the diameter of the central portion of the frame is less than a diameter of the inflow end of the frame.

In some embodiments, when the frame is between the expanded configuration and the collapsed configuration, the frame comprises an hourglass-shaped profile.

In some embodiments, the second thickness is greater than the first thickness such that the frame has a frustoconical profile when expanded to the expanded configuration.

In some embodiments, the frame has a frustoconical profile when the frame is between the collapsed configuration and the expanded configuration.

In some embodiments, the first angle is greater than the second angle, and the first strut width is greater than the second strut width such that the frame has an inverted frustoconical profile when expanded to the expanded configuration.

In some embodiments, the frame has an inverted frustoconical profile when the frame is between the collapsed configuration and the expanded configuration.

In some embodiments, the central portion of the frame comprises a plurality of third strut members having the second strut width and forming a third angle between adjacent third strut members, and the first angle is greater than the second angle, and the second angle is greater than the third angle such that the frame comprises a Y-shaped profile when expanded to the expanded configuration.

In some embodiments, the first strut width is greater than the second strut width.

In some embodiments, the frame has an inverted frustoconical profile between the collapsed configuration and the expanded configuration.

In another representative embodiment, a prosthetic heart valve comprises a frame including an inflow end, an outflow end, and a central portion between the inflow end and the outflow end. The frame is radially collapsible and expandable from a collapsed configuration to an expanded configuration. The inflow end comprises a plurality of circumferentially extending first strut members having a first strut width and forming a first angle between adjacent first strut members, and the outflow end comprises a plurality of circumferentially extending second strut members having a second strut width and forming a second angle between adjacent second strut members. A plurality of leaflets are positioned at least partially within the frame and configured to regulate a flow of blood through the prosthetic heart valve. At least one of the first angle and the second angle, or the first strut width and the second strut width, are different such that when the prosthetic heart valve is crimped onto a cylindrical balloon and expanded to the expanded configuration using the cylindrical balloon, a diameter of the outflow end of the frame is different from a diameter of the central portion of the frame.

In some embodiments, the first angle is greater than the second angle and the first strut width is equal to the second strut width such that the diameter of the outflow end is greater than the diameter of the central portion when the prosthetic heart valve is expanded to the expanded configuration.

In some embodiments, a diameter of the inflow end is substantially equal to the diameter of the central portion such that the frame has a Y-shaped profile when expanded to the expanded configuration.

In some embodiments, the central portion of the frame comprises a plurality of circumferentially extending third strut members, and the third strut member have a third strut width and form a third angle between adjacent third strut members. The third strut width is equal to the first and second strut widths, and the third angle is less than the first angle and greater than the second angle such that the frame has a Y-shaped profile when expanded to the expanded configuration.

In some embodiments, the diameter of the inflow end and the diameter of the outflow end are greater than the diameter of the central portion of the frame when the frame is between the collapsed configuration and the expanded configuration such that the frame has an hourglass-shaped profile.

In some embodiments, the frame is configured such that when the frame is between the collapsed configuration and the expanded configuration, a diameter of the inflow end is greater than the diameter of the central portion, and the diameter of the central portion is greater than the diameter of the outflow end.

In another representative embodiment, a prosthetic heart valve comprises a frame including an inflow end, an outflow end, and a central portion between the inflow end and the outflow end. The frame is radially collapsible and expandable between a collapsed configuration and an expanded configuration. The inflow end comprises a plurality of circumferentially extending first strut members having a first strut width and forming a first angle between adjacent first strut members, and the central portion comprises a plurality of circumferentially extending second strut members having a second strut width and forming a second angle between adjacent second strut members. A plurality of leaflets is positioned at least partially within the frame and configured to regulate a flow of blood through the prosthetic heart valve. At least one of the first angle and the second angle, or the first strut width and the second strut width, are different such that when the prosthetic heart valve is crimped onto a cylindrical balloon and expanded to the expanded configuration using the cylindrical balloon, a diameter of the outflow end of the frame is greater than a diameter of the central portion of the frame between the collapsed configuration and the expanded configuration, and the diameter of the central portion of the frame is substantially equal to the diameter of the outflow end of the frame when the frame reaches the expanded configuration.

In some embodiments, the first strut width is greater than the second strut width, and the first angle is greater than the second angle.

In some embodiments, the outflow end comprises a plurality of circumferentially-extending third strut members, the third strut members having a third strut width and forming a third angle between adjacent third strut members. The third strut width is less than the first strut width and less than the second strut width, and the third angle is less than the first angle and less that the second angle.

In some embodiments, the diameter of the outflow end of the frame when the frame is in the expanded configuration is a specified design diameter, and the plurality of leaflets are configured to coapt to regulate blood flow through the prosthetic heart valve when the outflow end is at the specified design diameter and the diameter of the central portion of the frame is less than the specified design diameter.

In some embodiments, the outflow end of the frame comprises a plurality of circumferentially extending third strut members, the third strut members having a third strut width and forming a third angle between adjacent third strut members, the first strut width and the third strut width are greater than the second strut width, and when the prosthetic heart valve is expanded to the expanded configuration, the first angle between adjacent first strut members at the inflow end of the frame is substantially equal to 180 degrees, and the third angle between adjacent third strut members at the outflow end of the frame is substantially equal to 180 degrees.

In some embodiments, when the frame is in the expanded configuration, a diameter of the central portion is greater than a diameter of the inflow end and greater than a diameter of the outflow end such that the frame has a barrel-shaped profile.

In another representative embodiment, a prosthetic heart valve comprises a frame including an inflow end, an outflow end, and a central portion between the inflow end and the outflow end, the frame being radially collapsible and expandable from a collapsed configuration to an expanded configuration, the inflow end comprising a plurality of circumferentially extending first strut members having a first strut width and forming a first angle between adjacent first strut members, the central portion comprising a plurality of circumferentially extending second strut members having a second strut width and forming a second angle between adjacent second strut members. The prosthetic heart valve further comprises a plurality of leaflets positioned at least partially within the frame and configured to regulate a flow of blood through the prosthetic heart valve. The first angle and the second angle are different such that when the prosthetic heart valve is crimped onto a cylindrical balloon and expanded to the expanded configuration using the cylindrical balloon, a diameter of the outflow end of the frame is different from a diameter of the central portion of the frame.

In another representative embodiment, a prosthetic heart valve comprises a frame including an inflow end, an outflow end, and a central portion between the inflow end and the outflow end, the frame being radially collapsible and expandable from a collapsed configuration to an expanded configuration, the inflow end comprising a plurality of circumferentially extending first strut members having a first strut width and forming a first angle between adjacent first strut members, the central portion comprising a plurality of circumferentially extending second strut members having a second strut width and forming a second angle between adjacent second strut members. A plurality of leaflets are positioned at least partially within the frame and configured to regulate a flow of blood through the prosthetic heart valve. The first strut width and the second strut width are different such that when the prosthetic heart valve is crimped onto a cylindrical balloon and expanded to the expanded configuration using the cylindrical balloon, a diameter of the outflow end of the frame is different from a diameter of the central portion of the frame.

In another representative embodiment, a prosthetic heart valve comprises a frame including an inflow end, an outflow end, and a central portion between the inflow end and the outflow end, the frame being radially collapsible and expandable from a collapsed configuration to an expanded configuration, the inflow end comprising a plurality of circumferentially extending first strut members having a first strut width and forming a first angle between adjacent first strut members, the central portion comprising a plurality of circumferentially extending second strut members having a second strut width and forming a second angle between adjacent second strut members. A plurality of leaflets are positioned at least partially within the frame and configured to regulate a flow of blood through the prosthetic heart valve. At least one of the first angle and the second angle, or the first strut width and the second strut width, are different such that when the prosthetic heart valve is crimped onto a cylindrical balloon and expanded to the expanded configuration using the cylindrical balloon, the frame expands to a non-cylindrical shape.

The foregoing and other objects, features, and advantages of the disclosed technology will become more apparent from the following detailed description, which proceeds with reference to the accompanying figures.

BRIEF DESCRIPTION OF THE DRAWINGS

FIGS. 4-10 illustrate an exemplary frame of the heart valve of FIG. 1.

FIGS. 11-15B illustrate another embodiment of a frame for use with a prosthetic heart valve.

DETAILED DESCRIPTION

Figure 1:
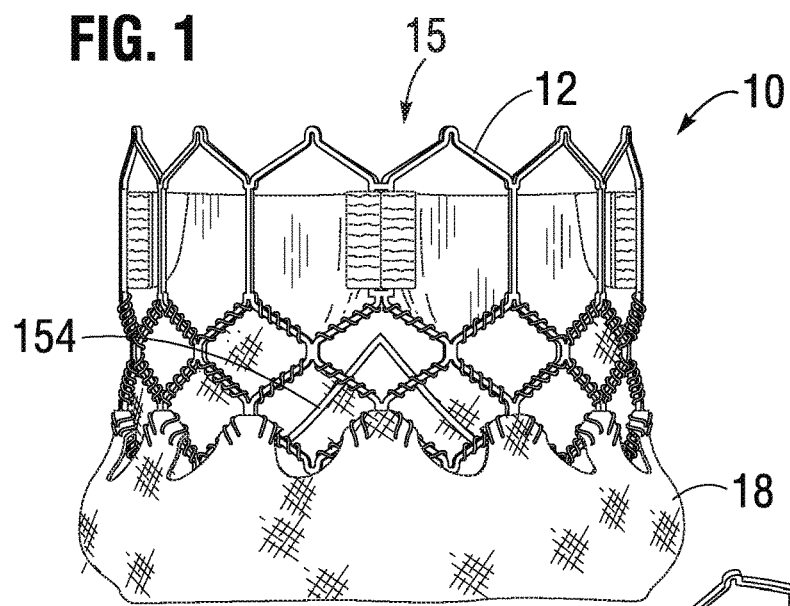
FIGS. 1-3 illustrate an exemplary embodiment of a prosthetic heart valve.

The present disclosure concerns embodiments of implantable prosthetic devices and, in particular, implantable prosthetic valves, and methods for making such devices. In particular embodiments, the prosthetic device comprises a prosthetic heart valve, and can be configured to be implanted in any of the native heart valves (aortic, mitral, pulmonary, and tricuspid). In addition, the prosthetic heart valve can be, for example, a transcatheter heart valve, a surgical heart valve, or a minimally-invasive heart valve. The prosthetic valve also can comprise other types of valves implantable within other body lumens outside of the heart or heart valves that are implantable within the heart at locations other than the native valves, such as trans-atrial or trans-ventricle septum valves.

The disclosed prosthetic heart valves are particularly suited for implantation in the native aortic valve. In the context of a prosthetic aortic valve, the terms "lower" and "upper" are used interchangeably with the terms "inflow" and "outflow", respectively, for convenience. Thus, for example, the lower end of the prosthetic valve is its inflow end and the upper end of the prosthetic valve is its outflow end in the orientation shown in the drawings. However, it should be understood that the prosthetic valve can be implanted in the reverse orientation. For example, for implantation at the mitral valve position, the upper end of the prosthetic valve is the inflow end and the lower end of the valve is the outflow end.

Particular embodiments of the application are directed to frames for prosthetic heart valves that are manufactured in a cylindrical shape, and are configured to be crimped to a smaller diameter around a cylindrical balloon on the distal end of a balloon catheter of a delivery apparatus. Certain parameters of the frame, such as the angle between struts at various locations along the frame height and/or the thickness of the struts as measured between inflow-oriented and outflow-oriented surfaces of the struts (referred to herein as the "strut width") can be configured such that when the prosthetic valve is expanded, the frame expands to a non-cylindrical shape on the cylindrical balloon.

For example, the frames described herein can be configured to form a Y-shape, an hourglass shape, a V-shape, an A-shape or frustoconical shape, etc., during expansion (e.g., when the frame is between the collapsed configuration and the fully expanded configuration). The frames can be further configured to form a barrel shape, a Y-shape, a V-shape, an A-shape, and/or a cylindrical shape when fully expanded to their specified design diameter. Selection of a frame configured to form a particular shape can allow a physician to balance shape-dependent considerations including anchoring of the prosthetic valve in the native anatomy, the pressure gradient across the prosthetic valve, contact and/or pressure applied by the prosthetic valve to the native anatomy, and/or the proximity of the prosthetic valve to sensitive anatomical structures such as the His bundle.

Certain frame embodiments described herein are also configured to be implantable at various stages of expansion, and having various cylindrical or non-cylindrical shapes. For example, frame embodiments described herein can be operable throughout a range of diameters, also referred to as a "deployment range," in which the leaflets of the prosthetic valve can function to regulate blood flow through the valve. Different portions of the frame can be configured to expand at different rates such that the frame may comprise various shapes throughout the deployment range, and various portions of the frame may have different diameters. This can allow a physician to adjust the shape of the frame and/or the diameter of various portions of the frame during deployment.

Figure 2:
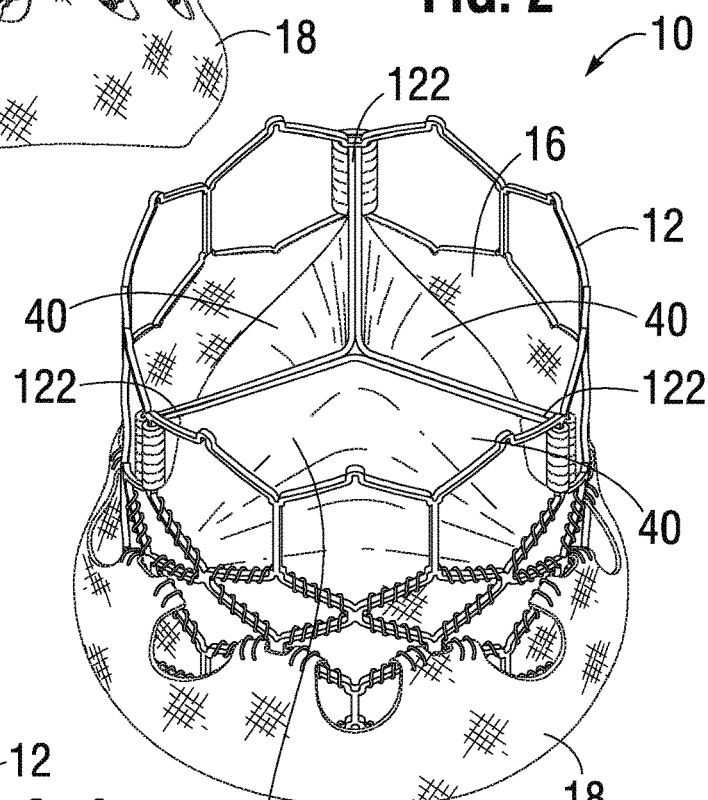
Figure 3:
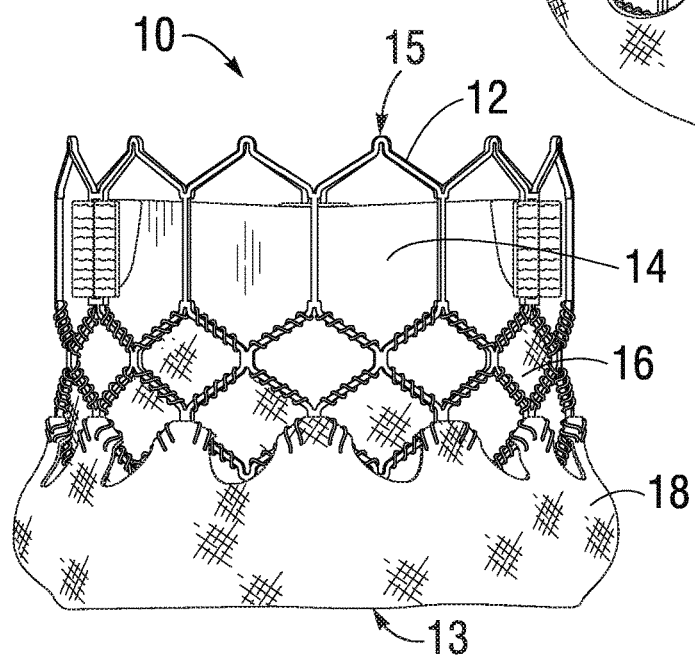
Figure 9:
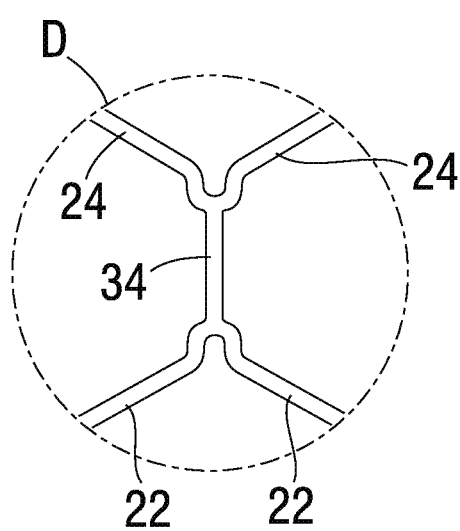
Figure 10:
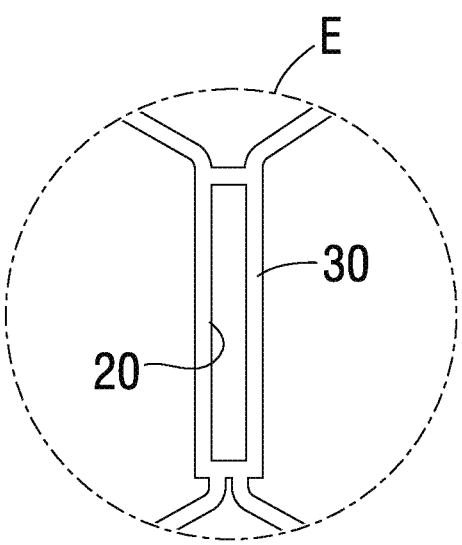

FIGS. 1-3 show various views of a prosthetic heart valve 10 configured as the Edwards Lifesciences SAPIEN® 3 prosthetic heart valve, according to one embodiment. The illustrated valve is adapted to be implanted in the native aortic annulus, although in other embodiments it can be adapted to be implanted in the other native annuluses of the heart. The valve 10 can have four main components: a stent, or frame, 12, a valvular structure 14, an inner skirt 16, and an outer skirt 18.

The valvular structure 14 can comprise three leaflets 40, collectively forming a leaflet structure, which can be arranged to collapse in a tricuspid arrangement including commissures 122, as best shown in FIG. 2. The lower edge of leaflet structure 14 desirably has an undulating, curved scalloped shape (suture line 154 shown in FIG. 1 tracks the scalloped shape of the leaflet structure). By forming the leaflets with this scalloped geometry, stresses on the leaflets are reduced which, in turn, improves durability of the valve. Moreover, by virtue of the scalloped shape, folds and ripples at the belly of each leaflet (the central region of each leaflet), which can cause early calcification in those areas, can be eliminated or at least minimized. The scalloped geometry also reduces the amount of tissue material used to form leaflet structure, thereby allowing a smaller, more even crimped profile at the inflow end of the valve. The leaflets 40 can be formed of pericardial tissue (e.g., bovine pericardial tissue), biocompatible synthetic materials, or various other suitable natural or synthetic materials as known in the art and described in U.S. Pat. No. 6,730,118, which is incorporated by reference herein.

The bare frame 12 is shown in FIG. 4. The frame 12 can be formed with a plurality of circumferentially spaced slots, or commissure windows, 20 (three in the illustrated embodiment) that are adapted to mount the commissures of the valvular structure 14 to the frame, as described in greater detail below. The frame 12 can be made of any of various suitable plastically-expandable materials (e.g., stainless steel, etc.) or self-expanding materials (e.g., Nitinol) as known in the art. When constructed of a plastically-expandable material, the frame 12 (and thus the valve 10) can be crimped to a radially compressed state on a delivery catheter and then expanded inside a patient by an inflatable balloon or equivalent expansion mechanism. When constructed of a self-expandable material, the frame 12 (and thus the valve 10) can be crimped to a radially compressed state and restrained in the compressed state by insertion into a sheath or equivalent mechanism of a delivery catheter. Once inside the body, the valve can be advanced from the delivery sheath, which allows the valve to expand to its functional size.

Suitable plastically-expandable materials that can be used to form the frame 12 include, without limitation, stainless steel, a nickel based alloy (e.g., a cobalt-chromium or a nickel-cobalt-chromium alloy), polymers, or combinations thereof. In particular embodiments, frame 12 is made of a nickel-cobalt-chromium-molybdenum alloy, such as MP35N™ (tradename of SPS Technologies), which is equivalent to UNS R30035 (covered by ASTM F562-02). MP35N™/UNS R30035 comprises 35% nickel, 35% cobalt, 20% chromium, and 10% molybdenum, by weight. It has been found that the use of MP35N to form frame 12 provides superior structural results over stainless steel. In particular, when MP35N is used as the frame material, less material is needed to achieve the same or better performance in radial and crush force resistance, fatigue resistances, and corrosion resistance. Moreover, since less material is required, the crimped profile of the frame can be reduced, thereby providing a lower profile valve assembly for percutaneous delivery to the treatment location in the body.

Referring to FIGS. 4 and 5, the frame 12 in the illustrated embodiment comprises a first, lower row I of angled struts 22 arranged end-to-end and extending circumferentially at the inflow end 13 of the frame; a second row II of circumferentially extending, angled struts 24; a third row III of circumferentially extending, angled struts 26; a fourth row IV of circumferentially extending, angled struts 28; and a fifth row V of circumferentially extending, angled struts 32 at the outflow end 15 of the frame. A plurality of substantially straight axially extending struts 34 (FIG. 5) can be used to interconnect the struts 22 of the first row I with the struts 24 of the second row II. The fifth row V of angled struts 32 are connected to the fourth row IV of angled struts 28 by a plurality of axially extending window frame portions 30 (which define the commissure windows 20) and a plurality of axially extending struts 31. Each axial strut 31 and each frame portion 30 extends from a location defined by the convergence of the lower ends of two angled struts 32 to another location defined by the convergence of the upper ends of two angled struts 28. FIGS. 6, 7, 8, 9 and 10 are enlarged views of the portions of the frame 12 identified by letters A, B, C, D and E, respectively, in FIG. 4.

Each commissure window frame portion 30 mounts a respective commissure of the leaflet structure 14. As can be seen each frame portion 30 is secured at its upper and lower ends to the adjacent rows of struts to provide a robust configuration that enhances fatigue resistance under cyclic loading of the valve compared to known cantilevered struts for supporting the commissures of the leaflet structure. This configuration enables a reduction in the frame wall thickness to achieve a smaller crimped diameter of the valve. In particular embodiments, the thickness T of the frame 12 (FIG. 4) measured between the inner diameter and outer diameter is about 0.55 mm, or about 0.48 mm or less.

The struts and frame portions of the frame collectively define a plurality of open cells of the frame. At the inflow end of the frame 12, struts 22, struts 24, and struts 34 define a lower row of cells defining openings 36. The second, third, and fourth rows of struts 24, 26, and 28 define two intermediate rows of cells defining openings 38. The fourth and fifth rows of struts 28 and 32, along with frame portions 30 and struts 31, define an upper row of cells defining openings 41. The openings 41 are relatively large and are sized to allow portions of the leaflet structure 14 to protrude, or bulge, into and/or through the openings 41 when the frame 12 is crimped in order to minimize the crimping profile.

As best shown in FIG. 7, the lower end of the strut 31 is connected to two struts 28 at a node or junction 44, and the upper end of the strut 31 is connected to two struts 32 at a node or junction 46. The strut 31 can have a thickness S1 that is less than the thicknesses S2 of the junctions 44, 46. The junctions 44, 46, along with junctions 64, can prevent full closure of openings 41. The geometry of the struts 31, and junctions 44, 46 and 64 can assist in creating enough space in openings 41 in the crimped state to allow portions of the leaflets to protrude (e.g., bulge) outwardly through openings. This allows the valve to be crimped to a relatively smaller diameter than if all of the leaflet material is constrained within the crimped frame.

The frame 12 is configured to prevent or at least minimize possible over-expansion of the valve at a predetermined balloon pressure, especially at the outflow end portion of the frame, which supports the leaflet structure 14. In one aspect, the frame is configured to have relatively larger angles 42a, 42b, 42c, 42d, 42e between struts. The larger the angle, the greater the force required to open (expand) the frame. This phenomenon is schematically illustrated in FIGS. 15A and 15B. FIG. 15A shows a strut 32 when the frame 12 is in its compressed state (e.g., mounted on a balloon). The vertical distance $d_1$ between the ends of the struts is greatest when the frame is compressed, providing a relatively large moment between forces $F_1$ and $F_2$ acting on the ends of the strut in opposite directions upon application of an opening force from inflation of the balloon (or expansion of another expansion device). When the frame expands radially, the vertical distance between the ends of the strut decreases to a distance $d_2$, as depicted in FIG. 15B. As the vertical distance decreases, so does the moment between forces $F_1$ and $F_2$. Hence, it can be seen that a relatively greater expansion force is required as the vertical distance and the moment between the ends of the strut decreases. Moreover, strain hardening (stiffening) at the ends of the strut increases as the frame expands, which increases the expansion force required to induce further plastic deformation at the ends of the strut. As such, the angles between the struts of the frame can be selected to limit radial expansion of the frame at a given opening pressure (e.g., inflation pressure of the balloon). In some embodiments, these angles can be at least 110 degrees or greater when the frame is expanded to its functional size. In some embodiments, these angles can be at least 120 degrees or greater when the frame is expanded to its functional size.

In addition, the inflow and outflow ends of a frame may be configured to over-expand more so than the middle portion of the frame due to the "dog boning" effect of the balloon used to expand the valve. To protect against over-expansion of the leaflet structure 14, the leaflet structure may be secured to the frame 12 below the upper row of struts 32, as best shown in FIG. 1. Thus, in embodiments in which the outflow end of the frame may be over-expanded, the leaflet structure is positioned at a level below where over-expansion is likely to occur, thereby protecting the leaflet structure from over-expansion.

In a known valve construction, the leaflets can protrude outwardly beyond the outflow end of the frame when the valve is crimped if the leaflets are mounted too close to the distal end of the frame. If the delivery catheter on which the crimped valve is mounted includes a pushing mechanism or stop member that pushes against or abuts the outflow end of the valve (for example, to maintain the position of the crimped valve on the delivery catheter), the pushing member or stop member can damage the exposed leaflets that extend beyond the outflow end 15 of the frame 12. Another benefit of mounting the leaflets at a location spaced from the outflow end 15 of the frame 12 is that when the valve is crimped on a delivery catheter, the leaflets 40 do not protrude beyond the outflow end 15 of the frame 12 in the axial direction. As such, if the delivery catheter includes a pushing mechanism or stop member that pushes against or abuts the outflow end of the valve, the pushing mechanism or stop member can contact the end of the frame 12, and not leaflets 40, so as to avoid damage to the leaflets.

Figure 16:
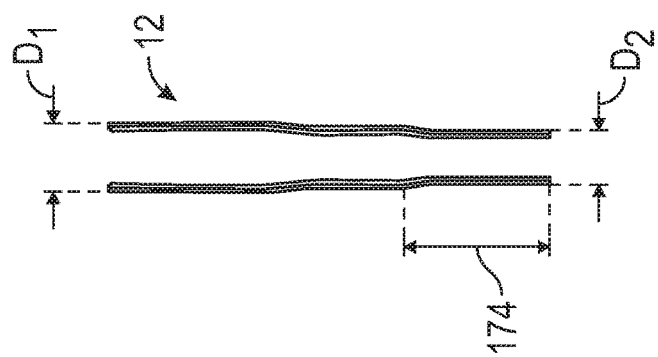
FIG. 16 illustrates a cross-sectional profile of the frame of FIG. 4, showing a general tapering from the outflow end to the inflow end.

Also, as can be seen in FIG. 5, the openings 36 of the lowermost row of openings in the frame 12 are relatively larger than the openings 38 of the two intermediate rows of openings. This allows the frame, when crimped, to assume an overall tapered shape that tapers from a maximum diameter $D_1$ at the outflow end of the valve to a minimum diameter $D_2$ at the inflow end of the valve, as shown in FIG. 16 and further described in U.S. Publication No. 2012/0123529, which is incorporated herein by reference. When crimped, the frame 12 has a reduced diameter region extending along a portion of the frame adjacent the inflow end of the frame, indicated by reference number 174, which generally corresponds to the region of the frame covered by the outer skirt 18. The diameter of region 174 is reduced compared to the diameter of the upper portion of the frame (which is not covered by the outer skirt) such that the outer skirt 18 need not increase the overall crimp profile of the valve. When the valve is deployed, the frame can expand to the cylindrical shape shown in FIG. 4. In one example, the frame of a 26-mm valve, when crimped, had a diameter $D_1$ of 14 French at the outflow end of the valve and a diameter $D_2$ of 12 French at the inflow end of the valve.

Figure 11:
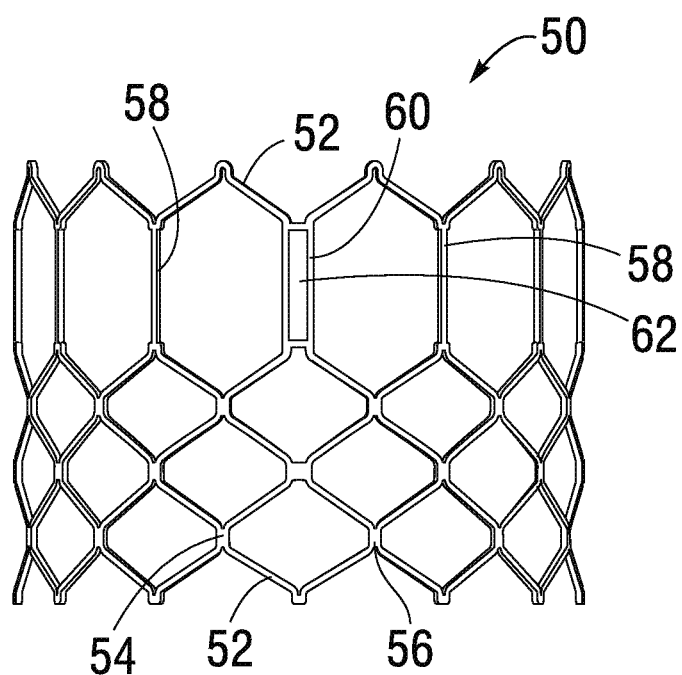

FIGS. 11 and 12 show an alternative frame 50 that can be incorporated in the valve 10. The frame 50 comprises multiple rows of circumferentially extending, angled struts 52 that are connected to each other at nodes, or connecting portions, 54 and 56. The uppermost row of struts 52 are connected to an adjacent row of struts by a plurality of axially extending struts 58 and commissure window frame portions 60. Each commissure frame portion 60 defines a slot or commissure window 62 for mounting a respective commissure of the valvular structure, as described in U.S. Patent Publication No. 2012/0123529 incorporated by reference above. In particular embodiments, the thickness T of the frame 50 is about 0.45 mm or less. FIGS. 13 and 14 are enlarged views of the portions of the frame 50 identified by letters A and B, respectively, in FIG. 12.

Figure 17:
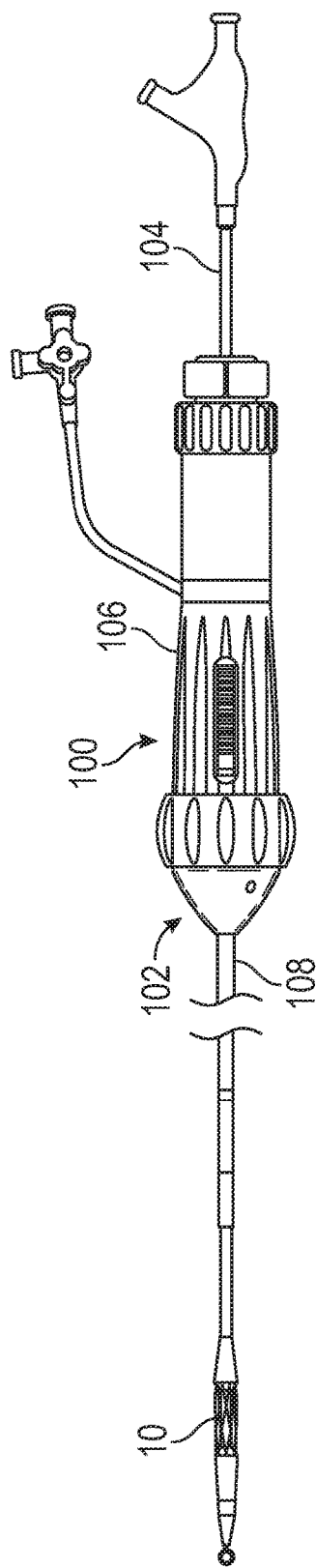
FIG. 17 illustrates a representative embodiment of a delivery apparatus for deploying a prosthetic heart valve in a patient.

In use, the prosthetic valve 10 can be crimped onto a delivery apparatus for delivery to the treatment site. FIG. 17 illustrates a representative embodiment of a delivery apparatus 100 that can be used to deliver a prosthetic heart valve to a patient. The delivery apparatus 100 is exemplary only, and can be used in combination with any of the prosthetic heart valve embodiments described herein. Likewise, the prosthetic heart valves disclosed herein can be used in combination with any of various known delivery apparatuses. The delivery apparatus 100 illustrated can generally include a steerable guide catheter 102 and a balloon catheter 104 extending through the guide catheter 102. A prosthetic device, such as a prosthetic heart valve shown schematically at 10, can be positioned on the distal end of the balloon catheter 104. For example, the prosthetic heart valve 10 can be crimped onto a balloon 114 (FIG. 21) located at the distal end of the balloon catheter 104. The balloon 114 can be configured to expand to a cylindrical shape when inflation fluid is provided to the balloon interior through the balloon catheter 104, thereby expanding the prosthetic heart valve 10 as described in greater detail in U.S. Publication No. 2017/0065415, incorporated herein by reference. The guide catheter 102 and the balloon catheter 104 can be adapted to slide longitudinally relative to each other to facilitate delivery and positioning of a prosthetic heart valve 10 at an implantation site in a patient's body. The guide catheter 102 includes a handle portion 106 and an elongated guide tube or shaft 108 extending from the handle portion 106.

Figure 18:
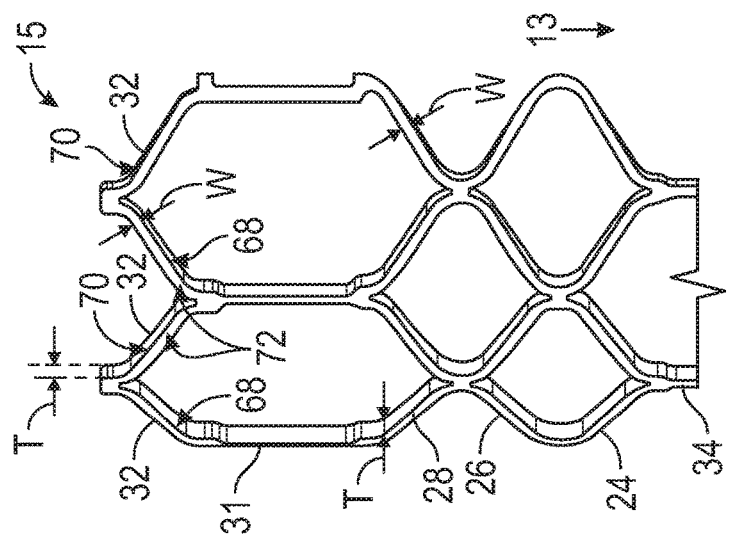
FIG. 18 is a magnified perspective view of a portion of the frame of FIG. 4.

Returning to FIG. 4, as noted above the frame 12 can have a wall thickness T measured in the radial direction from the interior surfaces of the frame struts to the exterior surfaces of the struts. In embodiments in which the frame 12 is formed from a tube (e.g., by laser-cutting), the struts of the frame 12 can have a uniform thickness T corresponding to the wall thickness of the tube from which the frame is cut. In other embodiments, the wall thickness of the tube may be varied (e.g., by machining, reaming, etching, etc.), which can result in variation of the radial thickness of the struts. As noted above, the struts 22, 24, 26, 28, and 32 can define the respective angles 42a-42e. Referring to FIG. 18, the struts can also comprise a thickness dimension measured generally in the plane of the curved exterior surface of the frame, referred to herein as "strut width" W. For example, as shown in FIG. 18, each of the struts 32 can have a surface 68 oriented generally in the direction of the inflow end 13, a corresponding surface 70 on the opposite side of the strut and oriented generally in the direction of the outflow end 15, and an exterior surface 72 that is perpendicular to the surface 68 and to the surface 70. The thickness of the struts 32 as measured between the inflow surface 68 and the outflow surface 70 is referred to herein as the strut width W. Stated differently, the strut width W is the dimension of the exterior surface 72 of the strut 32 measured in a direction perpendicular to the strut's longitudinal axis. Each of the struts 22, 24, 26, 28, and 32 can comprise a strut width as defined above. The corresponding dimension of the radially inward-facing surfaces of the strut members opposite the outer surfaces 72 can be the same or different as the strut widths of the outer surfaces 72, depending upon the particular characteristics desired.

It certain embodiments, it is possible to influence the shape of the frame during deployment (e.g., the shape of the frame as it transitions between the initial collapsed state and the expanded state) by varying the stiffness or resistance to radial expansion of various portions of the frame relative to each other. It is also possible to influence the shape of the fully expanded frame 12 in a similar manner. One way of tuning the resistance to expansion is by varying the strut width W and/or one or more of the angles 42a-42e between the strut members of the various rows I-V. For example, by varying the strut width W and/or the angles between the strut members of the various rows, a frame such as the frame 12 can be manufactured in a cylindrical shape (e.g., from cylindrically-shaped tube stock), and crimped to a reduced diameter on a balloon (or other expansion mechanism) that is configured to expand to a cylindrical shape. The strut width and angle parameters can be tuned such that when expanded using a cylindrical balloon, the frame 12 can assume any of a variety of non-cylindrical shapes on the cylindrical balloon between the partially-expanded and the fully-expanded states. This can allow the frame shape to be optimized, for example, to achieve improved hemodynamic properties, to influence the location in the native valve at which the prosthetic valve is anchored, to control the position of the frame relative to sensitive anatomical features, and/or to control the pressure applied by the prosthetic valve to the surrounding anatomy. Such parameters can also be used to influence the proportion of the overall frame length that is disposed in a vessel or chamber upstream of the native valve and downstream of the native valve.

Figure 19:
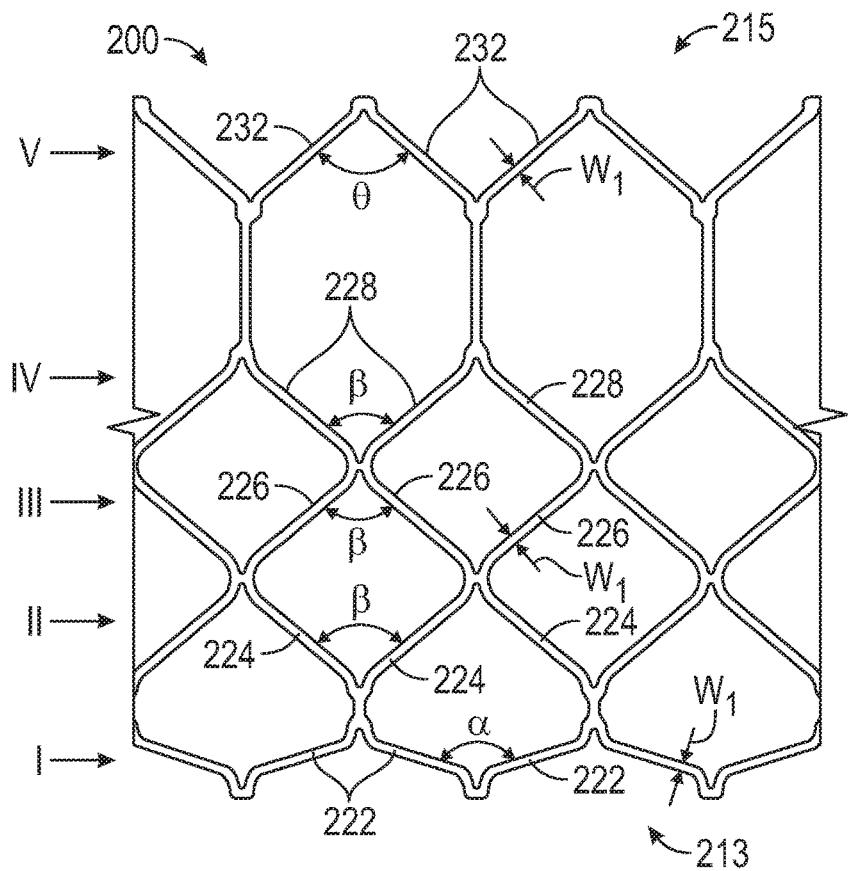
FIG. 19 illustrates a portion of a frame of a prosthetic heart valve, according to another embodiment.

For example, FIG. 19 illustrates a portion of a frame 200 configured similarly to the frame 12 in which the struts 222 of the first row I at the inflow end portion 213 of the frame have a strut width $W_1$, and define a first angle α. The struts 224 of the second row II can have the strut width $W_1$, and can define a second angle β. Likewise, the struts 226 of the third row III can have the strut width $W_1$ and can form the angle β between adjacent struts 226, and the struts 228 of the fourth row IV can also have the strut width $W_1$ and can form the angle β between adjacent struts 228. The struts 232 of the fifth row V at the outflow end portion 215 of the frame can also have the strut width $W_1$. However, the struts 232 can define a third angle θ, which can be different from the first angle α and different from the second angle β.

In certain embodiments the first angle α can be greater than the second angle β, and the second angle β can be greater than third angle θ. For example, in some embodiments, the first angle α can be from 100° to 170°, 110° to 170°, or 120° to 170°. In particular embodiments, the angle α can be 122°. In some embodiments, the second angle β can be 80° to 150°, 80° to 130°, or 90° to 120°. In particular embodiments, the angle β can be 94°. In some embodiments, the third angle θ can be from 50° to 130°, 60° to 120°, or 70° to 110°. In particular embodiments, the angle θ can be 80°. In certain embodiments, the strut width $W_1$ can be from 0.1 mm to 1 mm, 0.1 mm to 0.9 mm, 0.1 mm to 0.8 mm, or 0.2 mm to 0.6 mm. In particular embodiments, the strut width $W_1$ can be 0.3 mm, or 0.22 mm. In yet other embodiments, the frames described herein can include one or more rows of struts in which the angle between strut members is relatively large, such as from 110° to 170° or 180°, one or more rows of struts comprising an intermediate angle between struts such as 80° to 120°, and one or more rows of struts in which the angle between struts is relatively small, such as from 40° to 90°.

As noted above, the combination of the strut width $W_1$ and the angles α, β, and θ can allow the frame 200 to be manufactured in a cylindrical shape, crimped to a reduced diameter on a cylindrical balloon, and expanded to a non-cylindrical shape when partially expanded and/or when fully expanded. More particularly, each of the inflow end, the outflow end, and/or the central portion of the frame can be configured to expand to a specified design diameter (also referred to as a specified diameter, a design diameter, or a deployment diameter). The particular specified design diameter of the different portions can correspond to, for example, the size and shape of the individual's anatomy into which the prosthetic valve is to be implanted, the diameter, or diameter range, at which the leaflets of the prosthetic valve are configured to function, etc. The specified design diameter of the various portions of the frame and may be greater than, less than, or equal to the diameter of the tube stock from which the frame was manufactured.

Figure 20:
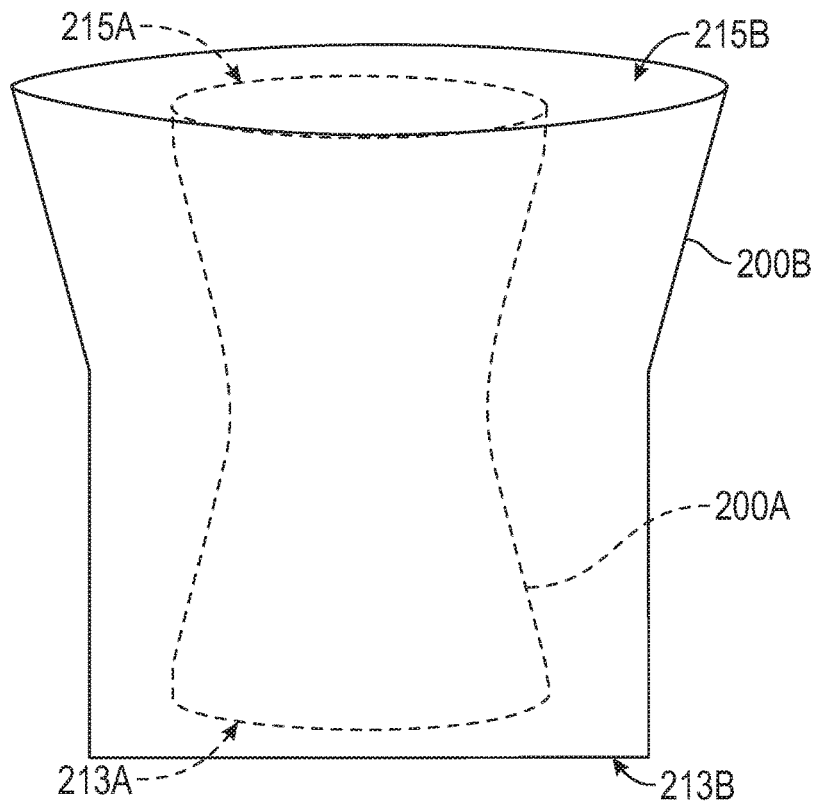
FIG. 20 schematically illustrates the hourglass-shaped profile of the frame of FIG. 19 when in a partially-expanded state and the Y-shaped profile of the frame when in a fully-expanded state.

The larger angle α can make the struts 222 of the inflow end relatively stiffer or more resistant to radial expansion, especially expansion beyond the specified design diameter of the first row I, than the struts 224-228 comprising the smaller angle β. In some embodiments, this is because when the number of cells and the overall height of a frame are fixed, a larger angle can result in shorter struts. Shorter struts at a large angle can resist bending to a greater degree because the moment between the ends of the struts is reduced, as described above with reference to FIGS. 15A and 15B. The smaller angle θ can make the struts 232 of the outflow end 215 still less resistant to radial expansion than the struts 224-228. Thus, the particular combination of the strut width $W_1$ and the angles α, β, and θ described above can allow the frame 200 to form an hourglass shape during deployment when the struts at the inflow and outflow ends are less resistant to expansion, and to form a Y-shaped final configuration when fully expanded. FIG. 20 illustrates the hourglass-shaped profile 200A of the frame during deployment in dashed lines, with the inflow end indicated at 213A and the outflow end indicated at 215A. The frame profile 200A is superimposed on the Y-shaped profile of the fully expanded frame 200B shown in solid lines, with the inflow end indicated at 213B and the outflow end indicated at 215B.

As noted above, in certain embodiments the frame 200 can be expanded using a balloon, such as the balloon 114 of the delivery apparatus of FIG. 17. In certain embodiments, the balloon 114 can have a specified or nominal design diameter to which the balloon 114 inflates when filled with inflation fluid. In some embodiments, the diameter of the balloon 114 when fully inflated can be greater than the specified design diameter of the fully expanded prosthetic valve frame 200. In some embodiments, the fully inflated diameter of the balloon can be greater than the largest diameter portion(s) of the fully expanded frame. For example, the diameter of the balloon 114 when inflated to a specified pressure associated with the deploying the frame can be 5%, 10%, 15%, 20%, 25%, or 30% larger than the design diameter of largest portion of the frame. In particular embodiments, where the design diameter of the largest portion of the frame is 20 mm, the balloon can have a fully inflated design diameter of 23 mm, 15% larger than the design diameter of the frame. However, in other embodiments, the balloon and the frame may have the same diameter, or the balloon may have a smaller diameter than the largest diameter portion(s) of the frame.

Figure 21:
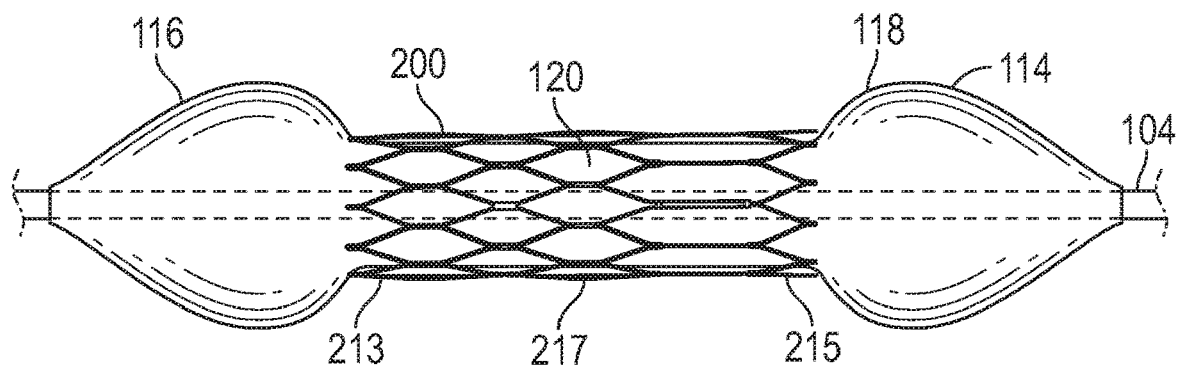
FIGS. 21-23 illustrate expansion of the frame of FIG. 19 on a balloon.
Figure 22A:
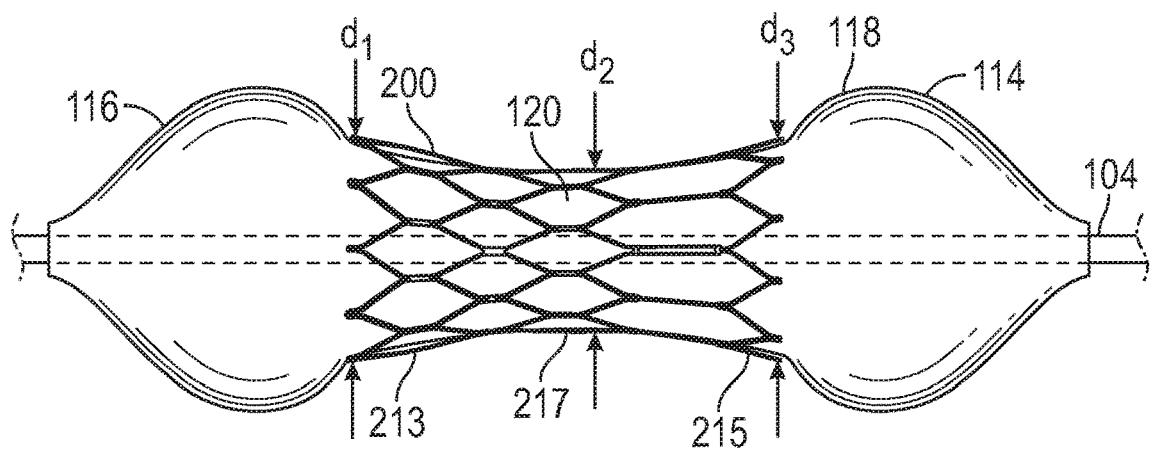
Figure 22B:
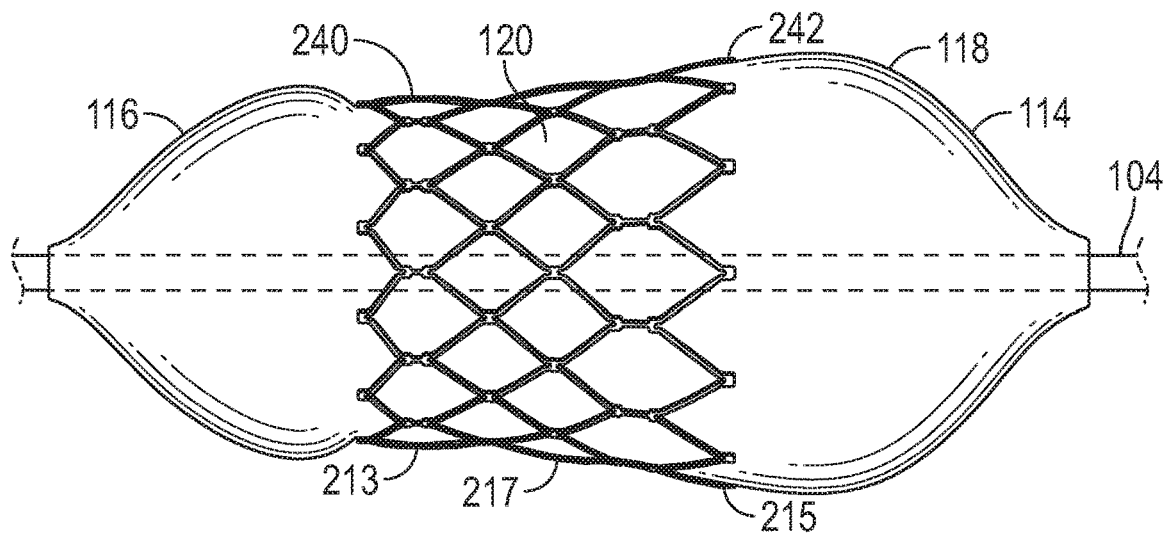
Figure 23:
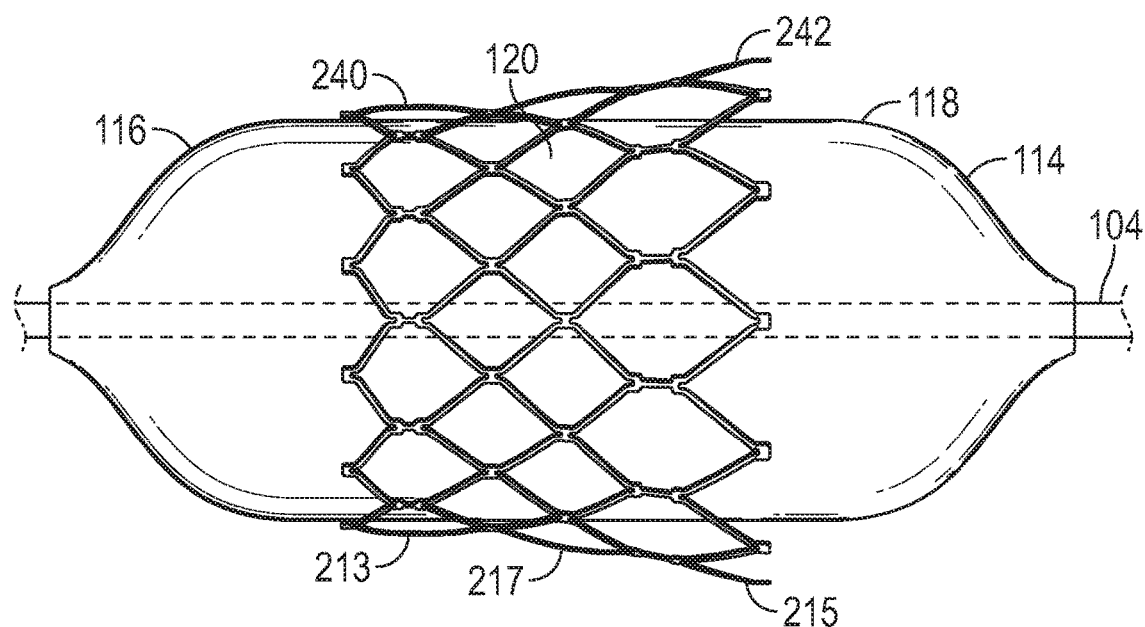

FIGS. 21-23 illustrate expansion of the frame 200 in greater detail using the balloon 114 of the delivery apparatus 100 of FIG. 17, where the fully inflated diameter of the balloon is greater than the design diameter of the largest portion of the frame. FIG. 21 illustrates the frame 200 crimped onto the balloon 114 at the distal end of the balloon catheter 104. When the balloon 114 is partially inflated, the balloon can be relatively more compliant than the frame 200. Thus, when the balloon 114 is below its fully inflated diameter, changes in the shape of the expanding frame 200 can be determined primarily by the strut width and strut angle parameters of the various portions of the frame. However, when the balloon 114 is fully inflated to its specified design diameter (and corresponding internal pressure), the balloon can become relatively less compliant than the frame 200, and the shape of the inflated balloon can influence the shape of the frame to a greater degree.

Thus, with reference to FIGS. 21 and 22A, as the balloon 114 expands, the balloon can form a "dog bone" shape in which the end portions 116 and 118, which are not constrained by the frame 200, inflate to a greater degree than the central portion 120 of the balloon around which the frame is crimped. During this phase, as the frame 200 begins to expand from the crimped configuration, the inflow end 213 and the outflow end 215 can expand faster or to a greater degree than the central portion 217 such that the frame assumes an hourglass shape. In other words, when the frame 200 is partially expanded, a diameter $d_1$ of the inflow end 213 and a diameter $d_3$ of the outflow end 215 can both be larger than a diameter $d_2$ of the central portion 217. The hourglass profile of the frame 200 can help to stabilize the frame on the balloon 114, and the relatively larger end portions 116 and 118 of the balloon 114 can prevent axial movement of the frame along the balloon during expansion.

FIG. 22B illustrates the frame 200 fully expanded on the balloon 114, which in turn is also inflated to an internal pressure corresponding to its fully inflated design diameter. In the fully expanded configuration, the combination of the strut width $W_1$ and the angles α, β, and θ can influence the shape of the frame 200 such that it assumes a Y-shaped configuration in which the frame comprises a cylindrical inflow portion generally indicated at 240, and a tapered or flared outflow portion 242. For example, as the frame 200 expands, the struts 222 of the row I at the inflow end 213 can resist expansion beyond a predetermined diameter $d_4$ (FIG. 24) due to the relatively large angle α between the struts 222. Meanwhile, the struts 232 at the outflow end 215, along with the struts of the rows II-IV, can expand to a greater extent than the struts 222 at the inflow end 213 due to the relatively smaller angles θ and β. This can cause the outflow end 215 to flare outwardly into a Y-shape as the balloon 114 inflates.

FIG. 23 illustrates the fully expanded frame 200 upon a partial release of pressure from the balloon 114. In FIG. 23, the cylindrical shape of the balloon 114 is evident, and the outflow end 215 is shown lifting radially away from the surface of the balloon.

Figure 24:
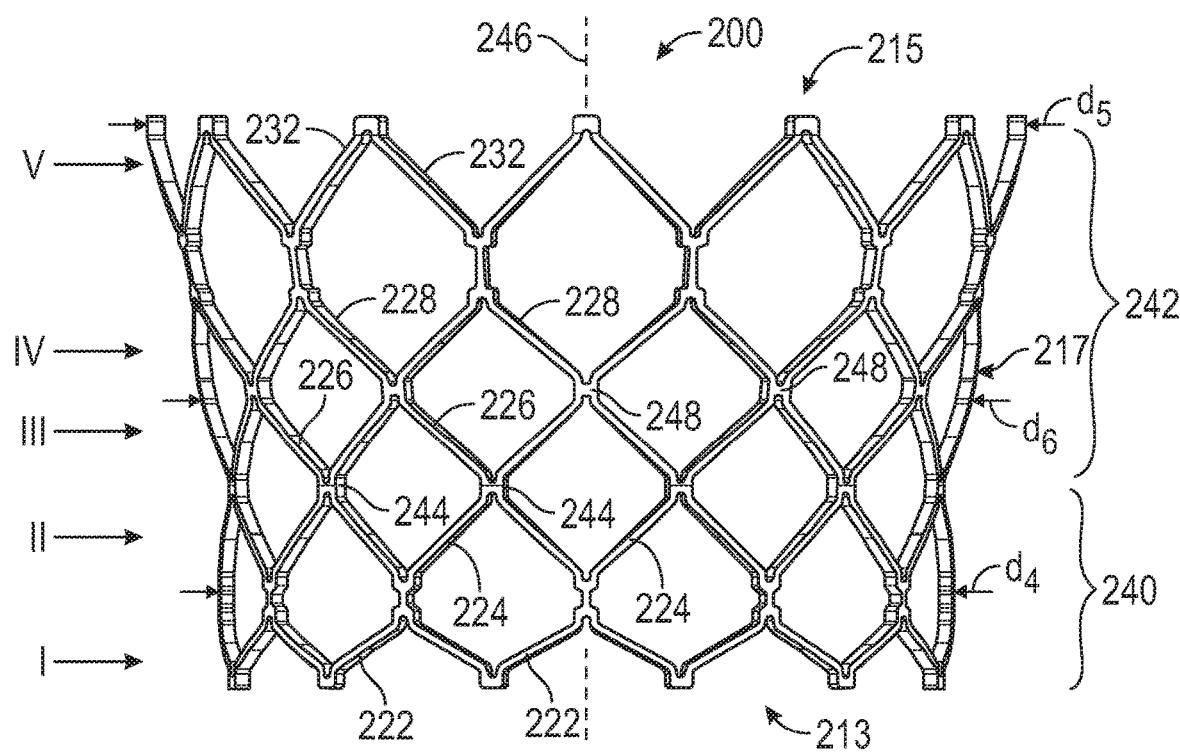
FIG. 24 is a side elevation view of the frame of FIG. 19 in a fully-expanded state.

FIG. 24 illustrates the fully expanded frame 200 in isolation. When fully expanded, the inflow portion 240 can extend from the inflow end 213 of the frame to about the level of the junctions 244 between the struts 224 of the second row II and the struts 226 of the third row III. The inflow portion 240 can have a generally uniform diameter $d_4$ along its length. Beginning at the level of the third row III of struts 226 (e.g., at the junctions 244), the struts can be angled radially away from the longitudinal axis 246 of the frame such that the diameter of the outflow portion 242 increases in a direction toward the outflow end 215. The outflow end 215 can thereby have an outflow diameter $d_5$ that is larger than the diameter $d_4$. The central portion 217, which can be located half way along the longitudinal axis 246 approximately at the junctions 248 between the struts 226 and the struts 228, can have a diameter $d_6$. The diameter $d_6$ can be equal to, substantially equal to, or greater than the diameter $d_4$ of the inflow end portion 213, but less than the diameter $d_5$ of the outflow end portion 215. As used herein, the term "substantially equal" refers to a measurement (e.g., a diameter or angle) that is within 1%, within 5%, or within 10% of a reference measurement (e.g., another diameter or angle). The frame 200 can be configured to retain the Y-shaped profile after the balloon 114 is deflated and the delivery apparatus is removed. In certain embodiments, the outflow diameter $d_5$ can be 1% to 100% larger, 5% to 75% larger, 5% to 50% larger, 5% to 25% larger, or 10% larger than the diameter $d_4$.

The Y-shaped configuration of the frame 200 when fully expanded can provide a number of advantages. For example, the larger diameter outflow portion 242 can aid in anchoring the prosthetic valve in the lumen of the native valve, especially in patients with leaflet calcification or stenosis. For example, the larger diameter outflow portion 242 can anchor the frame 200 against the calcified native leaflets and, in certain circumstances, the inflow portion 240 of the frame need not contact, or need only minimally contact, the native annulus in order to keep the frame at the desired location in the native valve. Anchoring the prosthetic valve at the level of the native leaflets using the Y-shaped outflow portion 242 can thereby reduce the pressure applied to the native annulus, and reduce the risk of annular rupture. The smaller diameter of the inflow portion 240 of the Y-shaped frame configuration can also aid in spacing the frame away from the His bundle, reducing the risk of electrical conduction abnormalities and/or interference by the frame with the heart's electrical impulse pathways. This can potentially reduce the need for a pacemaker.

The relatively large outflow diameter can also provide the hydrodynamic performance of a prosthetic valve with a diameter equal to $d_5$, but without requiring that the entire frame be expanded to this diameter. For example, the leaflets of the prosthetic valve can be sized and shaped to correspond to the larger diameter $d_5$ of the outflow portion 242. This can allow the prosthetic leaflets to coapt and seal through a range of diameters up to or exceeding the design diameter $d_5$ of the outflow portion 242, allowing the prosthetic valve to maintain a large pressure gradient across the prosthetic valve. This configuration can also avoid the central opening between leaflets that can occur at diastole in when existing prosthetic valves are over-expanded.

Figure 25:
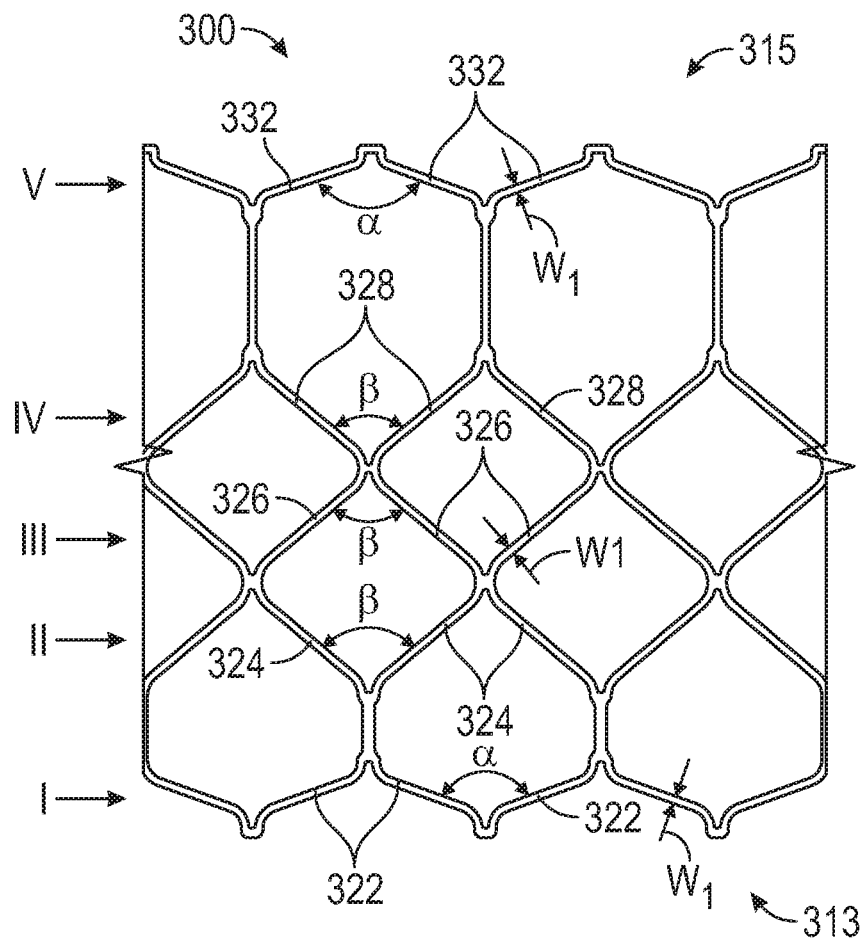
FIG. 25 illustrates a portion of a frame of a prosthetic heart valve, according to another embodiment.

FIG. 25 illustrates a portion of a frame 300 configured similarly to the frame 12 in which all of the struts have the same strut width $W_1$, and the struts 322 of the first row I at the inflow end 313 of the frame define a first angle α. The struts 324 of the second row II, the struts 326 of the third row III, and the struts 328 of the fourth row IV all define a second angle β. The struts 332 of the fifth row V at the outflow end 315 can define the first angle α between them. The angle first angle α can be larger than the second angle β. For example, in certain embodiments the first angle α can be from 90° to 160°, 100° to 150°, 110° to 140°, or 120°. In particular embodiments, the first angle α can be 122°. The second angle β can be from 50° to 110°, 60° to 100°, 70° to 90°, or 80°. In particular embodiments, the angle μ can be 82°. The strut width $W_1$ can have any of the values given herein.

Figure 26:
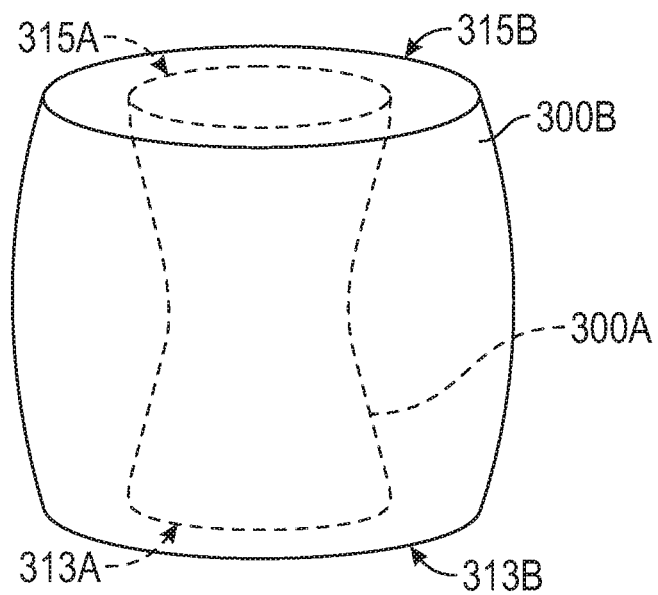
FIG. 26 schematically illustrates the hourglass-shaped profile of the frame of FIG. 25 when in a partially-expanded state and the barrel-shaped profile of the frame when in a fully-expanded state.

The frame 300 can be formed in a cylindrical shape, and can be radially collapsed onto a delivery apparatus as described above. Because the angle α is larger than the angle β and the strut widths of all of the struts are the same, the struts 322 at the inflow end 313 and the struts 332 at the outflow end 315 can resist expansion to a greater degree than the struts 324, 326, and 328, especially beyond the design diameter(s) of the first row I and the fifth row V. Thus, when the balloon is inflated, the frame 300 can form an hourglass shape when partially expanded, and can form a barrel shape when fully expanded to its functional size. The hourglass-shaped partially-expanded profile of the frame is illustrated in dashed lines at 300A in FIG. 26, and superimposed on the fully-expanded barrel-shaped profile 300B shown in solid lines. The inflow and outflow ends of the frame profile 300A are also indicated at 313A and 315A, respectively.

Figure 27:
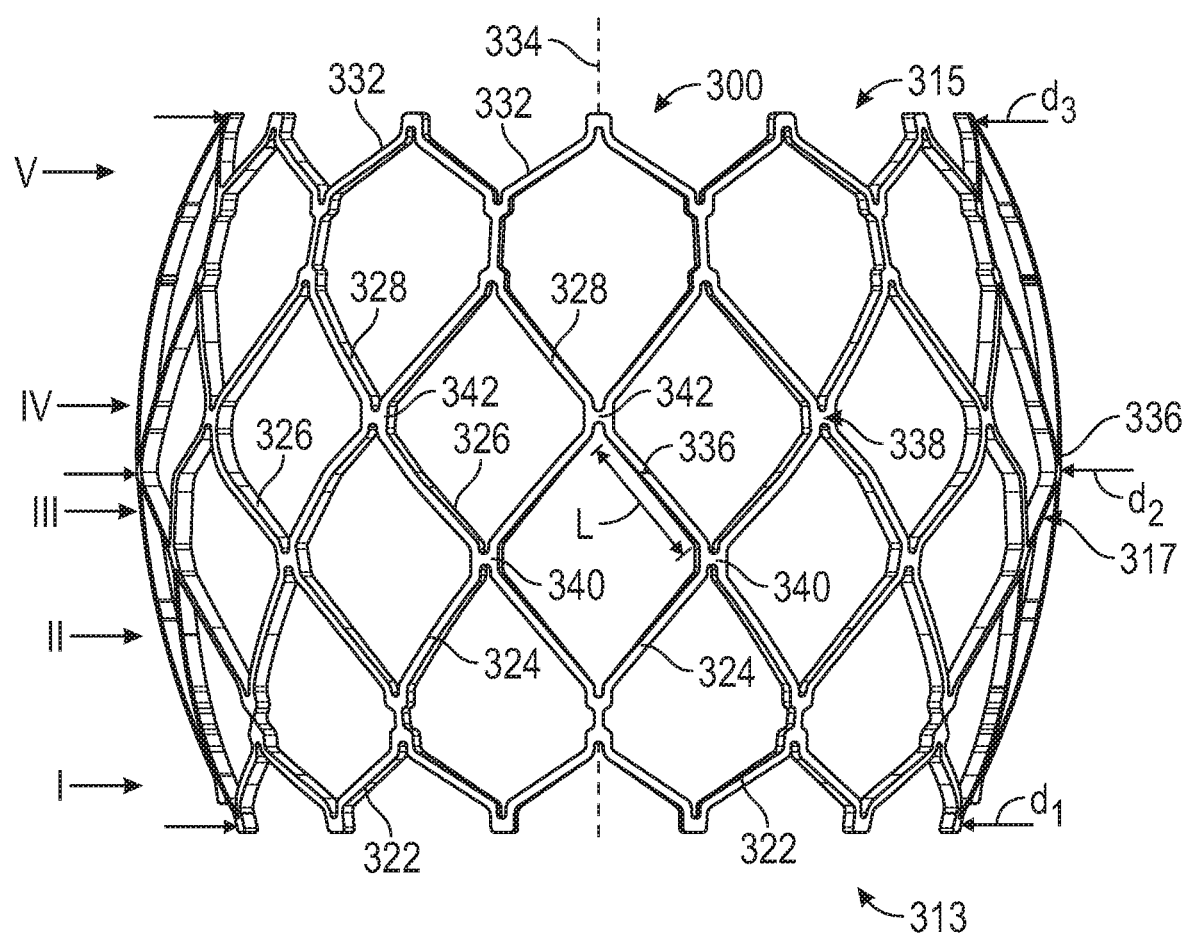
FIG. 27 is a side elevation view of the frame of FIG. 25 in a fully-expanded state.

FIG. 27 illustrates the frame 300 in the fully-expanded barrel-shaped configuration, in which the struts are curved such that the exterior surface 338 of the frame has a convex profile and defines an apex 336 at a central portion 317 of the frame. The apex 336 can correspond to a maximum radial distance between the longitudinal axis 334 of the frame and the exterior surface 338. Thus, when fully expanded, the frame 300 can define a diameter $d_1$ at the inflow end 313, a diameter $d_3$ at the outflow end 315, and a diameter $d_2$ at the apex 336 of the central portion 317 that is larger than the diameters $d_1$ and $d_3$. In the illustrated embodiment, the apex 336 is located along the length L of the struts 326 of the third row III, such as about two-thirds of the distance between the junctions 340 and the junctions 342, although the apex 336 can be located at any selected location on any selected strut member. Thus, in the illustrated configuration the struts 322 of the first row I, the struts 324 of the second row II, and at least a portion of the struts 326 of the third row III can be angled away from the longitudinal axis 334 of the frame such that the diameter of the frame increases in a direction from the inflow end 313 toward the outflow end 315 from the diameter $d_1$ to the diameter $d_2$. Beyond the apex 336, the remainder of the struts 326 of the third row III, and the struts 328 of the fourth row IV and the struts 332 of the fifth row V can be angled toward the longitudinal axis 334 such that the diameter of the frame decreases in a direction toward the outflow end 315 from the diameter $d_2$ to the diameter $d_3$.

In certain embodiments, the diameters $d_1$ and $d_3$ can be the same or different. In certain embodiments, the diameter $d_2$ at the apex 336 can be from 1% to 25% larger than the diameter $d_1$ and/or the diameter $d_3$. For example, in particular embodiments in which the specified design diameter of the inflow end $d_1$ and/or of the outflow end $d_3$ is 23 mm, the diameter $d_2$ can be 27 mm, or 17% larger than the diameters $d_1$ and $d_3$.

The barrel-shaped profile of the fully expanded frame 300 can also provide certain advantages. For example, the reduced diameter $d_1$ at the inflow end can space the frame away from the His bundle, thereby reducing the risk of electrical conduction abnormalities and rupture of the native valve annulus. When implanted in the native aortic valve, the reduced diameter $d_3$ at the outflow end of the frame 300 can space the frame away from the coronary ostia, and thereby reduce the risk of blocking the coronary arteries with, for example, the native leaflets displaced by the frame. This can also improve access to the coronary ostia post-implantation. The barrel-shaped profile can also provide certain hydrodynamic performance advantages. For example, the reduced diameter $d_3$ at the outflow end 315 can improve coaptation of the prosthetic valve leaflets, resulting in reduction or elimination of the opening between the leaflets during ventricular diastole. The barrel-shaped profile can also reduce contact between the prosthetic leaflets and the frame during valve operation, prolonging the service life of the prosthetic valve. The prosthetic leaflets can also have more space in which to open and close within the frame, improving flow through the valve. The hourglass shape during deployment can also provide stability on the delivery apparatus, as described above.

Figure 28:
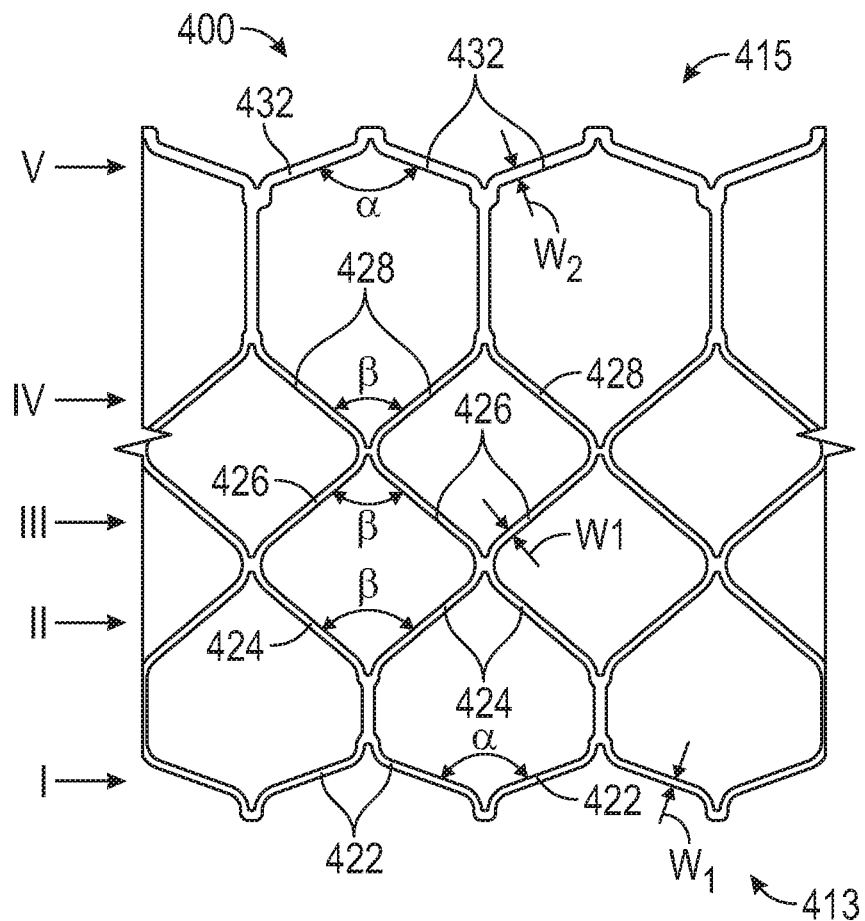
FIGS. 28 and 29 illustrate another embodiment of a frame configured to assume a frustoconical shape when partially expanded, and to assume a barrel shape when fully expanded.

FIG. 28 illustrates a portion of a frame 400 in which the struts have different strut widths and define different angles between strut members at various locations along the axis of the frame. For example, the struts 422 of the first row I at the inflow end 413 of the frame define a first angle α, and can have a first strut width $W_1$. The struts 424 of the second row II, the struts 426 of the third row III, and the struts 428 of the fourth row IV can all define a second angle β with the other strut members in their rows. The struts 424, 426, and 428 can also have the strut width $W_1$. The struts 432 of the fifth row V at the outflow end 415 can define the first angle α between them, and can have a strut width $W_2$ that is different from the strut width $W_1$. In certain embodiments, the strut width $W_2$ can be larger than the strut width $W_1$. For example, in certain embodiments the strut width $W_2$ can be 5% to 30% larger than the strut width $W_1$, such as 12%, 17%, or 25% larger than the strut width $W_1$. In particular embodiments, the strut width $W_1$ can be 0.28 mm and the strut width $W_2$ can be 0.32 mm.

The angle α can also be larger than the angle β. For example, in certain embodiments the first angle α can be from 110° to 170°. In particular embodiments, the first angle α can be 120°. The second angle β can be from 40° to 90°. In particular embodiments, the angle β can be 80°.

Figure 29:
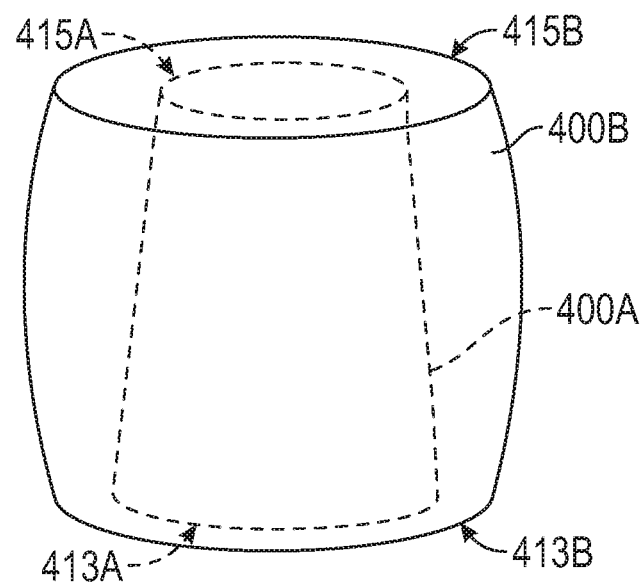

The larger angle α can make the struts 422 at the inflow end and the struts 432 at the outflow end more resistant to radial expansion, especially beyond the specified design diameter of the rows I and V, as described above. The larger strut width $W_2$ of the struts 432 can also make the outflow end 415 more resistant to radial expansion than the inflow end 413. Thus, this combination of strut angles and strut widths can cause the frame to assume a tapered, "A-shape," or frustoconical shape when partially expanded in which the diameter of the inflow end 413 is greater than the diameter of the outflow end 415 of the frame. When the inflow end 413 and the outflow end 415 reach their respective design diameters, the inflow and outflow ends can resist further expansion due to the relatively large angle α. Meanwhile, the struts 424-428 of the rows II-IV can continued to radially expand such that the frame 400 assumes a barrel-shaped profile similar to the frame 300 of FIG. 27. This is also illustrated in FIG. 29, in which the frustoconical, partially-expanded frame 400A, and its inflow end 413A and outflow end 415A, are illustrated in dashed lines. The profile of the partially-expanded frame 400A is shown superimposed on the fully-expanded barrel-shaped frame profile 400B and its inflow end 413B and outflow end 415B, which are illustrated in solid lines.

Figure 30:
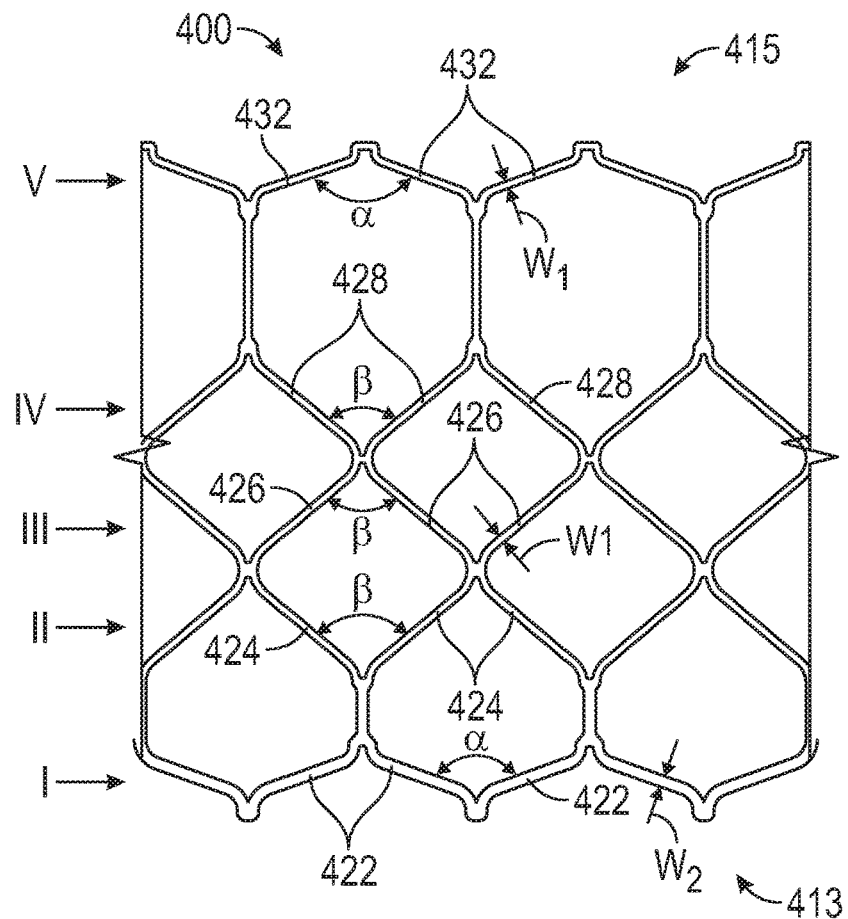
FIGS. 30 and 31 illustrate another embodiment of a frame configured to assume a V-shape when partially expanded, and to assume a barrel shape when fully expanded.
Figure 31:
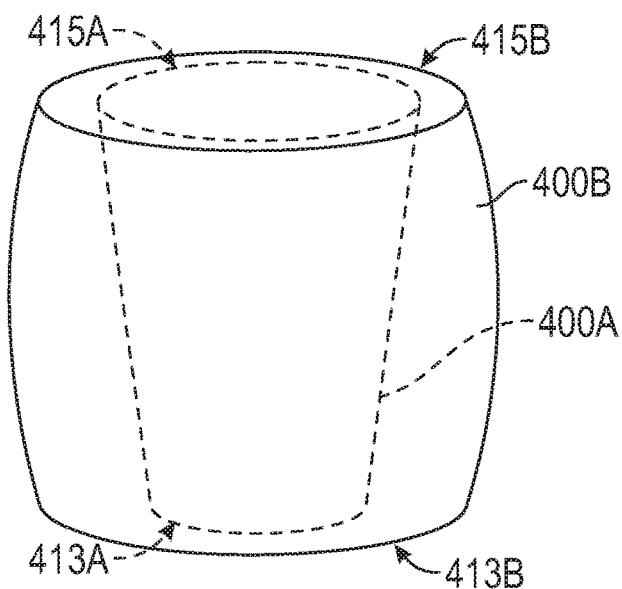

FIG. 30 illustrates another embodiment of the frame 400 in which the struts 422 at the inflow end 413 of the frame comprise the larger strut width $W_2$, and the struts 432 of the outflow end 415 comprise the smaller strut width $W_1$. This can cause the frame 400 to assume a tapered, "V-shaped," or frustoconical profile oriented in the opposite direction with respect to the configuration illustrated in FIG. 28 when partially expanded. For example, in the configuration of FIG. 30, the diameter of the inflow end 413 can be smaller than the diameter of the outflow end 415 of the frame when the frame 400 is partially expanded due to the larger strut width $W_2$. When fully expanded, the frame can assume a barrel-shaped profile similar to the frame 300 shown in FIG. 28. This is also illustrated in FIG. 31, in which the frustoconical, partially-expanded frame 400A, with its inflow end 413A and outflow end 415A, is illustrated in dashed lines. The fully-expanded barrel-shaped frame 400B, with the fully expanded inflow and outflow ends 413B and 415B, is illustrated in solid lines.

Figure 32:
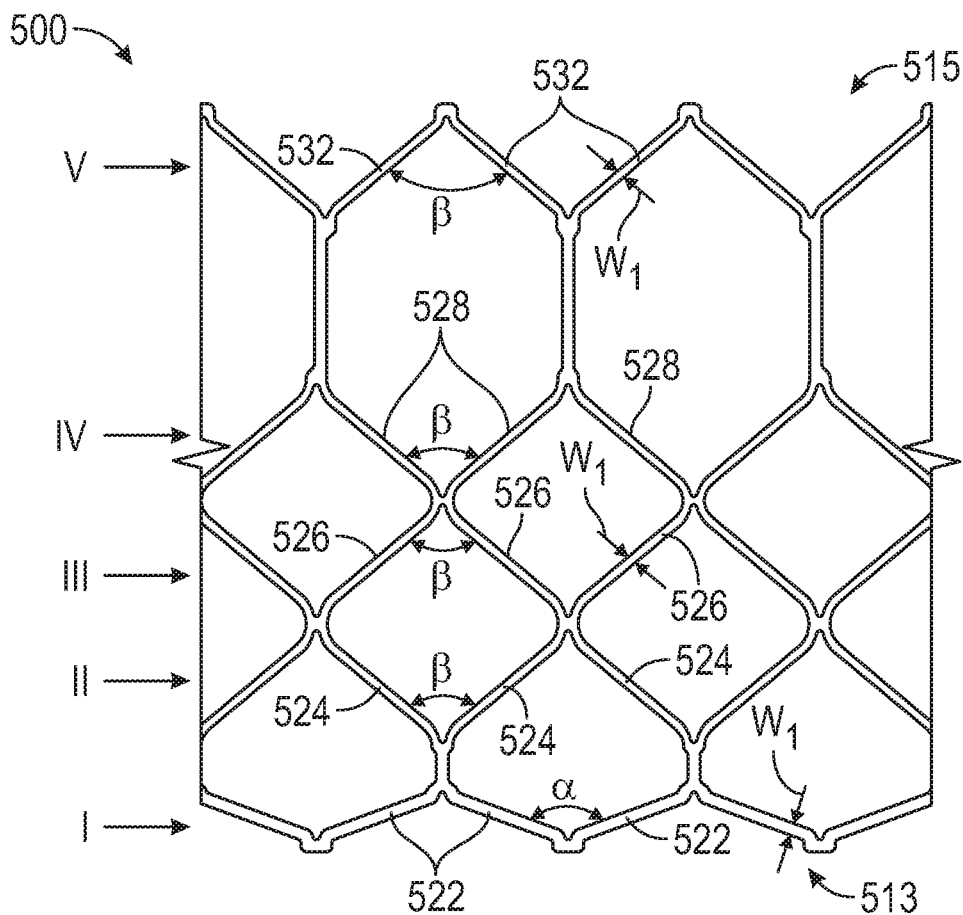
FIGS. 32 and 33 illustrate another embodiment of a frame configured to assume an hourglass shape when partially expanded, and to assume a V-shape when fully expanded.

FIG. 32 illustrates a portion of another frame 500 in which all of the struts of the rows I-V have the same strut width $W_1$, and define different angles between strut members at the inflow and outflow ends of the frame. For example, the struts 522 of the first row I at the inflow end 513 define a first angle α. The struts 524 of the second row II, the struts 526 of the third row III, the struts 528 of the fourth row IV, and the struts 532 of the fifth row V can all define an angle β with the other strut members in their rows. The second angle β can be smaller than the angle α. For example, in certain embodiments the first angle α can be from 110° to 170°. In particular embodiments, the first angle α can be 120°. The second angle β can be from 40° to 90°. In particular embodiments, the angle β can be 80°.

Figure 33:
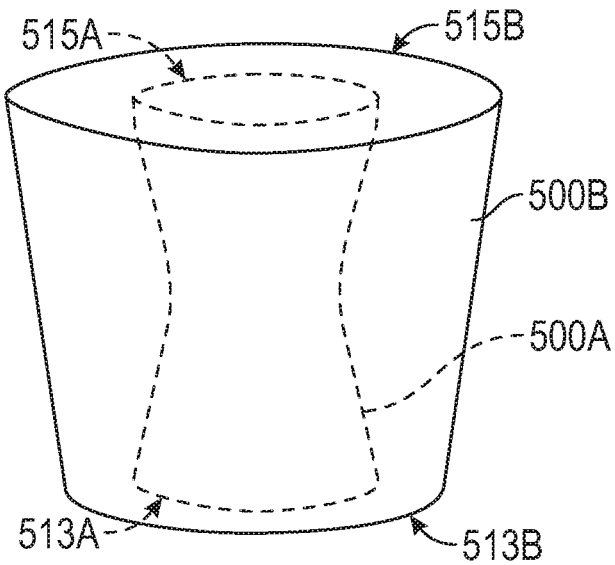
Figure 34:
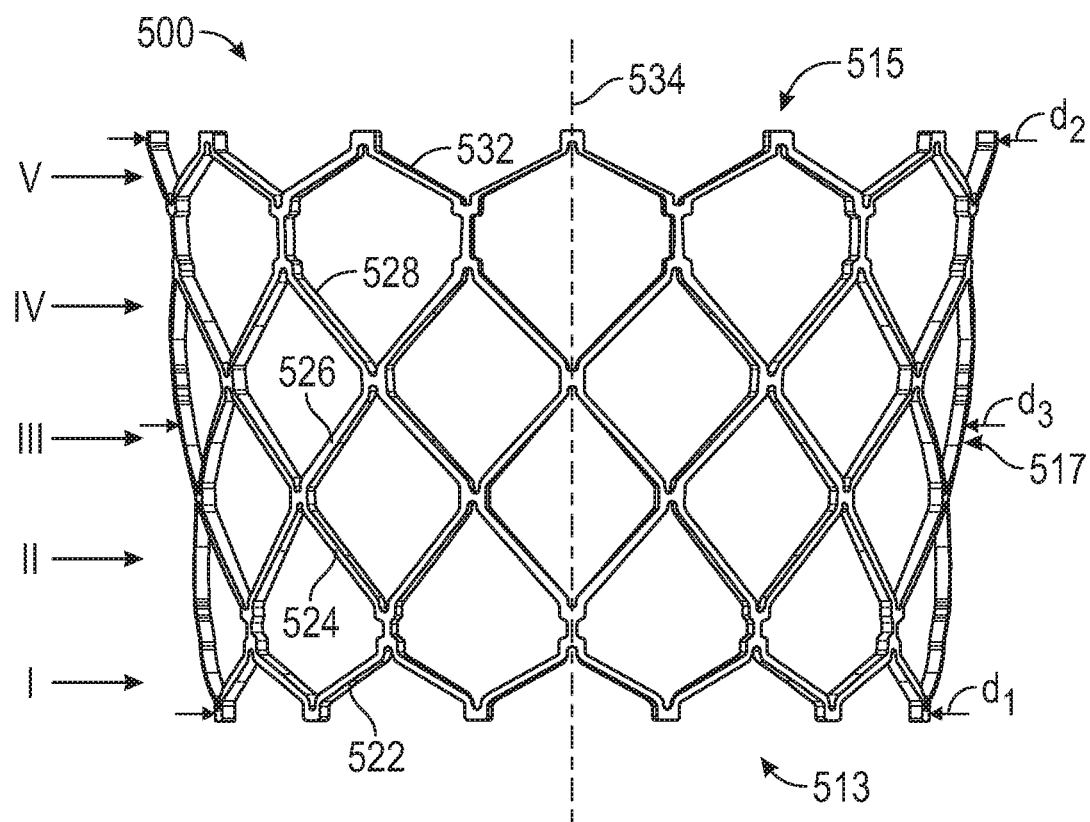
FIG. 34 is a side elevation view of the frame of FIG. 32 in the fully-expanded state.

By making the outflow angle β smaller than the inflow angle α with all strut widths the same, the struts 522 of the first row I can resist radial expansion beyond the specified design diameter of the first row I to a greater extent that the other rows. Thus, the frame 500 can form an hourglass shape when partially expanded, and can form a V-shaped or inverted frustoconical profile when fully expanded. FIG. 34 illustrates the fully expanded, V-shaped frame 500. The inflow end 513 can have a diameter $d_1$ that is smaller than the diameter $d_2$ of the outflow end 515 when the frame 500 is fully expanded. The diameter of the frame can vary between $d_1$ and $d_2$ as a function of distance along the axis 534 of the frame such that a diameter $d_3$ at a central portion 517 of the frame is greater than the diameter $d_1$, but less than the diameter $d_2$. This is also illustrated in FIG. 33, in which the profile of the inflow end 513A and the outflow end 515A of the partially expanded frame 500A are shown superimposed on the inflow end 513B and the outflow end 515B of the fully expanded frame 500B.

Potential advantages that can be associated with the inverted frustoconical deployed shape of the frame 500 in which the outflow diameter $d_2$ is greater than the inflow diameter $d_1$ are that the wider outflow end can provide for improved anchoring of the prosthetic valve at the level of the native leaflets and/or annulus, and can provide improved hydrodynamic function. The smaller inflow diameter can space the frame away from the His bundle, reducing the risk of interference with the heart's electrical signaling, as described above.

Figure 35:
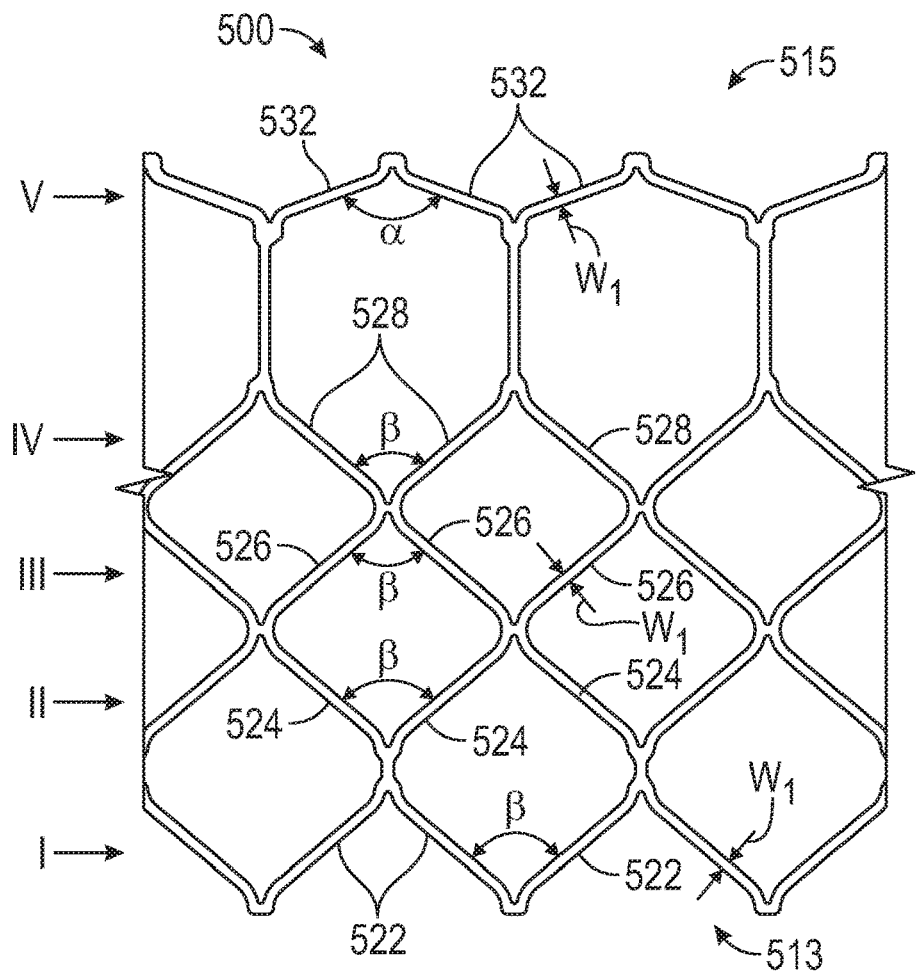
FIGS. 35 and 36 illustrate another embodiment of a frame configured to assume an hourglass shape when partially expanded, and to assume a frustoconical shape when fully expanded.
Figure 36:
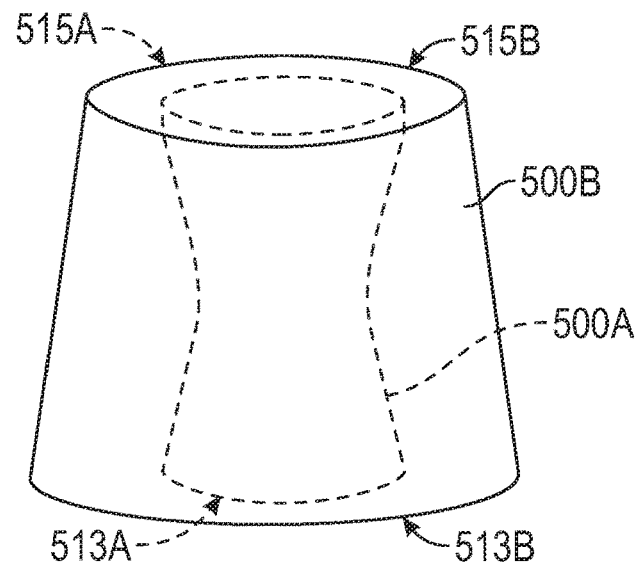

FIGS. 35 and 36 illustrate another embodiment of the frame 500 in which the strut members 532 at the outflow end of the frame comprise the larger angle α, and the remaining strut members, including the inflow strut members 522, comprise the smaller angle β. This can cause the frame 500 to form an hourglass shape during deployment, and a frustum when fully expanded in which the diameter of the inflow end 513B is larger than the diameter of the outflow end 515B, as shown in FIG. 36. Potential advantages that can be associated with the frustoconical deployed shape of the frame 500 of FIGS. 35 and 36, in which the outflow diameter is less than the inflow diameter, are that the wider inflow end may provide for better sealing in the native valve annulus, depending upon a particular patient's anatomy, and that the smaller outflow diameter can reduce the risk of blocking the coronary ostia with the native leaflets of the valve, as described above.

Figure 37:
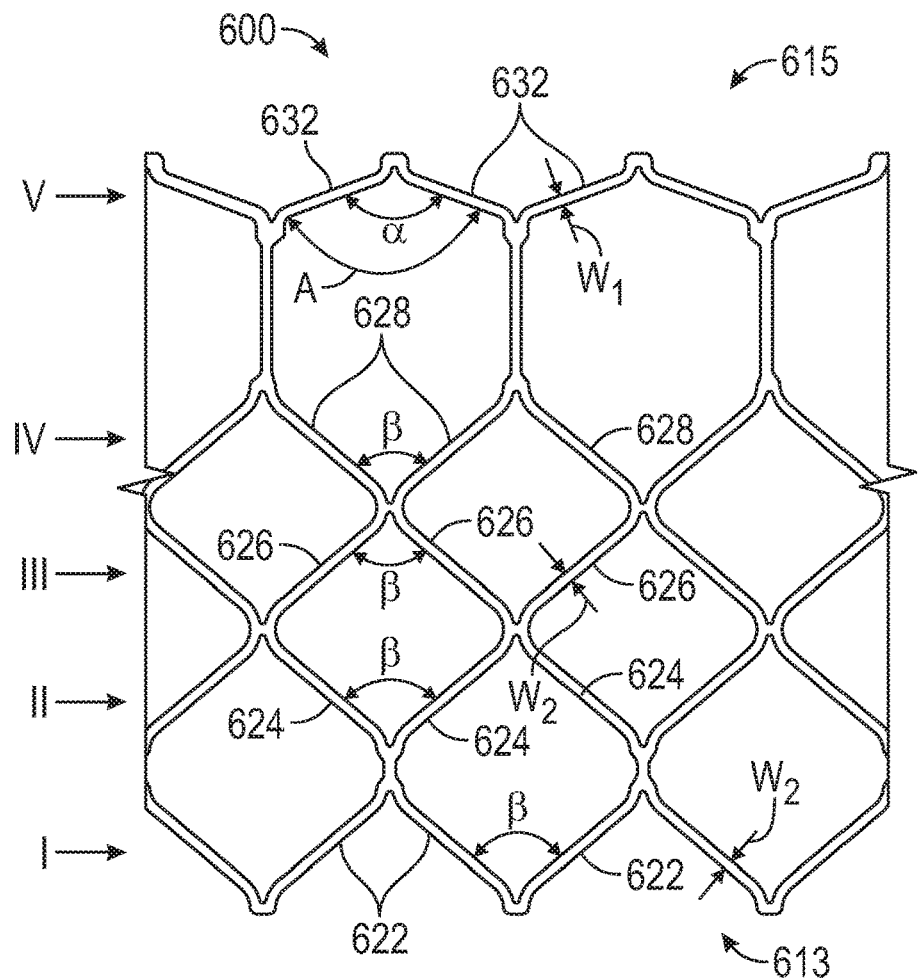
FIGS. 37 and 38 illustrate another embodiment of a frame configured to assume a frustoconical shape when partially expanded, and to maintain a frustoconical shape when fully expanded.
Figure 38:
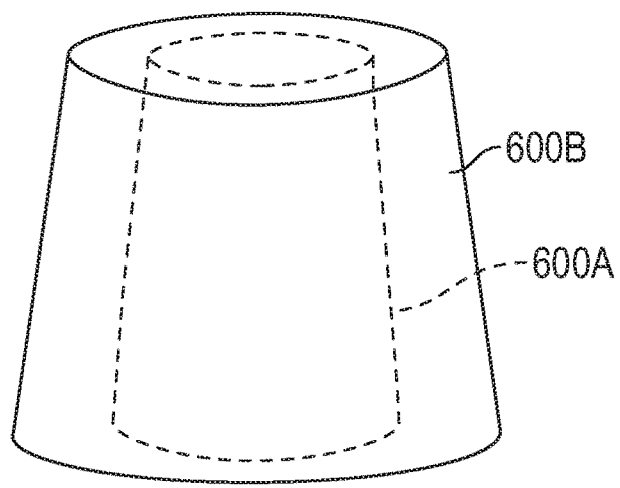

FIGS. 37 and 38 illustrate another configuration of a frame 600 in which the strut members 632 at the outflow end 615 of the frame define an angle α between them, and have a first strut width $W_1$. The remaining struts 622-628 can define a second angle β that is smaller than the angle α. The struts 622-628 can also have a strut width $W_2$ that is smaller than the strut width $W_1$. For example, in certain embodiments the first angle α can be from 110° to 170°, such as 120°. The second angle β can be from 40° to 90°, such as 80°. The first strut width $W_1$ can be from 0.30 mm to 0.36 mm, such as 0.32 mm, and the second strut width $W_2$ can be from 0.22 mm to 0.30 mm, such as 0.28 mm. In other words, in certain embodiments the second strut width $W_2$ can be 50% to 90% of the first strut width $W_1$, such as 60% to 88% of the first strut width $W_1$.

The combination of the larger angle α and the larger strut width $W_1$ of the outflow struts 632 can make the struts 632 more resistant to radial expansion, especially expansion beyond the specified design diameter of the fifth row V of struts 632. The struts 622-628 with the smaller strut width $W_2$ and the smaller angle θ can resist radial expansion to a lesser degree than the struts 632 of the outflow end 615. This combination of strut widths and angles can cause the frame 600 to assume a tapered, "A-shaped," or frustoconical profile when partially expanded, and to also have a tapered, "A-shaped," or frustoconical profile when fully expanded. The partially-expanded frame 600A is shown in dashed lines superimposed on the fully expanded frame 600B in FIG. 38. Although the partially expanded frame profile 600A and the fully expanded frame profile 600B have approximately the same proportions in FIG. 38, in some embodiments, the proportions of the frustoconical frame may differ between different degrees of expansion. The frustoconical shape of the frame 600 during deployment can improve the accuracy and/or predictability of the positioning of the prosthetic valve's exterior paralvalular-leakage prevention mechanism, such as the outer skirt 18 of FIGS. 1-3, during deployment. This, in turn, can improve sealing between the prosthetic valve and the surrounding anatomy, resulting in an attendant reduction in paravalvular leakage post-implantation.

Figure 39:
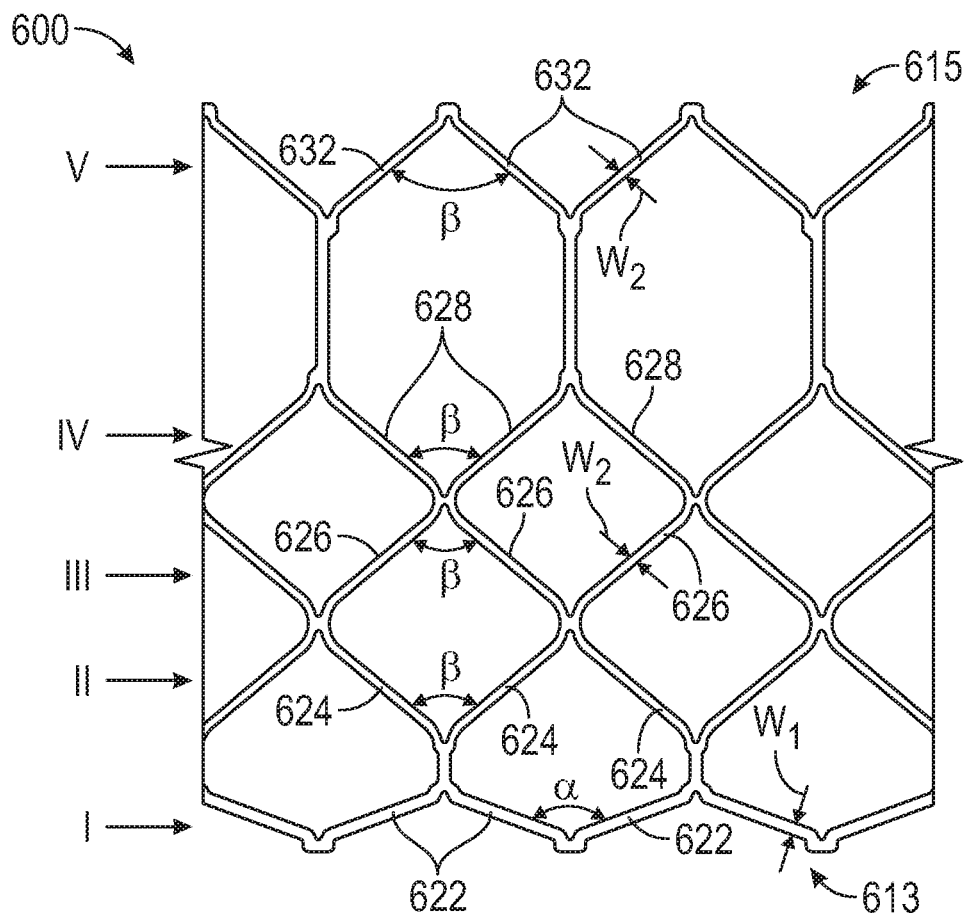
FIGS. 39 and 40 illustrate another embodiment of a frame configured to assume an inverted frustoconical or V-shape when partially expanded, and to maintain a V-shape when fully expanded.
Figure 40:
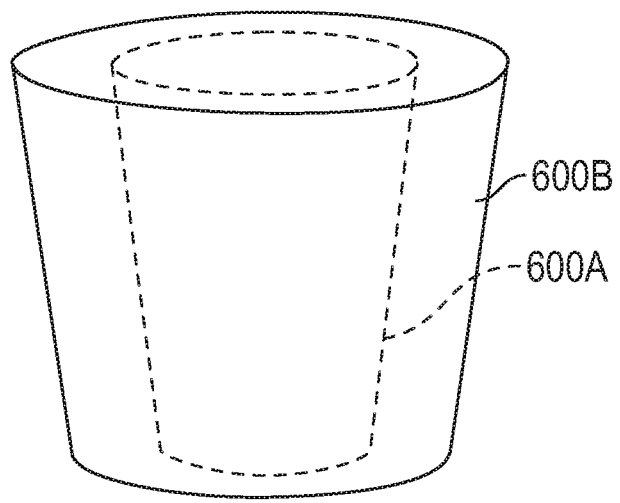

FIGS. 39 and 40 illustrate another embodiment of the frame 600 in which the strut members 622 at the inflow end 613 of the frame comprise the larger angle α, and the remaining strut members, including the outflow struts 632, comprise the smaller angle β. The inflow struts 622 also comprise the larger strut width $W_1$, while the remaining struts, including the outflow struts 632, comprise the smaller strut width $W_2$. This can make the inflow struts 622 more resistant to radial expansion than the outflow struts 632 and the struts 624-628 in between, which can cause the frame 600 to form an inverted frustoconical or "V-shaped" profile during deployment, and an inverted frustoconical or "V-shaped" profile when fully expanded. FIG. 40 illustrates the partially expanded frame 600A in dashed lines superimposed on the fully expanded frame 600B in solid lines. One potential advantage of the V-shaped profile of the frame 600 during deployment is that the larger diameter outflow end can trap or prevent passage of emboli as the prosthetic valve expands, potentially reducing the risk of stroke.

Figure 41:
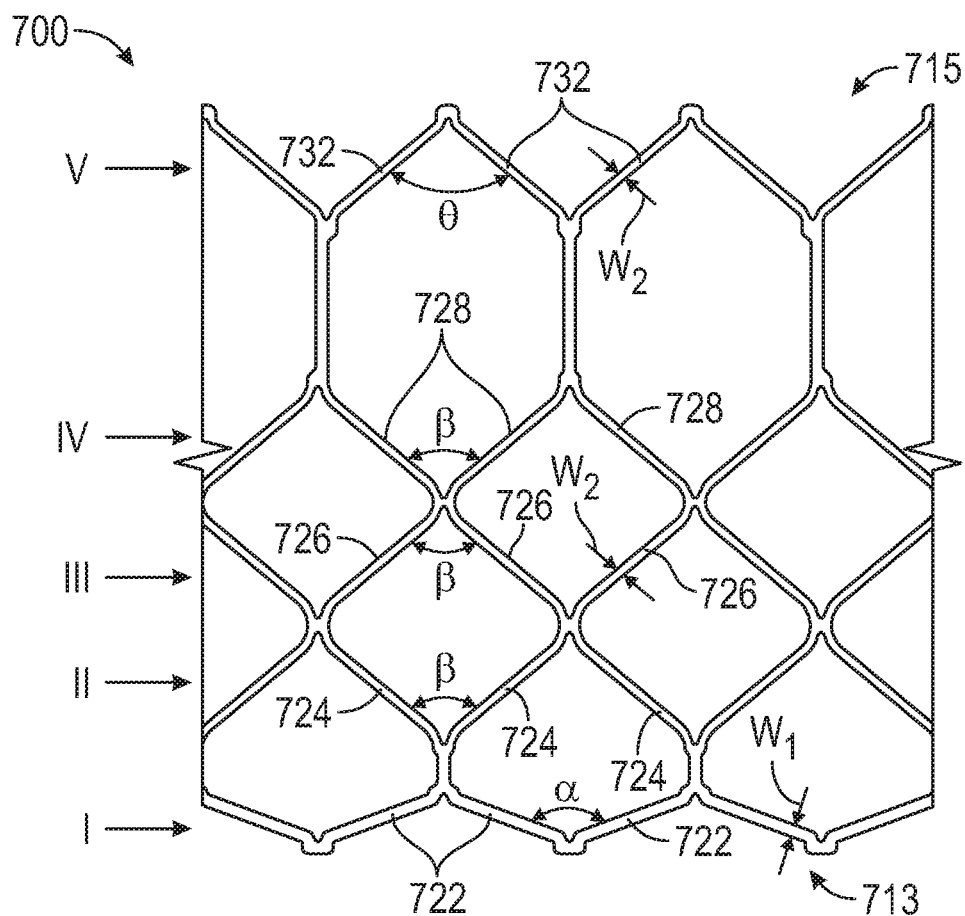
FIGS. 41 and 42 illustrate another embodiment of a frame configured to assume an inverted frustoconical or V-shape when partially expanded, and to assume a Y-shape when fully expanded.
Figure 42:
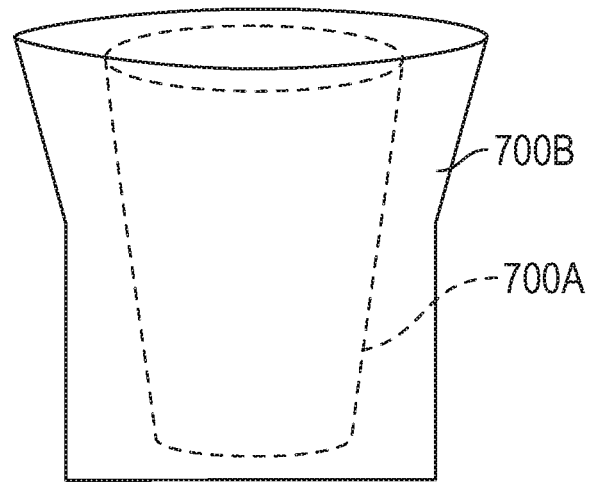

FIGS. 41 and 42 illustrate another embodiment of a frame 700 in which the inflow struts 722 of the first row I at the inflow end 713 define a first angle α between them, and have a first strut width $W_1$. The struts 724 of the second row II define a second angle (3 between them, and have a second strut width $W_2$ (indicated at the third row III in FIG. 41). The struts 726 of the third row III and the struts 728 of the fourth row IV can also define the angle β, and can comprise the second strut width $W_2$. The outflow struts 732 of the fifth row V at the outflow 715 can define a third angle θ, and can comprise the second strut width $W_2$. The angle α can be larger than the angle β, and the angle β can be larger than the angle θ. For example, in certain embodiments the angle α can be 110° to 170°, such as 160°, and the angle β can be 80° to 120°, such as 100°. The angle θ can be can be 40° to 90°, such as 80°. The strut width $W_1$ can be larger than the strut width $W_2$. For example, in certain embodiments the first strut width $W_1$ can be from 0.22 mm to 0.30 mm, such as 0.28 mm, and the second strut width $W_2$ can be from 0.30 mm to 0.36 mm, such as 0.32 mm. Thus, in certain embodiments the first strut width $W_1$ can be 50% to 90% of the second strut width $W_2$, such as 60% to 88% of the second strut width $W_2$. In other embodiments, the frame 700 may comprise an additional row of strut members at the inflow end of the frame configured similarly to the struts 722.

The combination of the larger angle α and the larger strut width $W_1$ can make the inflow struts 722 more resistant to radial expansion than the struts 724-728 of the rows II-IV, which have the angle β and the strut width $W_2$. The struts 724-728, in turn, can be more resistant to radial expansion than the outflow struts 732, which have the angle θ and the strut width $W_2$. This can cause the frame 700 to assume a V-shaped or inverted frustoconical profile when partially expanded, and to assume a Y-shaped configuration when fully expanded, similar to the frame 200 of FIG. 24. This is illustrated in FIG. 42, in which the profile of the partially-expanded frame 700A is shown in dashed lines, and superimposed on the profile of the fully expanded frame 700B.

Figure 43:
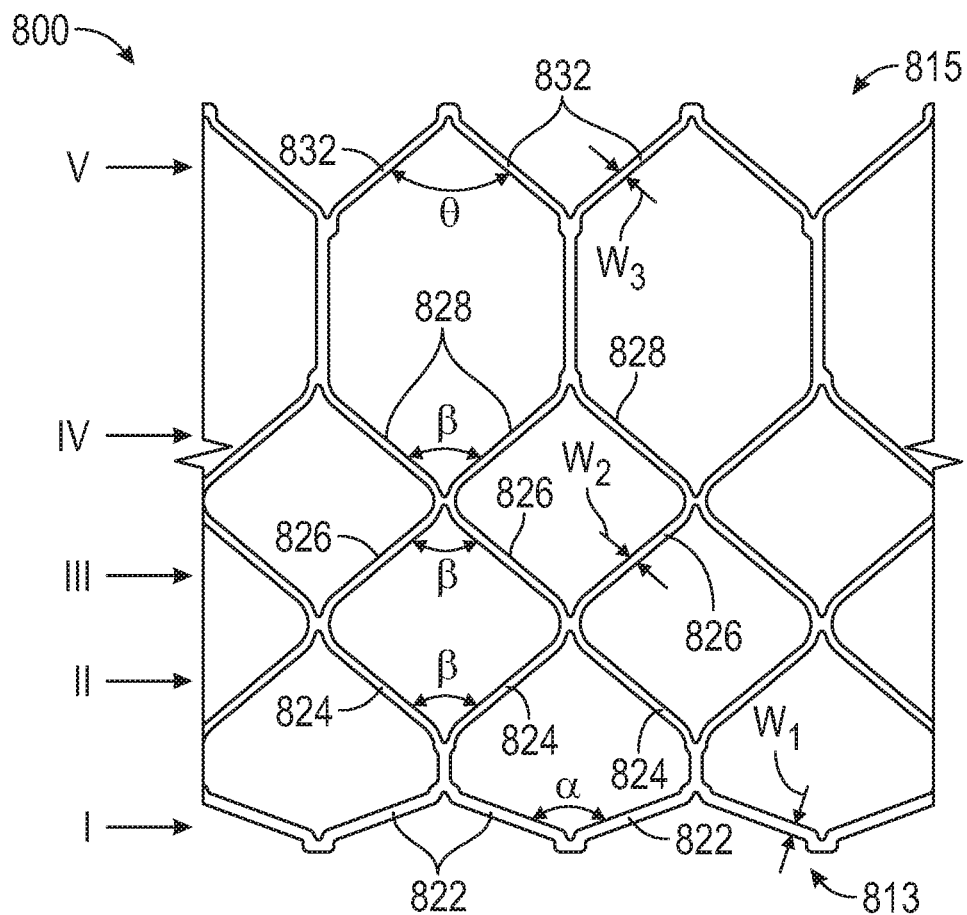
FIGS. 43 and 44 illustrate another embodiment of a frame configured to assume a Y-shape when partially expanded, and to assume a cylindrical shape when fully expanded.
Figure 44:
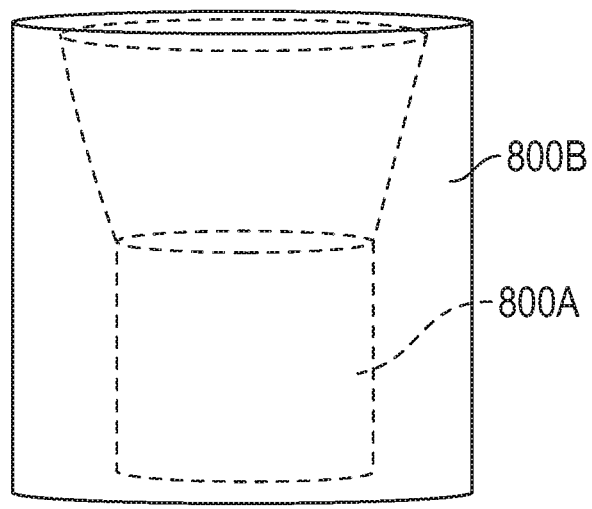

In certain embodiments, the frame of a prosthetic heart valve can be configured to be implantable at various stages of expansion, and/or comprising various cylindrical or non-cylindrical shapes. For example, FIGS. 43 and 44 illustrate another embodiment of a frame 800 in which the inflow struts 822 of the first row I define a first angle α between them, and have a first strut width $W_1$. The struts 824 of the second row II can define a second angle β between them, and can have a second strut width $W_2$ (indicated at the third row III in FIG. 43). The struts 826 of the third row III and the struts 828 of the fourth row IV can also define the angle β, and can comprise the second strut width $W_2$. The outflow struts 832 of the fifth row V can define a third angle θ, and can comprise a third strut width $W_3$. The angle α can be larger than the angle β, and the angle β can be larger than the angle θ. For example, in certain embodiments the angle α can be 110° to 170°, such as 160°, and the angle θ can be 80° to 120°, such as 90°. The angle θ can be can be 40° to 90°, such as 80°. The strut width $W_1$ can be larger than the strut width $W_2$, and the strut width $W_2$ can be larger than the strut width $W_3$. The strut widths $W_1$, $W_2$, and $W_3$, can have any of the values given herein.

The combination of the larger angle α and the larger strut width $W_1$ of the struts 822 can make the inflow struts 822 stronger or more resistant to expansion than the central portion of the frame comprising the struts 824-828. Similarly, the larger angle β and the larger strut width $W_2$ of the struts 824-828 can make the strut rows II-IV more resistant to expansion than the outflow struts 832 due to the smaller angle θ and the smaller strut width $W_3$ of the struts 832. This combination of angles and strut widths can cause the frame 800 to assume a Y-shaped profile when the frame is partially expanded because the outflow end 815 initially expands more quickly than the struts 824-828. The struts 824-828, in turn, can expand more quickly than the inflow struts 822. As the balloon reaches its cylindrical, fully expanded shape, the balloon can become less compliant than the frame such that the shape of the balloon begins to influence or dictate the shape of the frame, including the more rigid inflow struts 822. Thus, as the balloon inflates and becomes more rigid, the frame can conform to the shape of the fully inflated balloon, and can assume a cylindrical shape, or substantially cylindrical shape, in which all strut rows I-V of the frame have approximately the same diameter. This is illustrated in FIG. 44, in which the profile of the partially-expanded frame 800A is shown in dashed lines and superimposed on the profile of the fully expanded frame 800B.

Figure 45A:
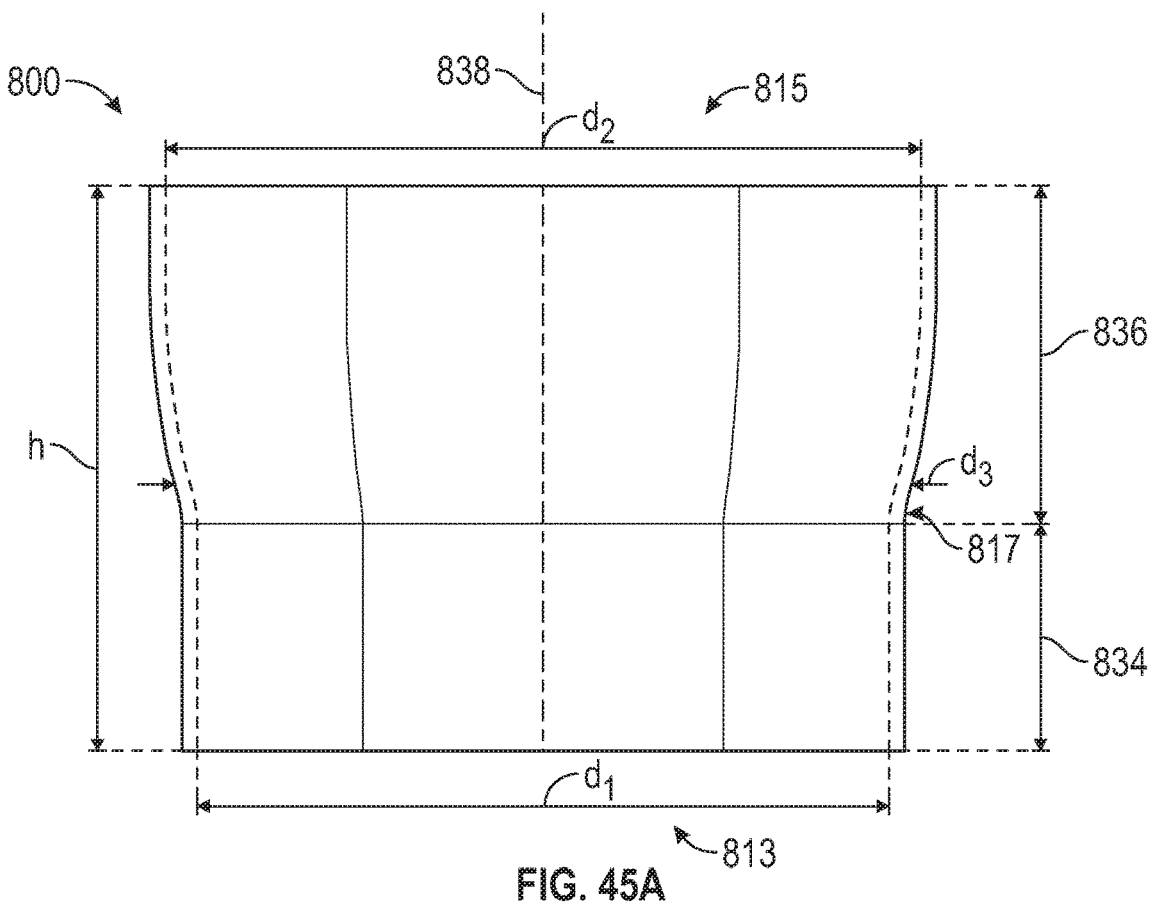
FIG. 45A is a side elevation view schematically illustrating the frame of FIG. 43 in the partially-expanded state.
Figure 46B:
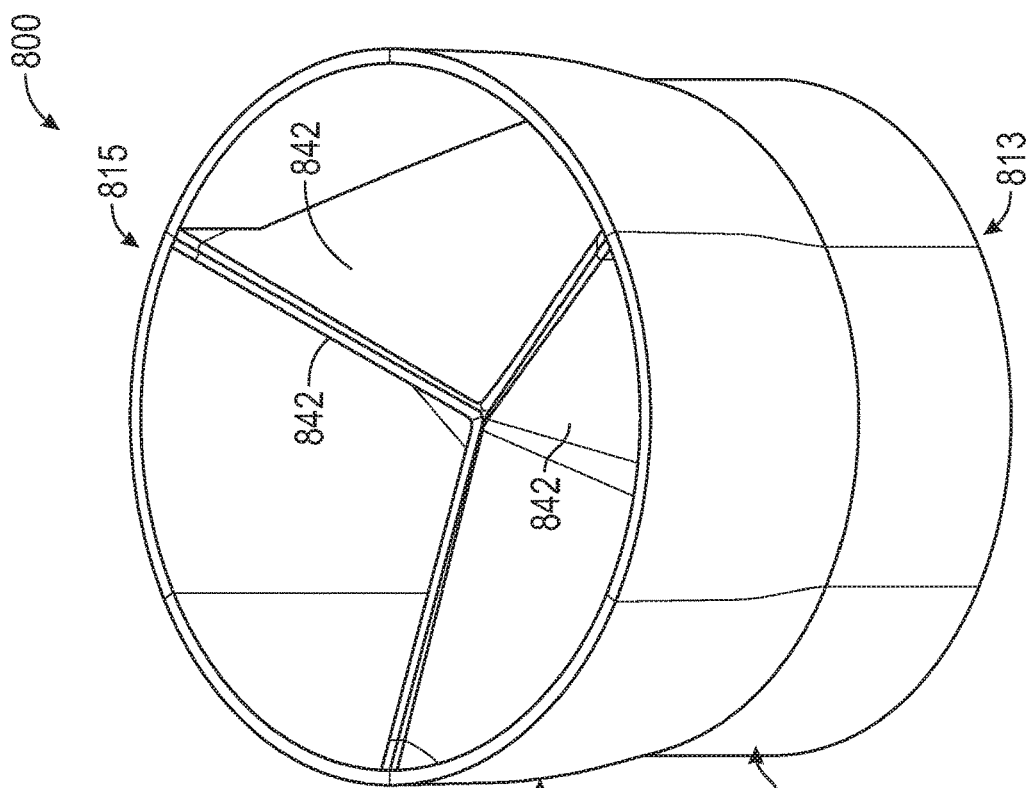
FIGS. 46A and 46B are perspective views of the frame of FIG. 43 in the partially-expanded state illustrating coaptation of the prosthetic valve leaflets.
Figure 46A:
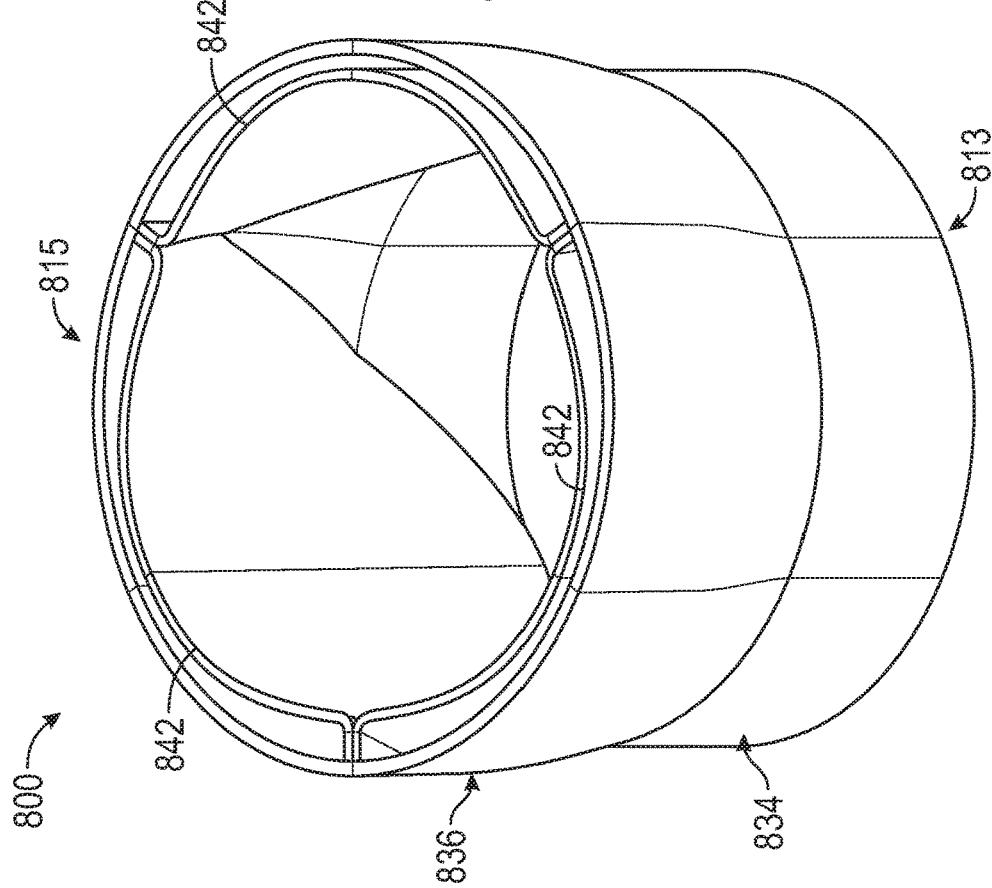

In certain embodiments of prosthetic valves incorporating the frame 800, as the inflow end 815 approaches or reaches the specified design diameter, the leaflets can begin to function to regulate blood flow through the prosthetic valve. In some embodiments, this can be the lower limit of the deployment range in which the prosthetic valve will be sufficiently anchored in the arterial lumen, and can operate substantially as specified. FIG. 45A schematically illustrates the general outline of the frame 800 when partially-expanded to the Y-shaped configuration in which the outflow end 815 has reached the specified design diameter $d_2$. In FIG. 45A, the inflow end 813 has a diameter $d_1$ that is less than the diameter $d_2$. For example, in certain embodiments the diameter $d_2$ can be 2%-30% larger than the diameter $d_1$. The diameter $d_2$ of the outflow end 815 can also be greater than a diameter $d_3$ of a central portion 817 of the frame (e.g., corresponding to about the level of the struts 826 and/or 828). In a particular embodiment in which the frame has a fully-expanded design diameter of 23.5 mm, the diameter $d_2$ can be 23.5 mm, and can be 9% larger than the diameter $d_1$ of 21.5 mm when the frame is partially expanded. With reference to FIGS. 46A and 46B, this can allow the leaflets 842 to coapt normally at the outflow portion 836 even while the inflow portion 834 has a smaller diameter than the outflow portion.

Figure 45B:
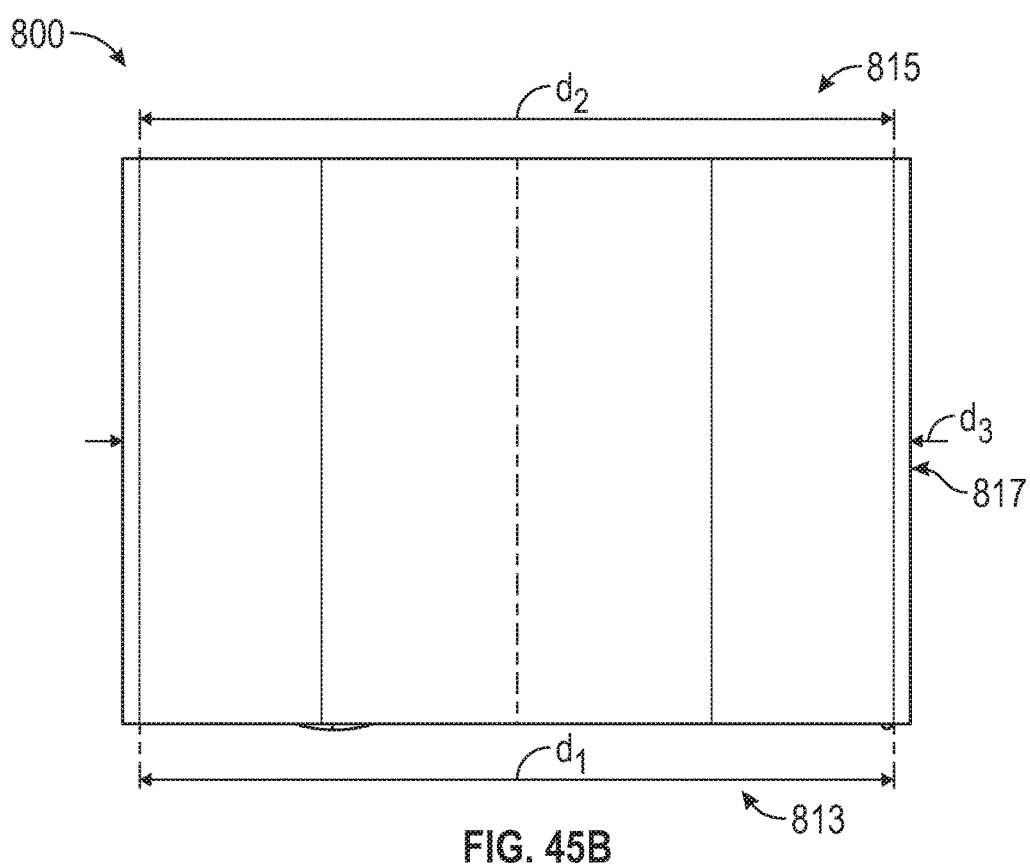
FIG. 45B is a side elevation view schematically illustrating the frame of FIG. 43 in the fully-expanded state.

With reference to FIG. 45B, as the frame is further expanded, the inflow portion 834 can expand to the same diameter as the outflow portion such that $d_1=d_2=d_3$. In some embodiments, this can be the fully expanded configuration of the valve, and the upper limit of the deployment range. As shown in FIG. 45B, in the fully expanded configuration the frame 800 can have a cylindrical shape in which the sides are substantially parallel from the inflow end 813 to the outflow end 815, and the inflow end, the outflow end, and the central portion 817 of the frame have approximately the same diameter.

Referring again to FIG. 45A, the frame 800 can also have a height h measured along the longitudinal axis 838. In certain embodiments, the inflow portion can comprise 30%-

40% of the overall height h, and the outflow portion 836 can comprise 60%-70% of the height h. Thus, in a particular example configured as shown in FIG. 45A in which the height h is 18 mm, the height of the inflow portion 834 can be 40% of h or 7.2 mm, and the height of the outflow portion 836 can be 60% of h or 10.8 mm. In other embodiments, the proportion of the overall height h comprised by the inflow portion and the outflow portion can vary depending upon the particular application and the characteristics desired.

Figures 47, 48A:
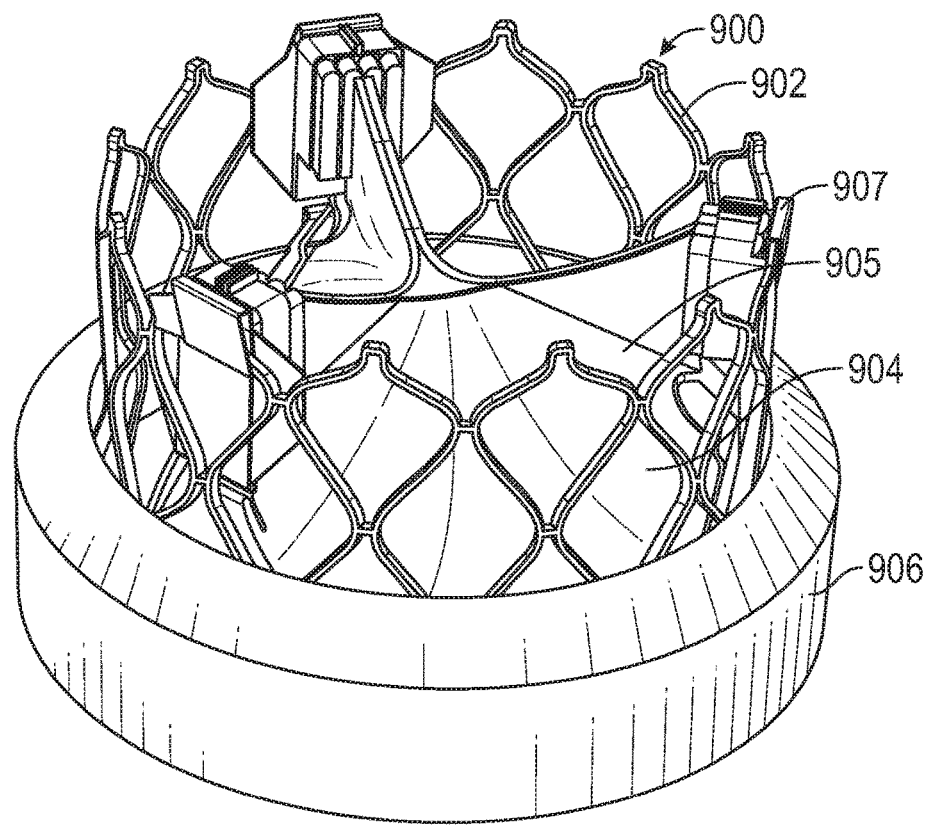
FIG. 47 is a chart illustrating the diameter of the inflow end and the outflow end of the frame of FIG. 43 throughout the deployment range of the frame.
FIGS. 48A and 48B are perspective views of another embodiment of a prosthetic heart valve.

As noted above, the Y-shaped profile of the partially-expanded frame 800 can allow a prosthetic valve incorporating the frame 800 to be implanted at any size within the deployment range where the outflow portion 836 is fully expanded or nearly fully expanded. FIG. 47 is a chart illustrating the diameter range of the inflow portion 834 and the diameter range of the outflow portion 836 leading up to and through the deployment range, in which the prosthetic valve may be implanted with sufficient anchoring and leaflet functionality enabled. As illustrated in FIG. 47, when the outflow portion 836 reaches the full specified design diameter of 23.5 mm, the outflow portion 836 can be sufficiently expanded to anchor the prosthetic valve in a patient for whom a 23.5 mm valve is appropriately sized. The outflow portion 836 can also be sufficiently expanded for the leaflets 842 to coapt normally to control the flow of blood through the prosthetic valve.

As shown in FIG. 47, the prosthetic valve may be implanted with the diameter of the inflow portion 834 anywhere between 21.5 mm (in which the frame has the Y-shaped profile shown in FIG. 45A) to 23.5 mm (in which the frame has the cylindrical profile shown in FIG. 45B). This can allow the physician to implant the prosthetic valve at the configuration that most appropriately balances considerations such as anchoring against the calcified leaflets with the outflow portion 836, force applied to the aortic annulus by the inflow portion 834, and/or proximity of the inflow portion 834 to sensitive anatomical structures. Additionally, when the outflow end 815 is expanded to the specified design diameter, anywhere from 10% to 40% of the overall valve height h can be located in the ventricle, with the remainder of the prosthetic valve being disposed in the native annulus and/or in the atrium.

Below the diameter of 23.5 mm, the frame will also be Y-shaped, but the outflow portion 836 may not be sufficiently large to anchor the prosthetic valve in the patient. The transition from a Y-shape to a parallel shape may occur when the inflow portion reaches the same or nearly the same diameter as the outflow portion. If expanded beyond 23.5 mm, the frame can maintain the cylindrical configuration illustrated in FIG. 47, but the leaflets may not fully coapt at diastole.

Figure 48B:
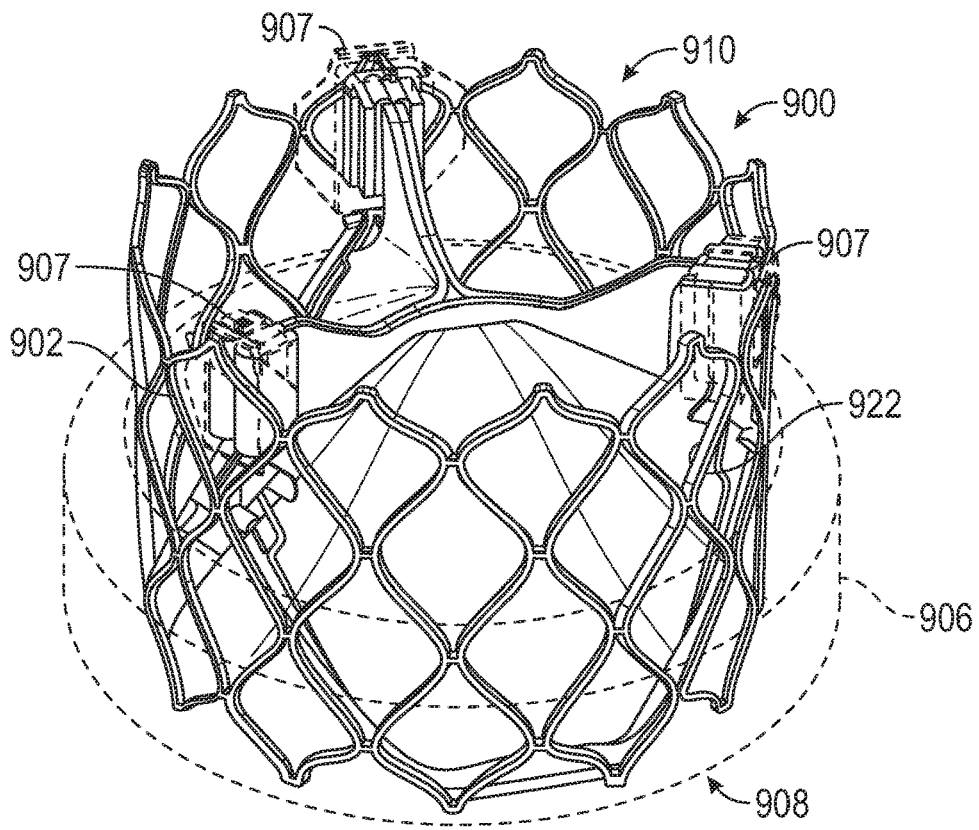
Figure 49:
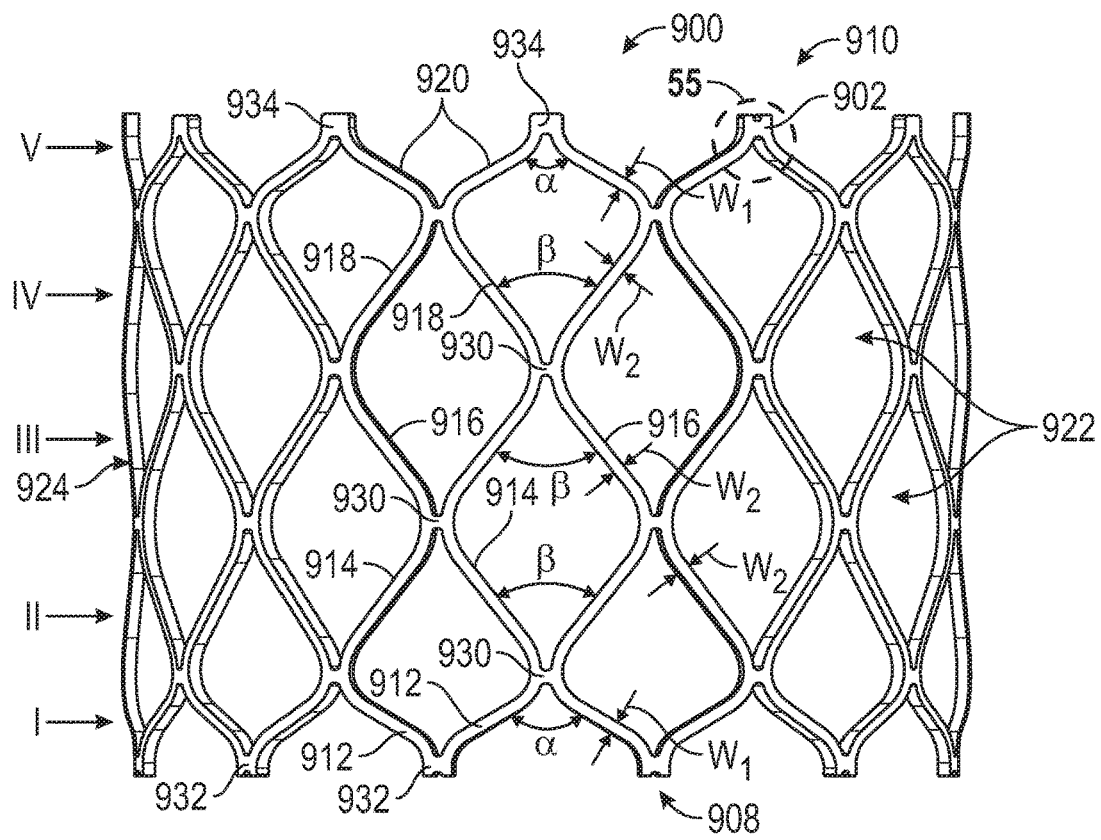
FIG. 49 is a side elevation view of the frame of the prosthetic valve of FIGS. 48A and 48B.

The various strut angle and strut width combinations described herein can also be applied to other frame configurations. For example, FIGS. 48A, 48B, and 49 illustrate another embodiment of a prosthetic heart valve 900. The valve 900 can have three main components: a stent, or frame, 902, a valvular structure 904 situated within and coupled to the frame, and a sealing member 906 positioned around the exterior of the frame. The valvular structure 904 can comprise a plurality of leaflets 905 configured to collapse or coapt in a tricuspid arrangement. The leaflets 905 can be coupled to each other and to the frame at a plurality of commissures 907. Additional details regarding the prosthetic valve 900 and the construction of the commissures 907 can be found in U.S. Publication No. 2018/0028310, which is incorporated herein by reference. FIG. 48B is a perspective view of the prosthetic valve 900 with the components on the outside of the frame 902 (including the sealing member 906) shown in transparent lines for purposes of illustration.

FIG. 49 illustrates the frame 902 in greater detail. The frame 902 can comprise an inflow end 908, an outflow end 910, and a plurality of circumferentially extending rows of angled struts arranged end-to-end to form a plurality of rows or rungs of struts, similar to the embodiments described above. More particularly, the frame can comprise a first or lower row I of struts 912, which can form the inflow end 908 of the frame; a second row II of struts 914 above the first row; a third row III of struts 916 above the second row; a fourth row IV of struts 918 above the third row, and a fifth row V of struts 920 above the fourth row. The struts 920 can form the outflow end 910 of the frame. The various rows of strut can define corresponding rows of cells or openings 922 between the inflow end 908 and the outflow end 910 of the frame.

FIG. 49 illustrates the frame 902 in its initial, as-manufactured state in which the frame has a cylindrical or substantially cylindrical shape, and a constant diameter from the inflow end 908 to the outflow end 910. The struts 912 of the first row I at the inflow end 908 can have a first strut width $W_1$, and can define an angle $\alpha$ between adjacent struts 912. The struts 914-918 of the rows II-IV can have a second strut width $W_2$, and can define a second angle $\beta$ between adjacent struts of the respective rows. The struts 920 of the fifth row V at the outflow end 910 can define the first angle $\alpha$, and can have the first strut width $W_1$, similar to the inflow struts 912. The angle $\alpha$ can be larger than the angle $\beta$, and the strut width $W_1$ can be larger than the strut width $W_2$. For example, in certain embodiments the angle $\alpha$ can be 110° to 170°, such as 120°, and the angle $\beta$ can be 40° to 90°, such as 82°. In certain embodiments, the first strut width $W_1$ can be from 0.30 mm to 0.36 mm, such as 0.32 mm, and the second strut width $W_2$ can be from 0.22 mm to 0.30 mm, such as 0.28 mm.

The larger angle $\alpha$ and the larger strut width $W_2$ can make both the struts 912 of the inflow end 908 and the struts 920 of the outflow end 910 more resistant to radial expansion than the struts 914-918. This particular combination of strut widths and angles can cause the frame 902 to maintain a substantially cylindrical shape as the frame expands, at least within the frame's intended operating diameter range or deployment range. In other words, the frame 902 configured as shown can have a cylindrical profile when partially expanded to a lower end of the deployment range, and can also have a cylindrical profile when fully expanded to the upper bound of the deployment range. This can allow prosthetic valves incorporating the frame 902 to be expanded to a selected diameter within a deployment range of the frame sufficiently to anchor the prosthetic valve in the native arterial lumen and/or to allow the leaflets function properly.

Figure 50:
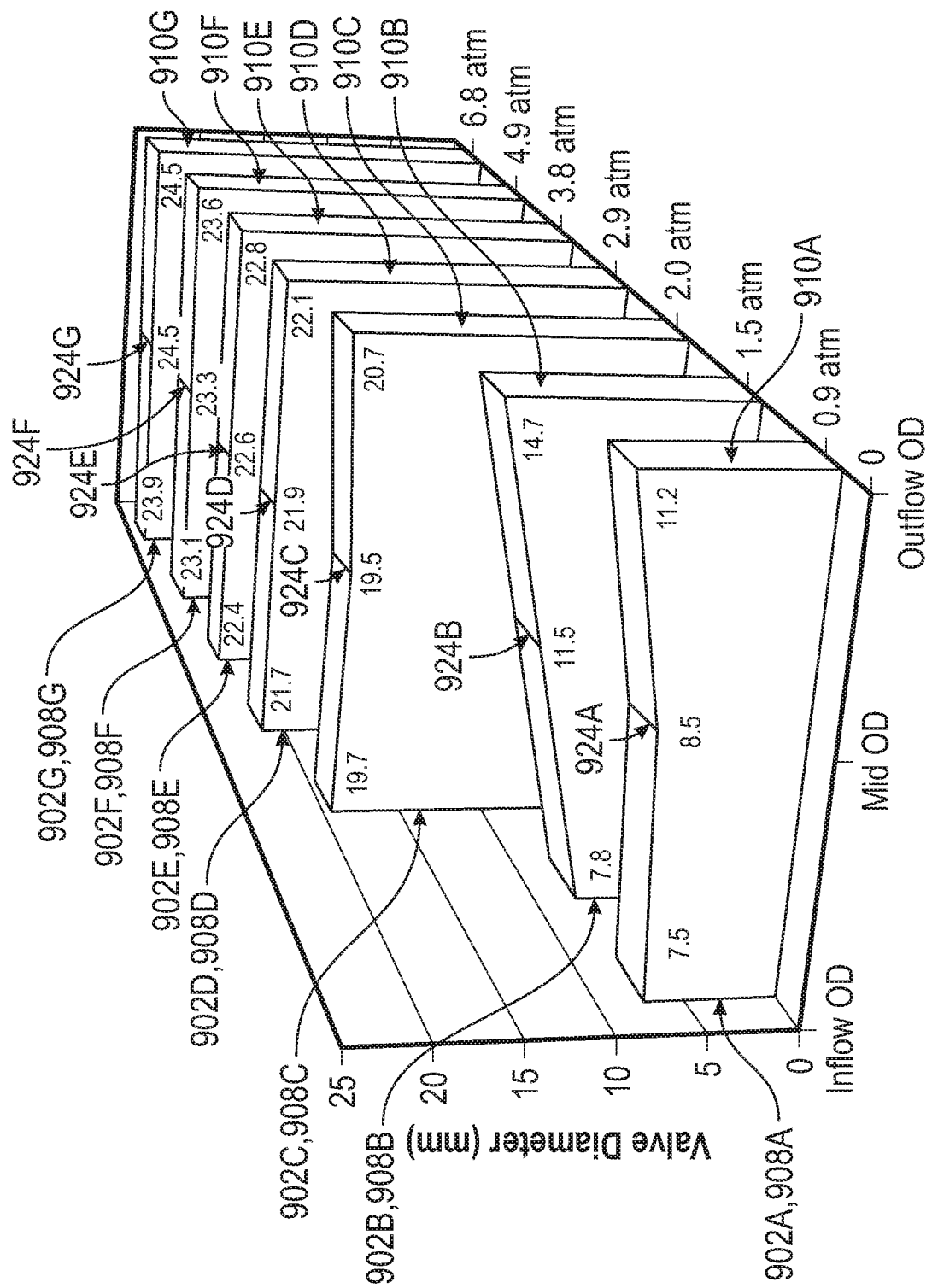
FIG. 50 is a chart illustrating the diameters of the inflow end, the central portion, and the outflow end of the frame of FIG. 49 as the frame is expanded.

For example, FIG. 50 illustrates a series of seven frame sectional profiles 902A-902G representing the diameter of an exemplary frame 902 configured as illustrated in FIGS. 48A, 48B, and 49 at seven different expansion states between the fully crimped state and the fully expanded state. Each frame profile is shown bisected along the longitudinal axis and rotated clockwise such that the inflow ends 908A-908G are on the left side of FIG. 50, and the outflow ends 910A-910G are on the right side of FIG. 50. The seven frame profiles 902A-902E represent the diameters of the inflow ends 908A-908G, the diameters of the outflow ends 910A-910G, and the diameters of central portions 924A-924G. The tested frame 902 had a specified design diameter of 23 mm, and an operating range of 21.5 mm to 23.5 mm. The frame was expanded using a cylindrical balloon similar to the balloon 114 of FIG. 21. The frame diameter measurements were taken at seven different internal balloon pressures corresponding to different levels of inflation or expansion of the balloon. The frame profile 902A represents the state of the frame shortly after inflation of the balloon began, and the frame had been slightly expanded from the fully crimped state. The frame profile 902G represents the state of the frame after the balloon was fully inflated. The profiles 902B-902F represent intermediate expansion states of the frame between 902A and 902E. Diameter measurements were made at three different angular orientations within the frame for each expansion state.

The measured diameter of each of the portions 908A-908G, 910A-910G, and 924A-924G are given in millimeters for each of the frame profiles 902A-902G. The pressure inside the balloon is given to the right of each frame profile for each expansion state. Thus, for example, at a balloon pressure of 0.9 atmospheres (atm), the inflow end 908A of the frame represented at 902A had a diameter of 7.5 mm, the central portion 924A had a diameter of 8.5 mm, and the outflow end 910A had a diameter of 11.2 mm. At this point in the expansion process, the frame had a substantially Y-shaped profile, wherein the diameter of the central portion 924A was only slightly larger than the diameter of the inflow end 908A, and smaller than the diameter of the outflow end 910A.

Still referring to FIG. 50, the frame 902 transitioned from a Y-shaped profile to a V-shaped profile at 902B as the outflow end 910B expanded more quickly than the inflow end 908B and more quickly than the central portion 924B at a balloon pressure of 1.5 atm. The frame 902 transitioned back to a slight Y-shaped profile at 902C at a balloon pressure 2.0 atm. Between the frame profile 902C and the profile 902D, the frame reached the lower end of the operating range (21.5 mm). At frame profile 902D, with a balloon pressure of 2.9 atm, the inflow end 908D had a diameter of 21.7 mm, the central portion 924D had a diameter of 21.9 mm, and the outflow end 910D had a diameter of 22.1 mm, making the frame substantially cylindrical. The frame remained substantially cylindrical throughout the rest of the expansion process up to a balloon pressure of 6.8 atm at frame profile 902G, without a difference of more than 0.6 mm between any of the inflow end, the outflow end, or the central portion, due at least in part to the particular strut width and strut angle configuration of the frame.

In certain embodiments, the leaflets 905 of the prosthetic valve 900 can be configured to open and close appropriately in order to maintain a specified pressure gradient across the prosthetic valve at any diameter within the deployment range. This can provide significant advantages over existing prosthetic valves, which are often designed to function at a particular specified diameter, because the physician can determine an optimum diameter of the frame at which to implant the prosthetic valve during the implantation procedure. More specifically, the physician can expand the frame to a selected diameter within the prosthetic valve's operating range that facilitates anchoring the prosthetic valve and optimizes hydrodynamic performance, while balancing constraints imposed by a particular patient's anatomy or risk factors. Maintaining a cylindrical shape, or a substantially cylindrical shape, throughout the operating range can also improve the hemodynamics or transvalvular flow characteristics since the flow restrictions due to narrow diameter portions of the frame can be minimized.

Figure 51:
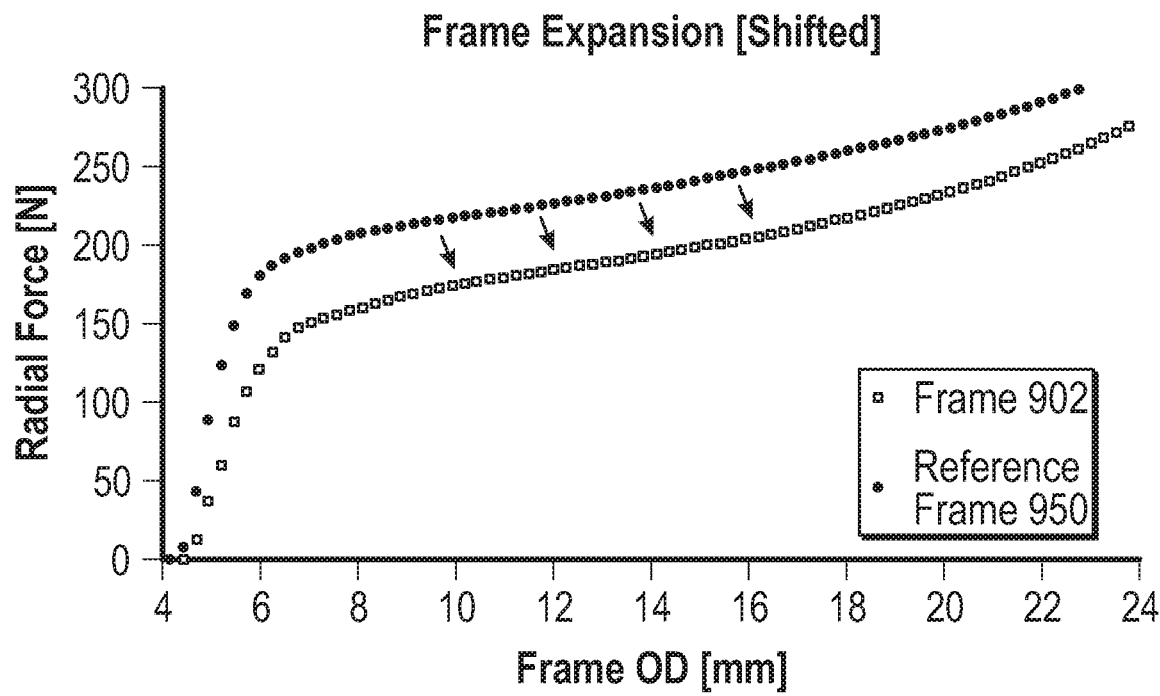
FIG. 51 is a graph illustrating the radial force required to expand the frame of FIG. 49 as a function of frame diameter, and the radial force required to expand a reference frame.

The greater width $W_1$ at the inflow and outflow ends of the frame, in combination with the greater strut angle α, can make the inflow and outflow portions of the frame relatively stronger and more resistant to radial expansion, as described above. This can make the struts of the rows II-IV relatively less resistant to expansion, reducing the force required to expand these struts relative to the struts of rows I and V. In the case of balloon expandable frames, in which the prosthetic leaflets are typically positioned between the balloon and the frame when the prosthetic valve is mounted on a delivery catheter, this may result in relatively lower forces applied by the balloon against the leaflets. For example, FIG. 51 is a graph illustrating expansion of a frame configured as shown at FIGS. 48A-49 (plotted using open circles) and expansion of a reference frame 950 without the different strut widths and strut angles. As shown in FIG. 51, the radial force exerted by the balloon against the leaflets may be reduced by 50 N or more between an outer diameter of 6 mm and an outer diameter of 23 mm for the frame 902 as compared to the reference frame 950. This can be due at least in part to the different strut widths and strut angles of the frame 902. In certain embodiments, this force reduction can allow the leaflets to unfold to a greater degree as the frame is expanded as compared to existing frames with equal strut widths.

Figure 52:
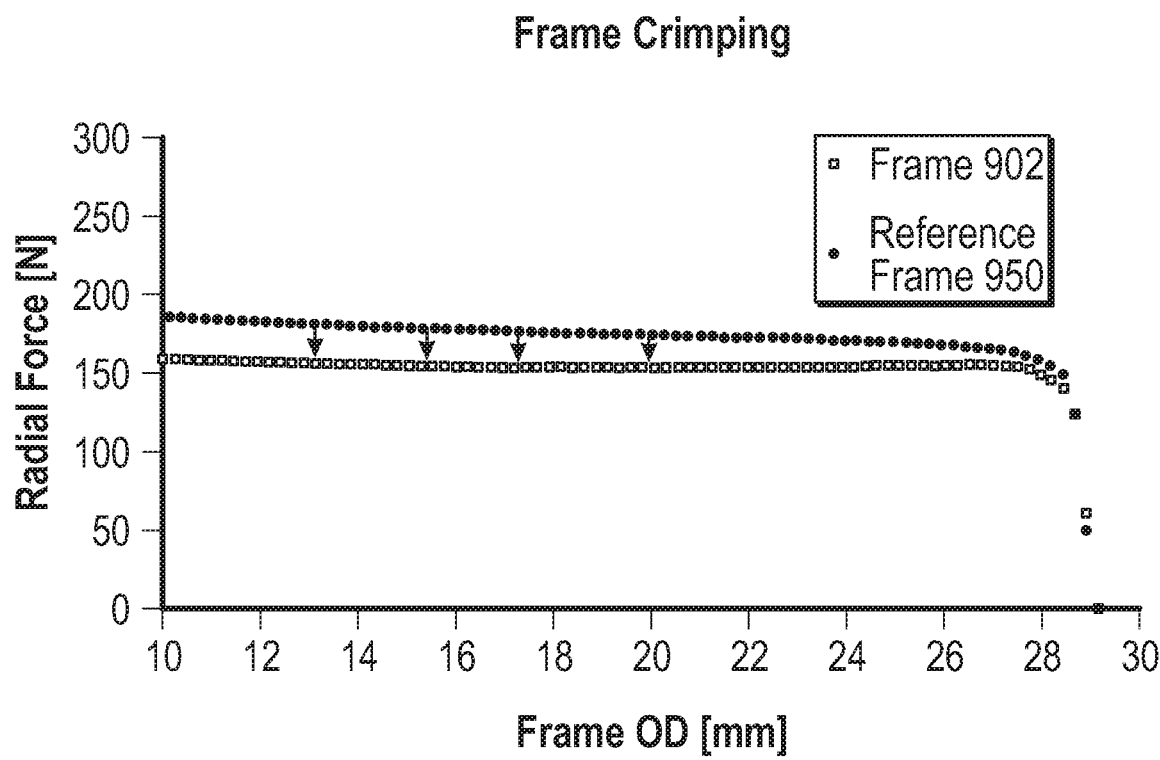
FIG. 52 is a graph illustrating the radial force required to crimp the frame of FIG. 49, and the radial force required to crimp a reference frame.

The force required to crimp the frame may also be reduced, as shown in FIG. 52. In FIG. 52, the force required to crimp the frame 902 may be reduced by 25 N or more between a diameter of 28 mm and a diameter of 10 mm. Additionally, between a diameter of 29 mm and 28 mm, the frame 902 and the reference frame 950 exhibit approximately equal stiffness, and deform by a nearly equal amount per unit of radial force applied. Thus, at least for diameters between approximately 28 mm and 29 mm, the frame 902 exhibits comparable stiffness to the reference frame 950, and will hold its shape and anchor the frame against the surrounding anatomy with minimal deformation. The frame 902 thereby exhibits reduced stiffness in expansion compared to the reference frame, with the attendant benefits, but maintains a comparable degree of stiffness in response to compressive force, allowing the frame 902 to maintain its size and shape once expanded to its deployment diameter range.

Figure 53:
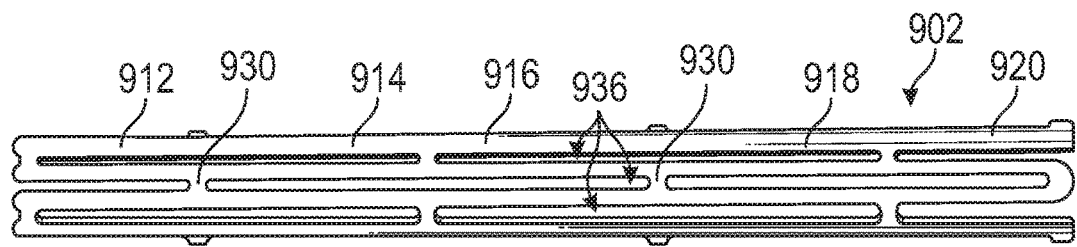
FIG. 53 is a side elevation view of the frame of FIG. 49 crimped to a radially collapsed configuration.
Figure 54:
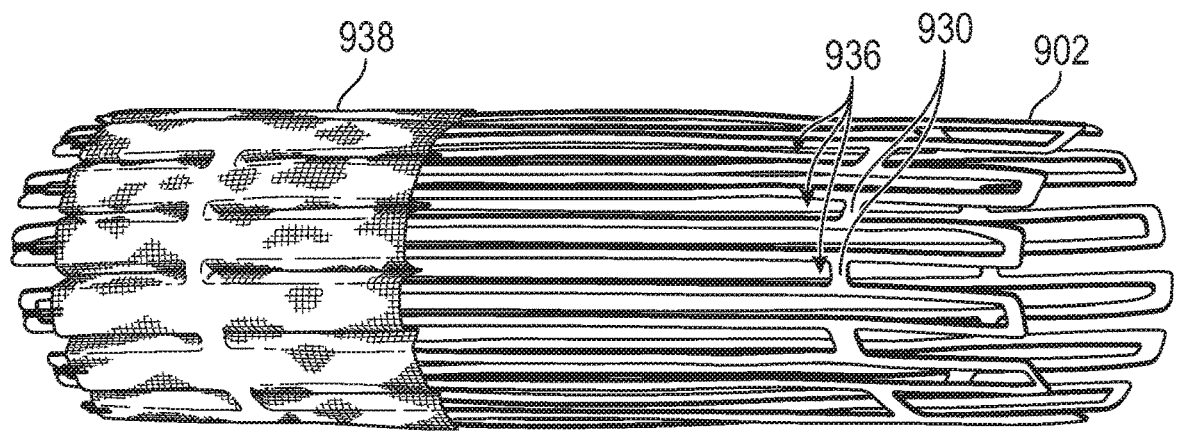
FIG. 54 is a perspective view of the frame of FIG. 49 crimped to the collapsed configuration and including an outer skirt, with portions of the skirt shown disposed in gaps between struts of the frame.

The frame 902 can also be configured to provide gaps between adjacent struts when the frame is crimped. For example, referring again to FIG. 49, the frame can include junctions 930 configured as strut portions extending between adjacent strut members at the shortest distance between the struts (e.g., at the location of two struts from one row converging with two struts of an adjacent row). The apices 932 at the inflow end of the frame and/or the apices 934 at the outflow end of the frame can also be relatively wide (e.g., in the circumferential direction). In this manner, the apices 932 and 934, in cooperation with the junctions 930, can space apart the struts when the frame is crimped to form gaps, openings, or spaces 936, as shown in FIG. 53. Referring to FIG. 54, when the frame is crimped for delivery, the outer skirt 938 can be at least partially received or packed in the gaps 936, which can reduce the diameter of the crimped prosthetic valve. In certain embodiments, the skirt, the leaflets, and/or other components of the prosthetic valve can determine the minimum crimping diameter, and thus the gaps 936 may be optimized to receive such materials without significantly increasing the valve's crimped profile.

Figure 55:
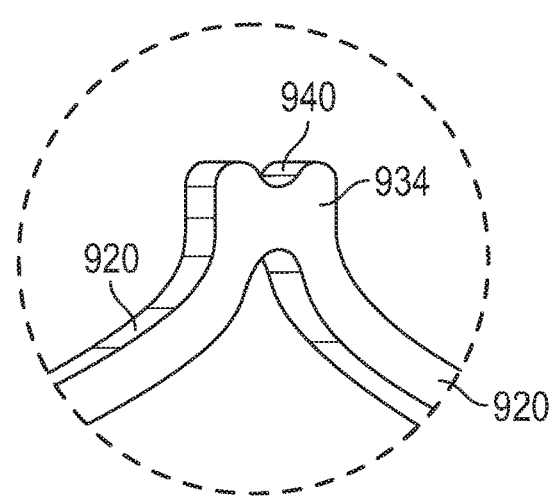
FIG. 55 is a magnified perspective view of an apex of the frame of FIG. 49.

With reference to FIG. 55, in certain embodiments one or more of the apices 932 and/or the apices 934 can comprise a notch or recess 940 configured to receive or guide sutures.

FIG. 55 shows a representative apex 934 for purposes of illustration. The notches 940 can assist in retaining sutures used to attach the leaflet commissures to the frame, and/or to attach inner and/or outer perivalvular leakage (PVL) skirt(s) to the frame. Further details regarding attachment of commissures to the frame can be found in U.S. Publication No. 2018/0028310, which is incorporated herein by reference.

The frame illustrated in FIGS. 48A-49 can also be configured to form other shapes during expansion, and/or when fully expanded, such as the Y-shaped profiles, barrel-shaped profiles, V-shaped profiles, etc., described above. These shapes can be achieved at various stages of expansion by tuning the strut width and angle parameters at different parts of the frame, as described above.

Figure 56:
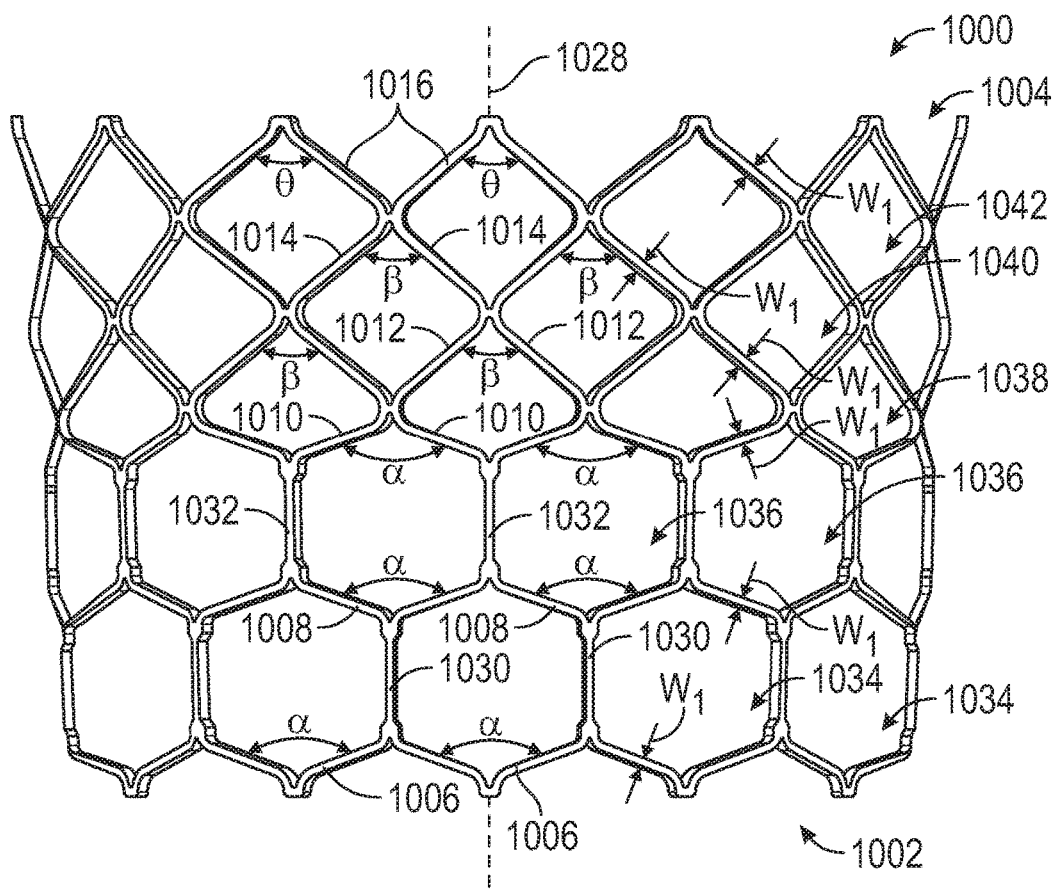
FIG. 56 is a side elevation view of another embodiment of a frame of a prosthetic heart valve in the as-manufactured state.

The various strut angle and strut width combinations described herein can also be applied to frames having any number of rows of struts. For example, the strut angle and strut width combinations can be applied to frames having fewer than five rows of struts, such as four rows or three rows of struts, or frames having more than five rows of struts, such as six rows or seven rows of struts. For example, FIG. 56 illustrates another embodiment of a frame 1000 comprising an inflow end 1002, an outflow end 1004, and six rows of circumferentially-extending struts. In the illustrated embodiment, struts 1006 are located at the inflow end 1002, followed by struts 1008, 1010, 1012, 1014, and struts 1016 located at the outflow end 1004. The struts 1006 can be spaced apart from the struts 1008 along the longitudinal axis 1028 of the frame by axially-extending struts 1030. The struts 1008, in turn, can be longitudinally spaced apart from the struts 1010 by axially-extending struts 1032. In this manner, the struts 1006, 1008, and 1030 can define a circumferentially extending row of hexagonal openings 1034 at the inflow end 1002, and the struts 1008, 1010, and 1032 can form a circumferentially extending row of hexagonal openings 1036 above the openings 1034. The remaining struts 1010-1016 can define three rows of circumferentially-offset, diamond-shaped openings 1038-1042 similar to the frame 902 of FIG. 49.

Figure 57:
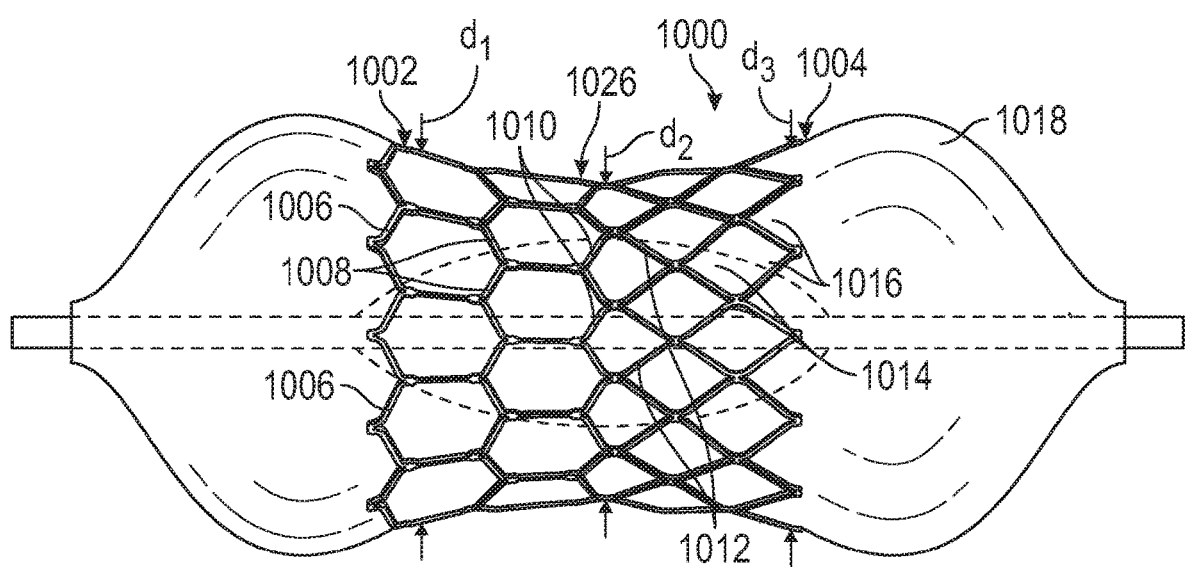
FIG. 57 illustrates the frame of FIG. 56 in a partially-expanded state on a balloon.

The frame 1000 can comprise strut angles and strut widths similar to the frame 200 of FIG. 19. For example, the struts 1006-1010 can all comprise an angle α, and the struts 1012-1014 can comprise an angle β. The outflow struts 1016 can comprise an angle θ. As in the embodiment of FIG. 19, the angle α can be larger than the angle β, and the angle β can be larger than the angle θ. Additionally, as in the embodiment of FIG. 19, all of the struts can comprise the same strut width $W_1$. Accordingly, when the frame 1000 is crimped onto a balloon and expanded by inflating the balloon, the frame can assume an hourglass shape when partially expanded, and a Y-shape when fully expanded. FIG. 57 illustrates the frame 1000 in the partially expanded state on a balloon 1018. In the partially expanded state, the inflow and outflow ends may expand at different rates, such that a diameter $d_1$ of the inflow end 1002 is smaller than a diameter $d_3$ of the outflow end 1004, but larger than the diameter of the central portion 1026 between the inflow and outflow ends (e.g., corresponding approximately to the level of the struts 1010).

Figure 58:
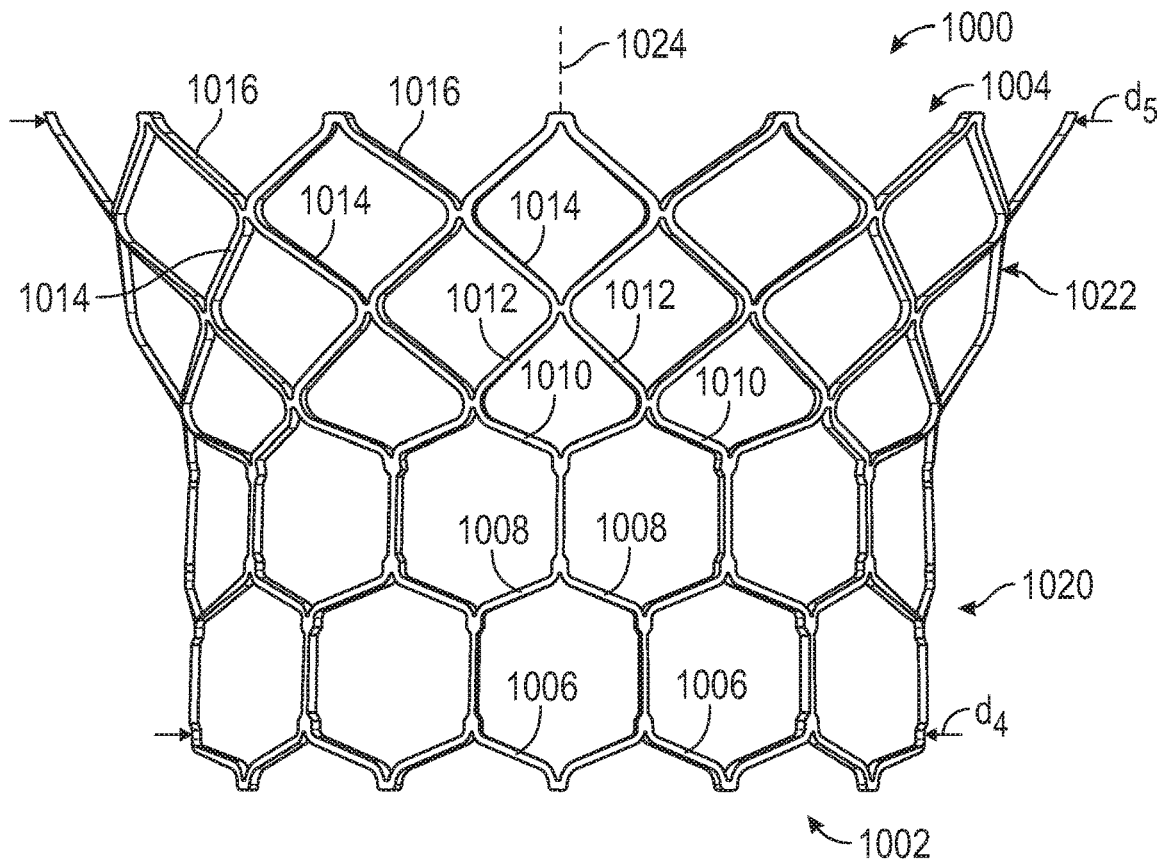
FIG. 58 is a side elevation view of the frame of FIG. 56 in the fully-expanded state.

With reference to FIG. 58, when fully expanded the frame 1000 can have a Y-shaped profile similar to the expanded frame 200. In certain embodiments, the frame 1000 can comprise a cylindrical inflow portion 1020 and a flared outflow portion 1022. In the illustrated configuration, the struts 1006, 1008, and 1010 can form the cylindrical inflow portion 1020, which can have a diameter $d_4$. The struts 1012-1016 can form the flared outflow portion 1022, and can be angled outwardly away from the central axis 1024 of the frame such that the outflow end 1004 has a diameter $d_5$ that is larger than the diameter $d_4$.

Figure 59:
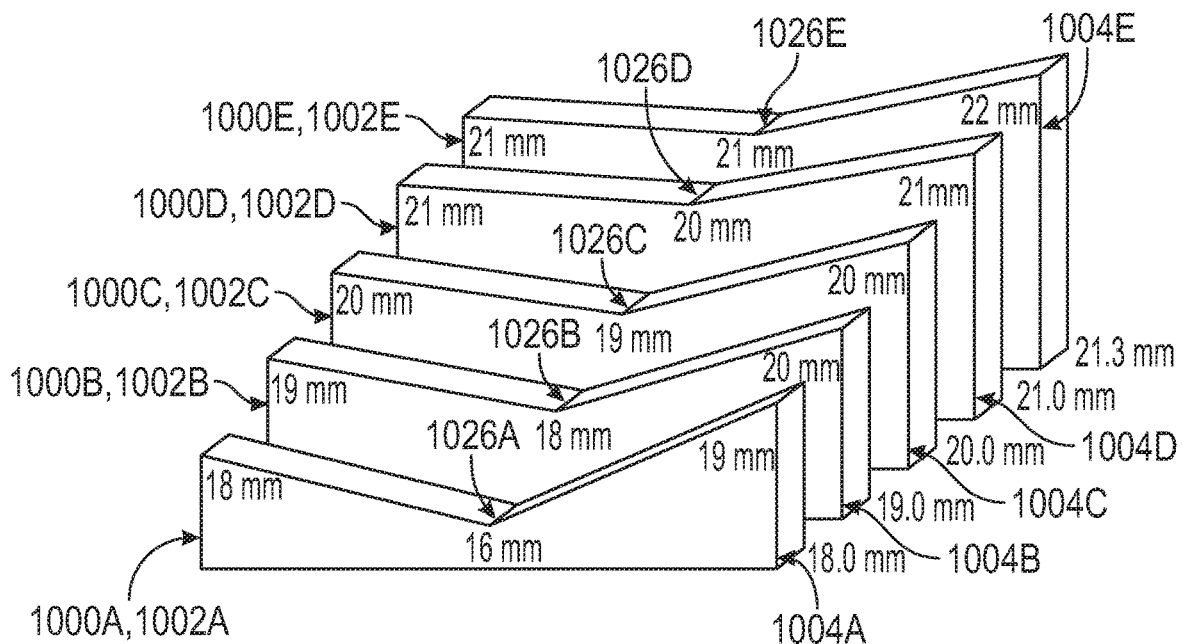
FIG. 59 is a chart illustrating the diameters of the inflow end, the central portion, and the outflow end of the frame of FIG. 56 as the frame is expanded.

FIG. 59 illustrates a series of five frame half-profiles 1000A-1000E representing the shape of an exemplary frame 1000 configured as illustrated in FIG. 56 at five different expansion states between the fully crimped state and the fully expanded state. Each frame profile is shown bisected along the longitudinal axis and rotated clockwise such that the inflow ends 1002A-1002E are on the left side of FIG. 59, and the outflow ends 1004A-1004E are on the right side of FIG. 59. The five frame profiles 1000A-1000E represent the diameters of the inflow ends 1002A-1002E, the diameters of the outflow ends 1004A-1004E, and the diameters of the central portions 1026A-1026E. The tested frame 1000 had an as-manufactured diameter of 20 mm, and was expanded using a balloon similar to the balloon 1018 of FIG. 57. The frame diameter measurements were taken at five balloon diameters corresponding to different levels of inflation or expansion of the balloon. The frame profile 1000A represents the state of the frame shortly after inflation of the balloon began, and the frame had been slightly expanded from the fully crimped state. The frame profile 1000E represents the state of the frame after the balloon was fully inflated. The profiles 1000B-1000D represent intermediate expansion states of the frame between 1000A and 1000E.

The measured diameter of each of the portions 1002A-1002E, 1004A-1004E, and 1026A-1026E are given in millimeters for each of the frame profiles 1000A-1000E. The diameter of the balloon as measured adjacent the inflow end 1002 of the frame is given to the right of each frame profile 1000A-1000E for each expansion state. Thus, for example, at a balloon diameter of 18 mm, the inflow end 1002A of the frame 1000A had a diameter of 18 mm, the central portion 1026A had a diameter of 16 mm, and the outflow end 1004A had a diameter of 19 mm. At this point in the expansion process, the frame had a substantially hourglass-shaped profile, wherein the diameter of the central portion 1026A was less than the diameters of both the inflow end 1002A and the outflow end 1004A.

Still referring to FIG. 59, the frame 1000 gradually transitioned from an hourglass-shaped profile to a Y-shaped profile as the frame expanded due to the particular strut width and strut angle configuration of the frame. For example, when the balloon was fully expanded to its specified design diameter of 21.3 mm, the inflow end 1002E of the frame profile 1000E had a diameter of 21 mm, the central portion 1026E also had a diameter of 21 mm, and the outflow end 1004E had a diameter of 22 mm. Thus, the frame was substantially cylindrical between the struts 1006 (FIG. 56) and about the level of the struts 1010, and flared away from the central axis of the frame between the struts 1010 and the struts 1016 at the outflow end such that the frame had a Y-shaped profile.

Figure 60:
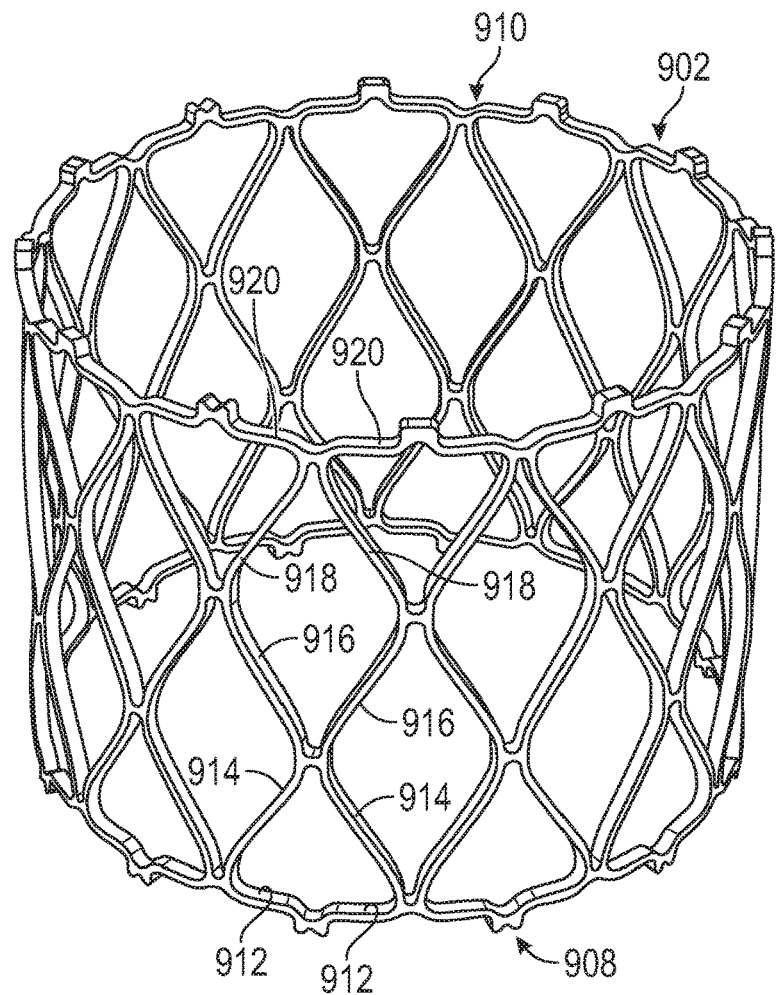
FIG. 60 is a perspective view of another embodiment of a frame for a prosthetic heart valve.
Figure 61:
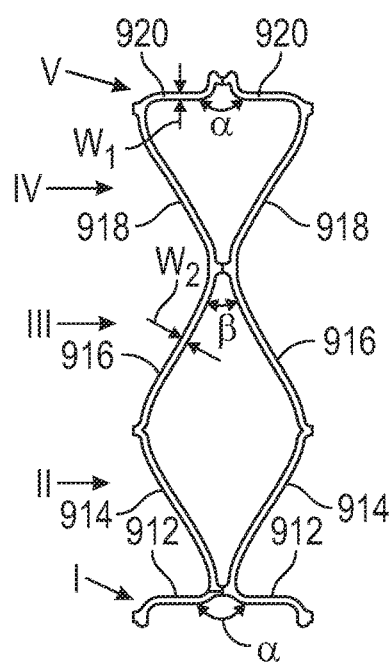
FIG. 61 is a side elevation view of a portion of the frame of FIG. 60.

FIGS. 60 and 61 illustrate another embodiment of the frame 902 in which the inflow struts 912 of the first row I and the outflow struts 920 of the fifth row V comprise an angle α of 180° when the frame is expanded. In other words, the inflow struts 912 can be co-planar, or substantially co-planar, when the frame is expanded, and the struts 920 can be co-planar, or substantially co-planar, when the frame is expanded. An angle of 180° between the inflow struts and between the outflow struts can make the struts relatively stiffer or more resistant to radial expansion as noted above. At or near an angle of 180°, further expansion of the inflow and outflow ends of the frame can be significantly impeded by the struts 912 and 920. Such a large angle can also reduce the amount of radial contraction of the inflow and outflow ends of the frame, as may occur when the balloon is deflated and the frame relaxes and deflects radially inwardly.

The amount by which a frame radially contracts upon deflation of the balloon can be related to the specified design angle between the struts. For example, for frames, or portions thereof, where the angle formed between adjacent struts is relatively low, relaxation of the struts as the balloon deflates can cause the struts to move or pivot toward one another, reducing the angle between them. This, in turn, can reduce the diameter of the frame. Where the struts form an angle of 180° at the specified design diameter, relaxation or elastic strain recovery of the struts can be primarily in the circumferential direction, resulting in a reduced angle change (e.g., a reduced angle decrease) between adjacent struts as the balloon deflates. This can result in a smaller overall radial contraction of the frame. In certain examples, the angle change between the struts when the balloon is inflated and when the balloon is deflated can be approximated by the small angle approximation. In other words, in certain embodiments, the difference in the angle between adjacent struts when the balloon is inflated and when the balloon is deflated can be relatively small such that the resultant frame diameter change is negligible (e.g., 1 mm, 0.5 mm, 0.1 mm, or less).

Figure 62:
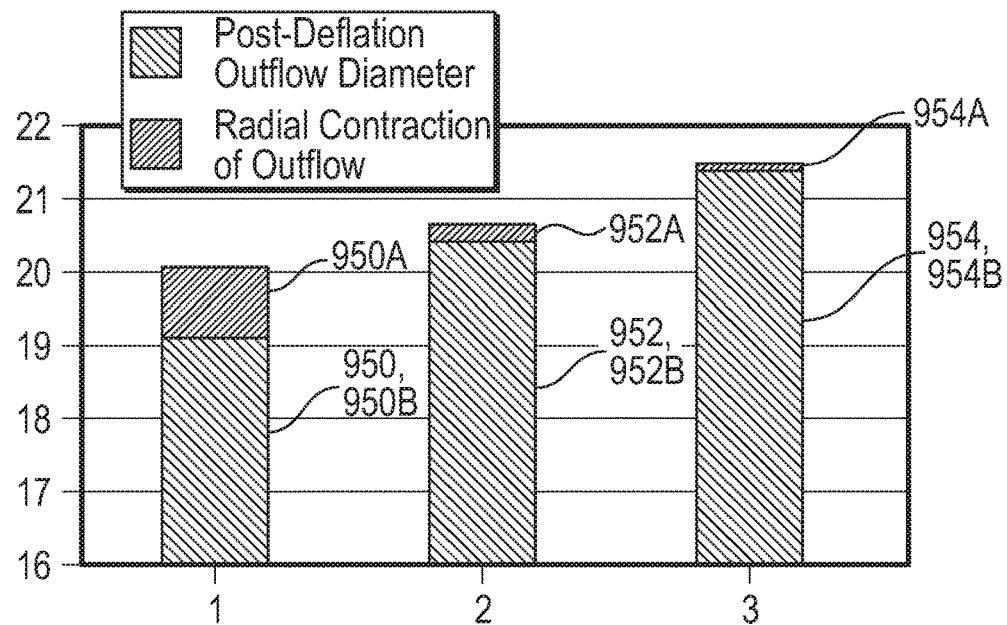
FIG. 62 is a bar chart illustrating the amount by which the outflow end of the frame of FIG. 60 radially contracts when the expansion balloon is deflated as a proportion of the overall diameter of the outflow end.

For example, FIG. 62 is a bar chart illustrating the proportion of the overall diameter of the outflow end of the frame 902 that may be lost to radial contraction or elastic strain recovery when the balloon deflated. Although the following examples are given with respect to the outflow end of the frame, similar performance may be achieved with regard to the inflow end of the frame when configured as described above. Examples are given for frames that were expanded to 20.1 mm at bar 950, 20.6 mm at bar 952, and 21.5 mm at bar 954. Referring to bar 950, when the frame 902 was expanded to around 20 mm and the balloon was deflated, the diameter of the outflow end of the frame was reduced by approximately 1 mm, represented by portion 950A of the bar 950. Thus, post-deflation, the diameter of the outflow end of the frame was 19.1 mm, represented by portion 950B.

Referring to bar 952, when a frame 902 was expanded to 20.6 mm, the angle α between the outflow struts 920 was increased as compared to the frame of bar 950. Thus, when the balloon was deflated, the diameter of the outflow end was reduced by approximately 0.2 mm due to radial contraction (represented by portion 952A) to a diameter of 20.4 mm (represented by portion 952B). Referring to bar 954, when a frame 902 was expanded to 21.5 mm, the angle α between the outflow struts 920 was at or near 180°. As a result, when the balloon was deflated, the diameter of the outflow end of the frame was reduced by approximately 0.1 mm (represented by portion 954A) to a diameter of approximately 21.4 mm (represented by portion 954B). Thus, designing the frame with an angle α of 180° at the outflow end (and/or at the inflow end), and expanding the frame such that the outflow struts approach or reach 180°, can significantly reduce the amount of diameter reduction at the outflow end of the frame attendant to deflating the balloon.

Figure 63:
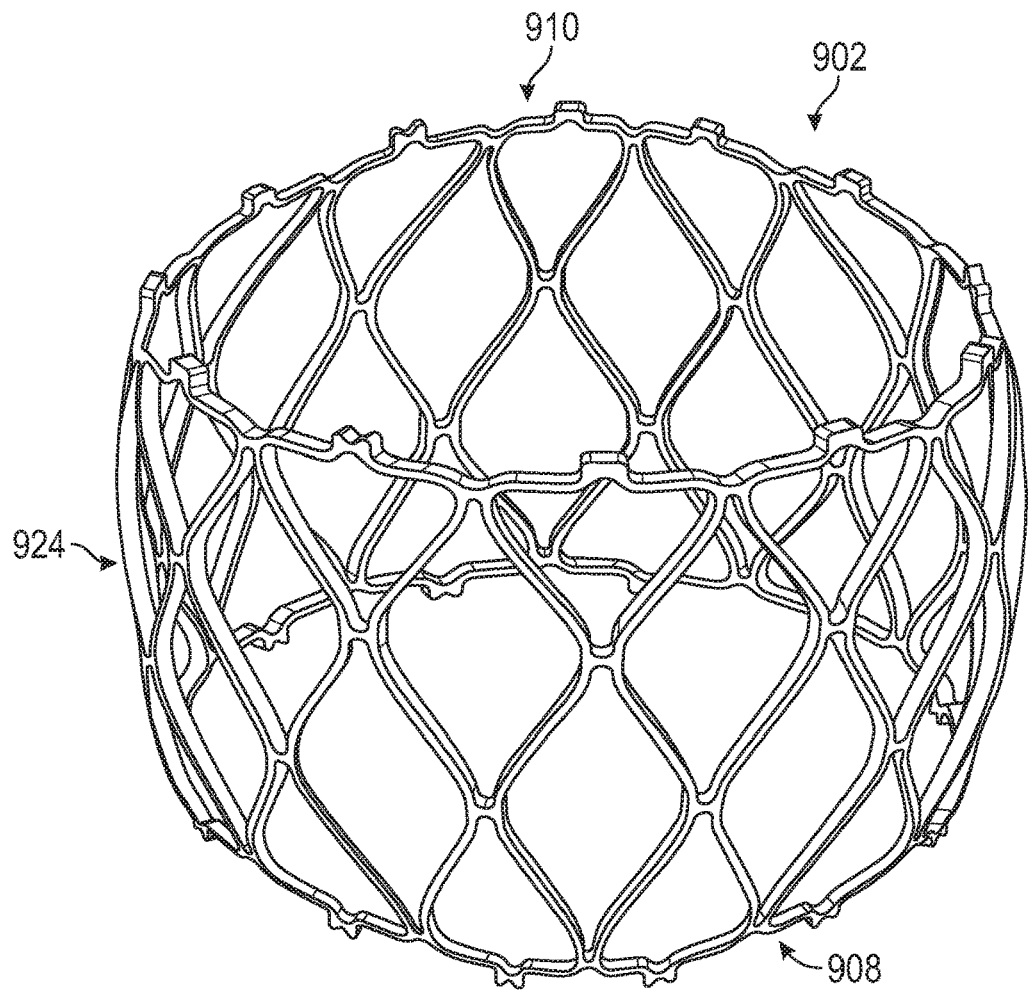
FIG. 63 is a perspective view of the fully expanded frame of FIG. 60 exhibiting a barrel-shaped profile.

In certain embodiments, when the inflow and outflow ends of the frame have expanded to the design diameter (e.g., wherein the angle α between adjacent inflow struts and between adjacent outflow struts is substantially 180°), the struts of rows II-IV may continue to expand. Referring to FIG. 63, this may result in a barrel-shaped outer frame profile when the balloon is deflated, in which the diameter of the central portion 924 of the frame midway along its longitudinal axis is greater than the diameter of the inflow end 908 and/or of the outflow end 910.

Figure 64A:
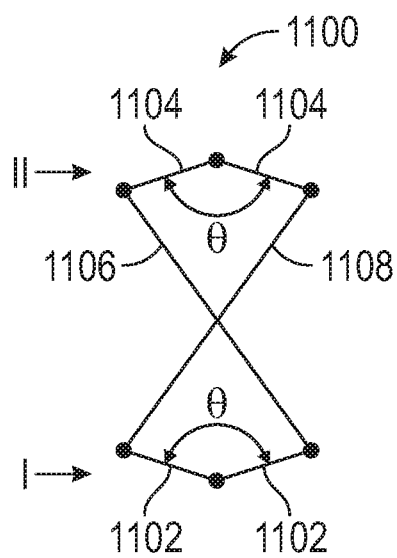
FIGS. 64A-64D are schematic diagrams of various strut configurations for prosthetic heart valve frames.
Figure 64B:
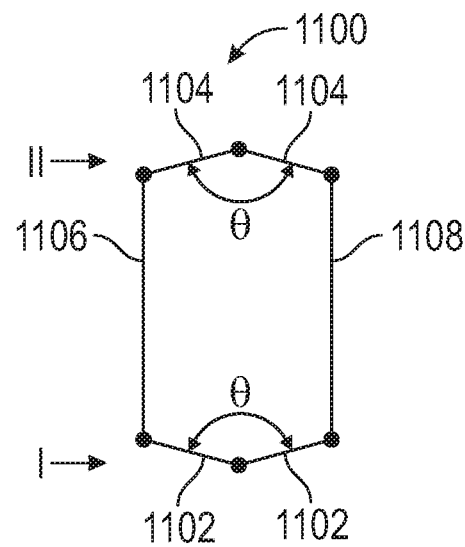

FIGS. 64A-64D schematically illustrate a variety of frame strut configurations or unit cells incorporating one or more rows of struts with relatively large strut angles. Such rows of struts can be used to define the expanded shape of a frame by limiting expansion of the frame beyond a specified diameter, and/or restricting radial contraction of the frame upon removal of an expansion device, such as a balloon. FIGS. 64A and 64B illustrate strut patterns configured for use at the inflow end of a frame and/or at the outflow end of a frame, but may also be incorporated at any portion of a frame between the inflow end and the outflow end. Frames including the patterns illustrated in FIGS. 64A and 64B may be configured similarly to any of the frame embodiments described herein. The strut patterns may be repeated around the circumference of the frame in one or more rows. The rows may include one strut pattern, or more than one strut pattern.

FIG. 64A illustrates a unit cell 1100 including a first row I of angled struts 1102 defining an angle θ between them. A second row II of angled struts 1104 can be axially spaced apart from the struts 1102, and can also comprise the angle θ (or a different angle). Struts 1106 and 1108 can extend between the struts 1102 of the first row I and the struts 1104 of the second row II in a cross pattern. The angle θ can be configured to resist further expansion of the frame beyond a specified diameter. For example, the angle θ can be from 120° to 180°, 140° to 180°, 160° to 180°, or 180°. In other embodiments, the struts 1106 and 1108 can comprise four struts that meet at a junction.

FIG. 64B illustrates an alternative configuration of the unit cell 1100 in which the struts 1106 and 1108 extend axially between the rows I and II.

Figure 64C:
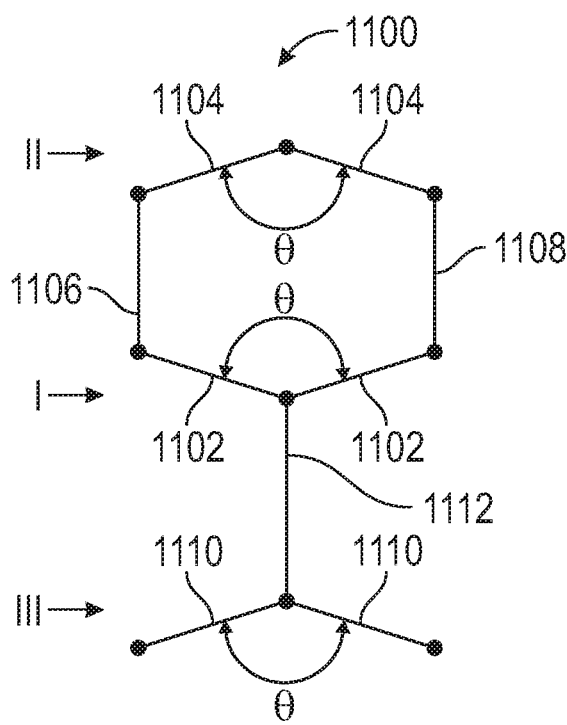

FIG. 64C illustrates a variation of the unit cell 1100 of FIG. 64B in which the struts 1106 and 1108 are shortened, and the unit cell further comprises a third row III of angled struts 1110 spaced apart from the first row I and interconnected with the first row I by an axially extending strut member 1112. The struts 1110 of the third row III can define the angle θ (or a different angle), and can also be configured to resist expansion of the frame beyond a specified diameter.

Figure 64D:
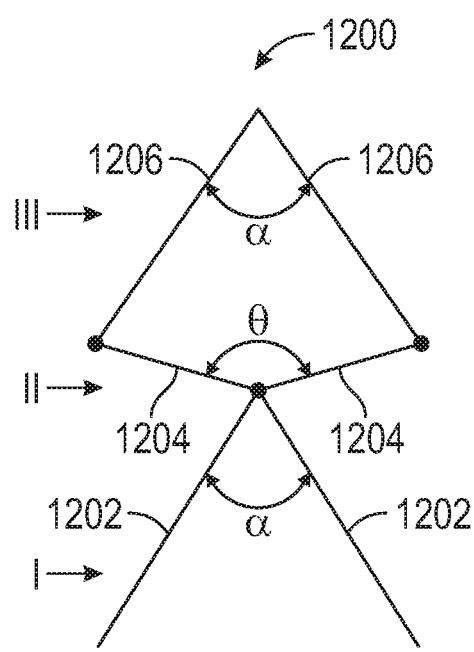

FIG. 64D illustrates another variation of a unit cell 1200 including a first row I of angled struts 1202, a second row II of angled struts 1204, and a third row III of angled struts 1206. The struts 1202 of the first row I can define a first angle α between them. The struts 1204 of the second row II can define a second angle θ between them, which can be larger than the angle α, and can be configured to resist expansion of at least the second row II of struts beyond a specified diameter. The struts 1206 of the third row III can comprise the angle α. In certain embodiments, the unit cell patterns of FIGS. 64C and 64D can be middle strut row patterns configured for use between the inflow and outflow ends of a frame, potentially in combination with one or more of the unit cells of FIGS. 64A and/or 64B. The various unit cell configurations of FIGS. 64A-64D can be combined in any combination with each other, and with any of the other frame embodiments described herein. Any of the struts of the various rows, and/or any of the interconnecting struts extending between rows, may also have various strut widths as described above.

Explanation of Terms

Any of the sealing element embodiments disclosed herein can be used in combination with any of the disclosed prosthetic heart valve and/or frame embodiments. A prosthetic heart valve can also include any of the sealing elements described herein, or portions thereof, in any combination.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the terms "coupled" and "associated" generally mean electrically, electromagnetically, and/or physically (e.g., mechanically or chemically) coupled or linked and does not exclude the presence of intermediate elements between the coupled or associated items absent specific contrary language.

In the context of the present application, the terms "lower" and "upper" are used interchangeably with the terms "inflow" and "outflow", respectively. Thus, for example, in certain configurations the lower end of the valve is its inflow end and the upper end of the valve is its outflow end.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device toward the user, while distal motion of the device is motion of the device away from the user. The terms "longitudinal" and "axial" refer to an axis extending in the proximal and distal directions, unless otherwise expressly defined.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under test conditions/methods familiar to those of ordinary skill in the art. When directly and explicitly distinguishing embodiments from discussed prior art, the embodiment numbers are not approximates unless the word "about" is recited. Furthermore, not all alternatives recited herein are equivalents.

In some examples, values, procedures, or apparatus may be referred to as "lowest," "best," "minimum," or the like. It will be appreciated that such descriptions are intended to indicate that a selection among many alternatives can be made, and such selections need not be better, smaller, or otherwise preferable to other selections.

In the description, certain terms may be used such as "up," "down," "upper," "lower," "horizontal," "vertical," "left," "right," and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object.

In view of the many possible embodiments to which the principles of the disclosure may be applied, it should be recognized that the illustrated embodiments are only preferred examples and should not be taken as limiting the scope of the disclosure. Rather, the scope of the disclosure is at least as broad the following claims. We therefore claim all that comes within the scope and spirit of these claims.

The invention claimed is:

1. A prosthetic heart valve, comprising:
a frame comprising a plastically-expanded material, the frame including an inflow end, an outflow end, and a central portion between the inflow end and the outflow end, the frame being radially collapsible to a collapsed configuration and expandable from the collapsed configuration to an expanded configuration, the frame comprising five or fewer rows of strut members, the inflow end compirsing a plurality of circumferentially extending first strut members arranged in a first row of the five or fewer or fewer rows of strut members, the first strut members having a first strut width and forming a first angle between adjacent first strut members in the first row, the central portion comprising a plurality of circumferentially extending second strut members arranged in a second row of the five or fewer rows of strut members, the second second strut members having a second strut width and forming a second angle between adjacent second strut members in the second row, the outflow end of the frame comprises a plurality of circumferentially extending third strut members in a third row of the five or fewer rows of strut members, the third strut members having a third strut width and forming a third angle between adjacent third strut members; and
a plurality of leaflets positioned at least partially within the frame and configured to regulate a flow of blood through the prosthetic heart valve;
wherein the first angle is 110° to 170°, the second angle is 80° to 100°, the third angle is less than the first angle and less than the second angle, and the third strut width is equal to the first and second strut widths such that when crimped onto a cylindrical balloon of a delivery apparatus and plastically expanded to the expanded configuration a diameter of the outflow end of the frame is greater than a diameter of the central portion of the frame and greater than a diameter of the inflow end of the frame, and the frame has a Y-shaped profile; and wherein the second row of the five or fewer rows of strut members is one of three rows of second strut members in the central portion of the frame, each of the three rows of second strut members being one of the five or fewer rows of strut members, the second strut members in each of the three rows of second strut members having the same length, and wherein adjacent second strut members in each row of second strut members define the second angle.

2. The prosthetic heart valve of claim 1, wherein a diameter of the inflow end is substantially equal to the diameter of the central portion such that the frame has a Y-shaped profile when expanded to the expanded configuration.

3. The prosthetic heart valve of claim 1, wherein a diameter of the inflow end and the diameter of the outflow end are greater than the diameter of the central portion of the frame when the frame is between the collapsed configuration and the expanded configuration such that the frame has an hourglass-shaped profile.

4. The prosthetic heart valve of claim 1, wherein the diameter of the inflow end and the diameter of the outflow end are greater than the diameter of the central portion when the frame is between the collapsed configuration and the expanded configuration such that the frame has an hourglass-shaped profile.

5. The prosthetic heart valve of claim 1, wherein junctions between first strut members are longitudinally spaced apart from junctions between second strut members by axially extending inflow strut members.

6. The prosthetic heart valve of claim 5, wherein the outflow end of the frame comprises a plurality of circumferentially extending third strut members, the third strut members being longitudinally spaced apart from the second strut members of the central portion by axially extending outflow strut members.

7. The prosthetic heart valve of claim 1, wherein the first strut members and the second strut members have the same length.

8. The prosthetic heart valve of claim 1, wherein each row of strut members of the frame extends continuously around the entire circumference of the frame.

9. The prosthetic heart valve of claim 1, wherein in an as-manufactured expanded configuration the frame has a cylindrical shape, and when crimped onto the cylindrical balloon of the delivery apparatus and plastically expanded to an expanded deployment configuration with the cylindrical balloon the frame has a y-shaped profile.

10. A prosthetic heart valve, comprising:
a frame comprising a plastically-expandable material, the frame including an inflow end, an outflow end, and a central portion between the inflow end and the outflow end, the frame being radially collapsible to a collapsed configuration and expandable from the collapsed configuration to an expanded configuration, the frame comprising five or fewer rows of strut members, the inflow end comprising a plurality of circumferentially extending first strut members arranged in a first row of the five or fewer rows of strut members, the first strut members having a first strut width and forming a first angle between adjacent first strut members in the first row, the central portion of the frame comprising a plurality of circumferentially extending second strut members arranged in a second row of the five or fewer rows of strut members, the second strut members having a second strut width and forming a second angle between adjacent second strut members in the second row, the outflow end comprising a plurality of circumferentially extending third strut members arranged in a third row of the five or fewer rows of strut members, the third strut members having a third strut width and forming a third angle between adjacent third strut members in the third row; and
a plurality of leaflets positioned at least partially within the frame and configured to regulate a flow of blood through the prosthetic heart valve;
wherein the first angle is 110° to 170°, the second angle is 85° to 100°, the third angle is 70° to 84°, and the third strut width is equal to the first and second strut widths such that when crimped onto a cylindral ballon of a delivery apparatus and plastically expanded to the expanded configuration a diameter of the outflow end of the frame is greater than a diameter of the central portion of the frame and greater than a diameter of the inflow end of the frame, and the frame has a Y-shaped profile; and
wherein the second row of the five or fewer rows of strut members is one of three rows of second strut members in the central portion of the frame, each of the three rows of second strut members being one of the five or fewer rows of strut members, the second strut members in each of the three rows of second strut members having the same length, and wherein adjacent second strut members in each row of second strut members define the second angle.

11. The prosthetic heart valve of claim 10, wherein a diameter of the inflow end is substantially equal to the diameter of the central in the expanded configuration.

12. The prosthetic heart valve of claim 10, wherein the diameter of the inflow end and the diameter of the outflow end are greater than the diameter of the central portion of the frame when the frame is between the collapsed configuration and the expanded configuration such that the frame has an hourglass-shaped profile.

* * * * *